United States Patent
Nair et al.

(10) Patent No.: US 10,086,081 B2
(45) Date of Patent: Oct. 2, 2018

(54) CARBOHYDRATE CONJUGATED RNA AGENTS AND PROCESS FOR THEIR PREPARATION

(71) Applicant: ALNYLAM PHARMACEUTICALS, INC., Cambridge, MA (US)

(72) Inventors: Jayaprakash K. Nair, Cambridge, MA (US); Alexander V. Kelin, Cambridge, MA (US); Pachamuthu Kandasamy, Cambridge, MA (US); Kallanthottathil G. Rajeev, Cambridge, MA (US); Muthiah Manoharan, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 156 days.

(21) Appl. No.: 14/420,189

(22) PCT Filed: Aug. 6, 2013

(86) PCT No.: PCT/US2013/053824
§ 371 (c)(1),
(2) Date: Feb. 6, 2015

(87) PCT Pub. No.: WO2014/025805
PCT Pub. Date: Feb. 13, 2014

(65) Prior Publication Data
US 2015/0196655 A1    Jul. 16, 2015

Related U.S. Application Data

(60) Provisional application No. 61/794,114, filed on Mar. 15, 2013, provisional application No. 61/680,069, filed on Aug. 6, 2012.

(51) Int. Cl.
*C07H 1/00*     (2006.01)
*C07H 15/26*    (2006.01)
*A61K 47/48*    (2006.01)
*A61K 31/7088*  (2006.01)
*C07C 231/14*   (2006.01)
*C07D 207/12*   (2006.01)
*C12N 15/113*   (2010.01)

(52) U.S. Cl.
CPC .... *A61K 47/48092* (2013.01); *A61K 31/7088* (2013.01); *C07C 231/14* (2013.01); *C07D 207/12* (2013.01); *C07H 1/00* (2013.01); *C07H 15/26* (2013.01); *C12N 15/113* (2013.01); *C12N 2310/351* (2013.01); *C12N 2320/32* (2013.01)

(58) Field of Classification Search
None
See application file for complete search history.

(56) References Cited

FOREIGN PATENT DOCUMENTS

| WO | WO09/073809 | * | 6/2009 |
| WO | WO-2009073809 A2 | | 6/2009 |
| WO | WO-2013075035 A1 | | 5/2013 |

OTHER PUBLICATIONS

Ceulemans, et al., Oligonucleotide Analogues with 4-Hydroxy-N-acetylprolinol as Sugar Substitute, Chem. Eur. J., 1997, 3:12:1997-2010.
Saez, et al., "Janus" Supermolecular Liquid Crystals—Giant Molecules with Hemipspherical Architectures, Chem. Eur J, 2003, 9:4869-4877.
International Search Report issued in PCT/US2013/053824 dated Oct. 9, 2013.

* cited by examiner

*Primary Examiner* — Traviss C McIntosh, III
(74) *Attorney, Agent, or Firm* — Blank Rome LLP

(57) ABSTRACT

This disclosure relates to an improved process for the preparation of carbohydrate conjugates. The disclosure also relates to carbohydrate conjugated iRNA agents comprising these carbohydrate conjugates, which have improved purity and are advantageous for the in vivo delivery of the iRNA agents.

10 Claims, No Drawings

CARBOHYDRATE CONJUGATED RNA AGENTS AND PROCESS FOR THEIR PREPARATION

This application is a U.S. national phase of International Patent Application No. PCT/US2013/053824, filed Aug. 6, 2013, which claims the benefit of U.S. Provisional Application Nos. 61/680,069, filed Aug. 6, 2012, and 61/794,114, filed Mar. 15, 2013, each of which is incorporated by reference in its entirety.

FIELD OF THE INVENTION

The present invention relates to an improved process for the preparation of carbohydrate conjugates. The present invention also relates to carbohydrate conjugated iRNA agents comprising these carbohydrate conjugates, which have improved purity and are advantageous for the in vivo delivery of the iRNA agents.

BACKGROUND OF THE INVENTION

Efficient delivery to cells in vivo requires specific targeting and substantial protection from the extracellular environment, particularly serum proteins. One method of achieving specific targeting is to conjugate a targeting moiety to an iRNA agent. The targeting moiety helps in targeting the iRNA agent to the required target site. One way a targeting moiety can improve delivery is by receptor mediated endocytotic activity. This mechanism of uptake involves the movement of iRNA agent bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal.

Recently, certain carbohydrate conjugates have been shown to be a valuable delivery alternatively to liposomes for siRNA delivery.

SUMMARY OF THE INVENTION

The present invention relates to an improved process for the preparation of carbohydrate conjugates, and carbohydrate conjugated iRNA agents. The process described herein affords a carbohydrate conjugate product that contains fewer impurities (e.g., fewer metal contaminants). The present invention also eliminates the need for expensive hydrogenation reactions using catalysts such as Pd on carbon, and reduces the number of purification steps to obtain a pharmaceutically acceptable product.

The processes, intermediates, and products of the present invention are useful for preparing carbohydrate-conjugated iRNA agents, such as those having the formula:

Formula (A)

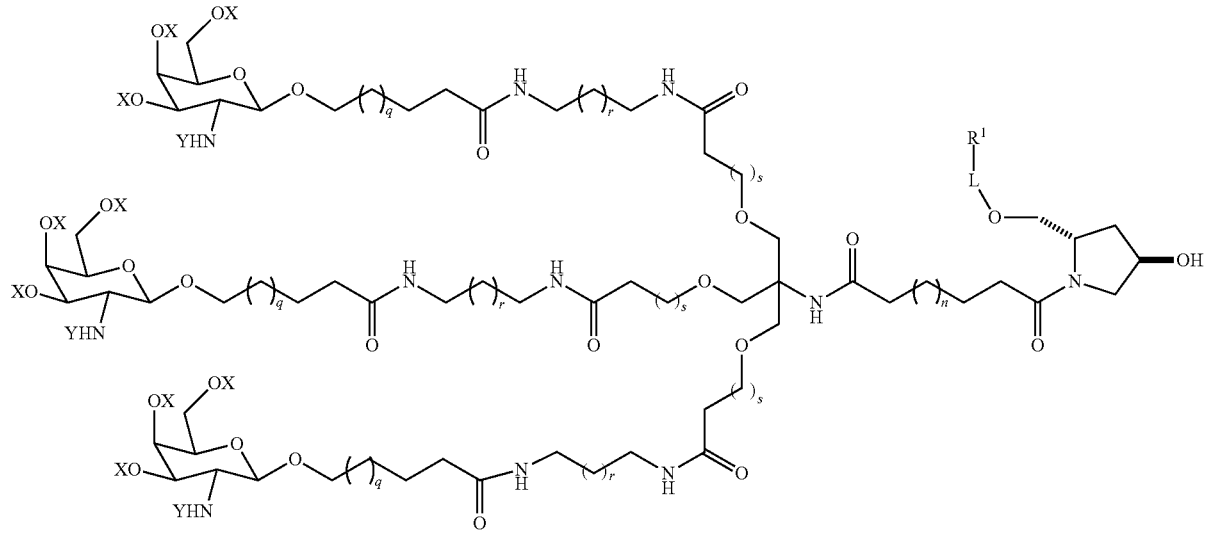

wherein each occurrence of X is a hydroxy protecting group or hydrogen;

each occurrence of Y is an amine protecting group (e.g., acetyl);

n is 0-20 (e.g., 0-15 or 4-15, preferably 7);

each occurrence of q, r and s is independently 1-7;

L is a linking group; and $R^1$ is an iRNA agent. In one embodiment, all occurrences of X are the same, all occurrences of Y are the same, all occurrences of q are the same, all occurrences of r are the same, and all occurrences of s are the same. In one embodiment, each occurrence of X is hydrogen. In another embodiment, each occurrence of Y is acetyl. In one embodiment, each occurrence of X is hydrogen and each occurrence of Y is acetyl.

In one preferred embodiment, n is 6, q is 1, r is 1, and s is 1. In another preferred embodiment, n is 7, q is 1, r is 1, and s is 1. The carbohydrate-conjugated iRNA agent is preferably substantially free of metal (such as a metal ion).

One embodiment of the present invention is a compound of formula (A) where the compound is free or substantially free of one or more of (i) metal impurities (such as palladium, platinum, and ruthenium), (ii) each of the following two urea side products

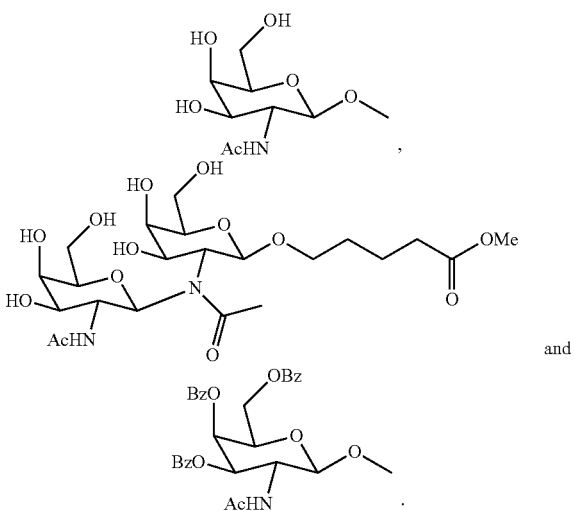

(iii) each of the following saccharide compounds

In one preferred embodiment, the compound of formula (A) contains no more than about 0.5%, or more preferably no more than about 0.2%, of any individual urea side product or saccharide compound described above. For instance, the compound can contain no more than about 0.1 or about 0.05% of any individual urea side product or saccharide compound described above. The compound of formula (A) also preferably contains no more than about 1000 ppm (e.g., no more than about 400, about 300, about 200, about 100, about 50, about 10, about 5, or 1 about ppm) of any individual metal (such as palladium, platinum or ruthenium). In one embodiment, the compound of formula (A) contains no more than about 1000 ppm (e.g., no more than about 400, about 300, about 200, about 100, about 50, about 10, about 5, or 1 about ppm) of (i) ruthenium, (ii) palladium, (iii) platinum or (iv) any combination thereof.

One embodiment of the present invention relates to a process for converting a compound of formula (VI) to a compound of formula (VII):

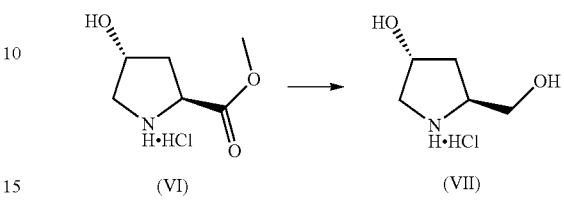

The process may comprise:

(i) reacting the compound of formula (VI) with a base such as a metal alkoxide base (e.g., NaOMe);

(ii) reducing the product of step (i) (e.g., with NaBH$_4$); and (iii) reacting the product of step (ii) with an acid (e.g., HCl).

This process may be performed in a single pot, and with high yield (e.g., >80%).

For example, in one embodiment, the compound of formula (VI) is reacted with a metal alkoxide (such as sodium methoxide). Step (ii) may include reaction with a reducing agent, such as a borohydride, e.g., sodium borohydride. In one embodiment, step (ii) involves more than 1 equivalent, such as 2-5 equivalents (e.g., 3 equivalents), of the reducing agent. In a further embodiment, the acid used in step (iii) is a mineral acid, e.g., hydrochloric acid. In a preferred embodiment, steps (i), (ii) and (iii) are performed at the same time, i.e., the process is a one-step process. The inventors have surprisingly found that this process of preparing compound (VII) eliminates a hydrogenation step and the use of costly reagents (e.g., benzyl chloroformate and Pd on carbon). The resulting product is crystalline and contains lower amounts of heavy metal impurities (such as palladium and ruthenium) which can carry through during synthesis to contaminate the compound of formula (A) or (I). (The compound of formula (I) is shown further below.)

The compound of formula (VII) may be converted to a compound of formula (A) or (I).

Another embodiment relates to a process for preparing a compound of formula (VIII):

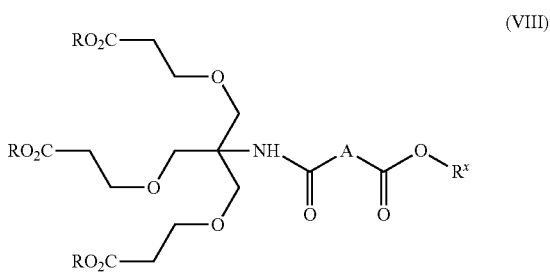

wherein

A is a $C_6$-$C_{14}$ alkylene linker (e.g., a $C_8$-$C_{12}$ alkylene linker, such as —(CH$_2$)$_{10}$—);

each R is, independently, an acid protecting group (e.g., substituted or unsubstituted alkyl (e.g., t-butyl) or substituted or unsubstituted aryl); and R[x] is an acid protecting group, such as substituted or unsubstituted alkyl (e.g., methyl) or substituted or unsubstituted aryl. Preferably, R[x] is different from all the R groups.

The process includes reacting a compound of the formula (IX):

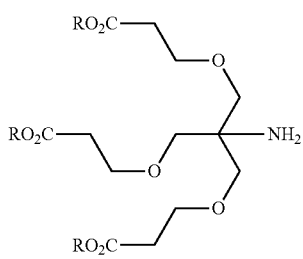

with a compound of the formula (X):

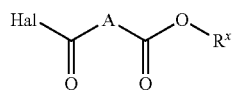

to yield a compound of formula (VIII), wherein Hal is halogen (e.g., Cl).

In one embodiment, each R is t-butyl. In another embodiment, Hal is Cl. In a further embodiment, A is a $C_{10}$ alkylene linker. In a preferred embodiment, each R is t-butyl, Hal is Cl and A is a $C_{10}$ alkylene linker.

In one embodiment, the process for preparing a compound of formula (VIII) involves reacting the compound of formula (IX) with the compound of formula (X) in the presence of DIEA (N,N-diisopropylethylamine). Applicants have suprisingly found that the use of the acid halide of formula (X) allows the reaction to be performed in the presence of DIEA (as opposed to dimethylaminopropyl carbodiimide (EDC), a reagent typically used to promote such coupling reactions) surprisingly affording a product having increased purity. The product may, for example, contain lesser amounts of substituted urea side products (or be free of or substantially free of urea side products) and contain less residual solvent (e.g., alcohol such as t-butanol). The substituted urea side products which may form are shown below.

In another embodiment, the compound of formula (VIII) is converted to a compound of formula (A) or (I).

Yet another embodiment relates to a process for preparing a compound of formula:

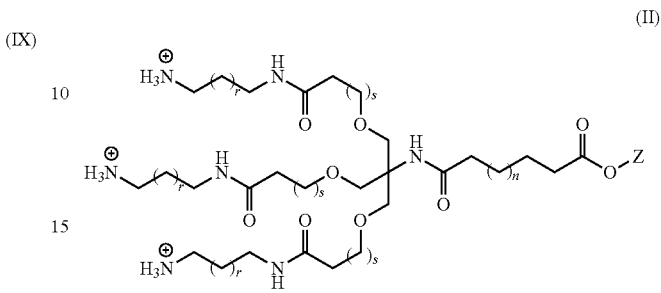

wherein Z is an acid protecting group and n, r and s are as defined above. Compound (II) may be formed with a counter ion (such as $CF_3SO_3^-$) present. The process involves reacting a compound of the formula (XII):

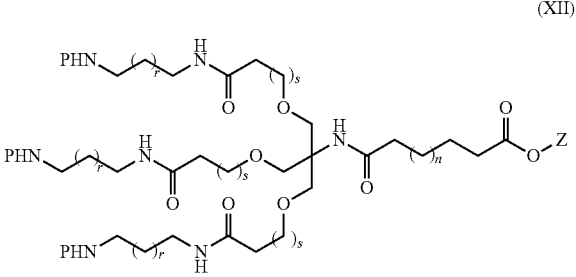

wherein P is an amino protecting group (e.g., Boc), with a sulfonic acid (e.g., p-toluene sulfonic acid or methane sulfonic acid). For example, in one embodiment, the compound of formula (XII) is reacted with p-toluene sulfonic acid in an alcohol solvent (e.g., methanol) at a temperature of between about 30° C. and about 60° C. (e.g., at about 50° C.).

The partial solubility of the triamine in halogenated solvents such as dichloromethane may lead to incomplete deprotection of the compound of formula (XII). The inventors have surprisingly found that the use of a sulfonic acid (in an alcoholic solvent such as methanol) affords greater

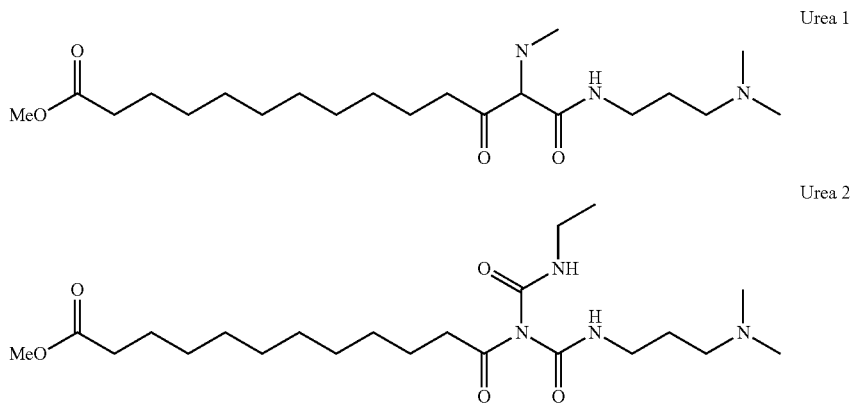

Urea 1

Urea 2 deprotection (i.e., reduces the possibility of incomplete deprotection) of the compound of formula (XII), likely due to the enhanced solubility of the triamine in the alcohol.

In another embodiment, the compound of formula (II) is converted to a compound of formula (A) or (I).

Yet another embodiment relates to a process for preparing a compound of formula (XIII):

significantly lowering costs. Additionally, the number of potential impurities in the product (due to oligomerization reactions) is reduced, and the possibility of contamination by heavy metals (such as Pd or Ru when used as catalysts) is eliminated. In one embodiment, the reaction is conducted in a chlorinated solvent (e.g., dichloromethane or dichloroethane).

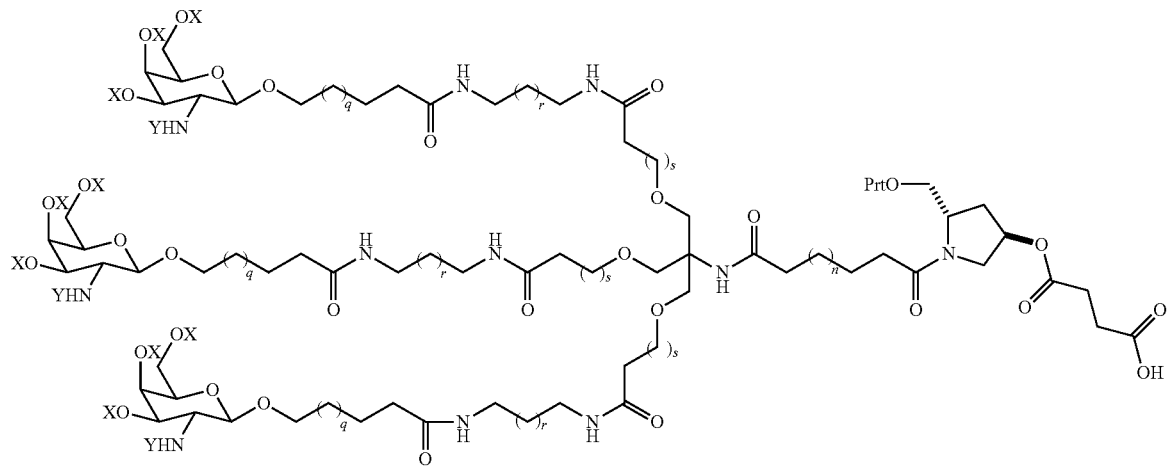

wherein

X, Y, n, q, r, and s are as defined above with respect to formula (A); and

Prt is a hydroxyl protecting group.

The process comprises reacting a compound of formula (XIV)

In another embodiment, the compound of formula (XIII) is converted to a compound of formula (A) or (I).

Any of the intermediates and products of the present invention can be converted into a carbohydrate-conjugated iRNA agent of formula (A), which contains a GalNAc$_3$ moiety.

(XIV)

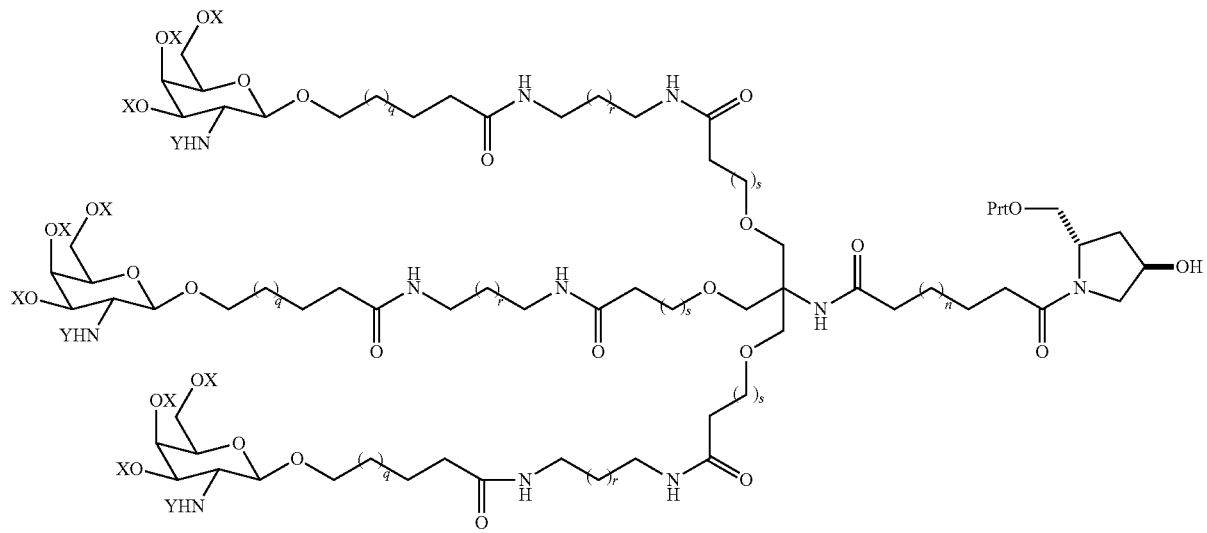

with dihydrofuran-2,5-dione in the presence of an amine (preferably a tertiary amine such as triethylamine). Applicants have surprisingly found that the succinylation reaction may be conducted in the absence of expensive catalysts typically used in this reaction such as DMAP (dimethylamino pyridine) or an immobilized DMAP (such as PS-DMAP, a polystyrene bound equivalent of DMAP), thereby Yet another embodiment is a method of preparing a carbohydrate-conjugated iRNA agent of formula (A) by (i) obtaining any of the intermediates or products disclosed herein (e.g., a compound of formula (I)), and (ii) converting it to the carbohydrate-conjugated iRNA agent of formula (A). For instance, the method may include (i) deprotecting the hydroxyl group protected by Prt on the compound of formula (I), (ii) converting the hydroxyl group to -L-R¹ (as defined in formula (A) above), and (iii) removing the solid support and succinic acid linker (which is located between the solid support and the hydroxyl group of the prolinol moiety) to obtain a compound of formula (A).

In one embodiment, the intermediates and products described herein (e.g., a compound of Formula (A) or (I)) are substantially free of metal (such as a metal ion, e.g., palladium, platinum or ruthenium). Substantially free of metal, as used herein, includes containing less than or equal to about 1000 parts per million (ppm) metal, such as less than or equal to about 800 ppm, less than or equal to about 500 ppm, less than or equal to about 400 ppm, less than or equal to about 300 ppm, less than or equal to about 200 ppm, less than or equal to about 100 ppm, less than or equal to about 50 ppm, less than or equal to about 10 ppm or less than or equal to about 1 ppm of metal.

In one embodiment, the present invention relates to a compound of formula (A) or (I) substantially free of metal (such as a metal ion), for example, containing less than or equal to about 1000 parts per million (ppm) metal, such as less than or equal to about 800 ppm, less than or equal to about 500 ppm, less than or equal to about 400 ppm, less than or equal to about 300 ppm, less than or equal to about 200 ppm, less than or equal to about 100 ppm, less than or equal to about 50 ppm, less than or equal to about 10 ppm or less than or equal to about 1 ppm of metal.

In another embodiment, the intermediates and products described herein (e.g., a compound of formula (A) or (I)) are substantially free of a counter ion (e.g., $OSO_3^-$). Substantially free of a counter ion, as used herein, includes containing less than or equal to about 1000 parts per million (ppm) of a counter ion, such as less than or equal to about 800 ppm, less than or equal to about 500 ppm, less than or equal to about 400 ppm, less than or equal to about 300 ppm, less than or equal to about 200 ppm, less than or equal to about 100 ppm, less than or equal to about 50 ppm, less than or equal to about 10 ppm or less than or equal to about 10 ppm of a counter ion.

Yet another embodiment is a compound of formula (A) or (I) which is substantially free of a counter ion, for example, containing less than or equal to about 1000 parts per million (ppm) of a counter ion, such as less than or equal to about 800 ppm, less than or equal to about 500 ppm, less than or equal to about 400 ppm, less than or equal to about 300 ppm, less than or equal to about 200 ppm, less than or equal to about 100 ppm, less than or equal to about 50 ppm, less than or equal to about 10 ppm or less than or equal to about 1 ppm of a counter ion.

Yet another embodiment is a compound of formula (A) or (I) containing less than about 10% by weight, such as less than about 7.5%, less than about 5%, less than about 4%, less than about 3%, less than about 2%, less than about 1%, less than about 0.5% or less than about 0.1% by weight of each of the following two urea side products

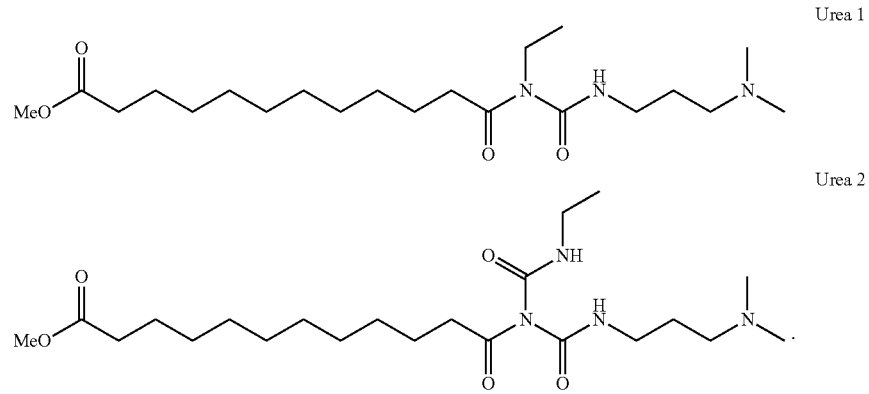

Yet another embodiment is a compound of formula (A) or (I) containing less than about 10% (based on 100% total weight of the compound), such as less than about 7.5%, less than about 5%, less than about 4%, less than about 3%, less than about 2%, less than about 1%, less than about 0.5%, or less than about 0.1% of one or more of the following compounds.

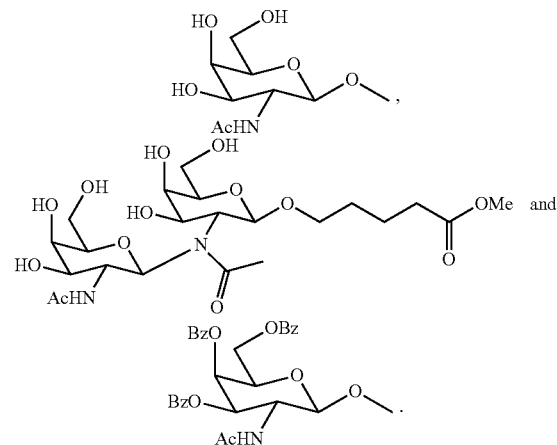

In one embodiment, the compound of formula (A) or (I) contains no more than about 0.5%, 0.4%, or 0.3% of one or more of the compounds above. In another embodiment, the compound of formula (A) or (I) contains no more than about 0.2% of one or more of the compounds above. In yet another embodiment, the compound of formula (A) or (I) contains no more than about 0.1% of one or more of the compounds above. In yet another embodiment, the compound of formula (A) or (I) contains no more than about 0.05% of one or more of the compounds above.

Yet another embodiment relates to a process for preparing a compound of formula (I):

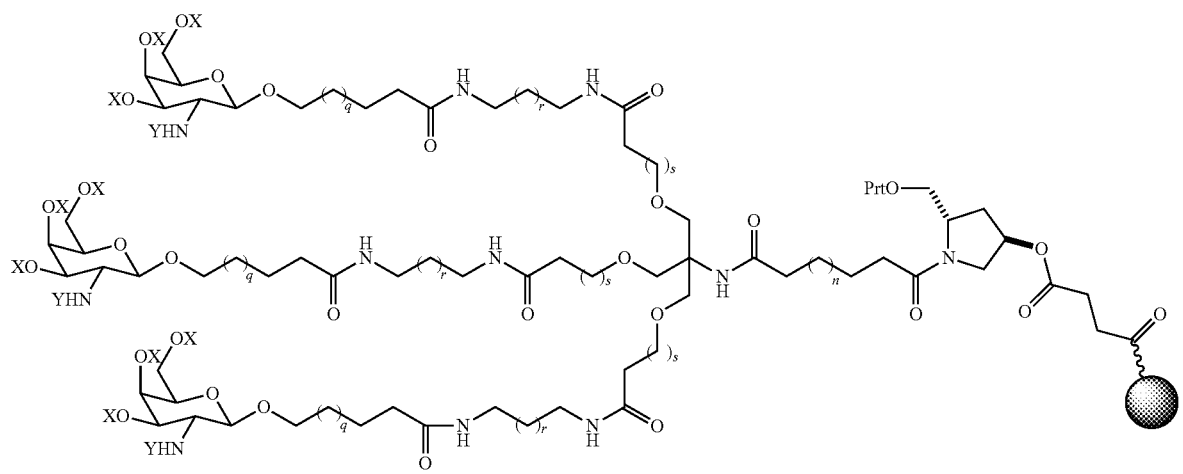

(I)

wherein
X, Y, n, q, r, and s are defined as above; and
Prt is a hydroxyl protecting group; and is a solid support.
Prt is preferably different from all the X hydroxyl protecting groups.

In one embodiment, all occurrences of X are the same, all occurrences of Y are the same, all occurrences of q are the same, all occurrences of r are the same, and all occurrences of s are the same. The process comprises one or more of the following steps:

(1) treating a compound of formula II:

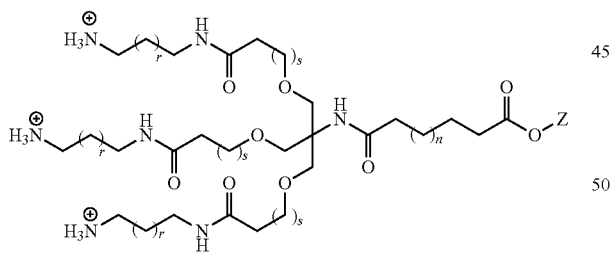

(II)

with a compound of formula III:

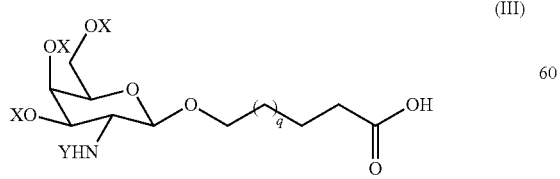

(III)

in the presence of a base to afford a compound of formula (IV):

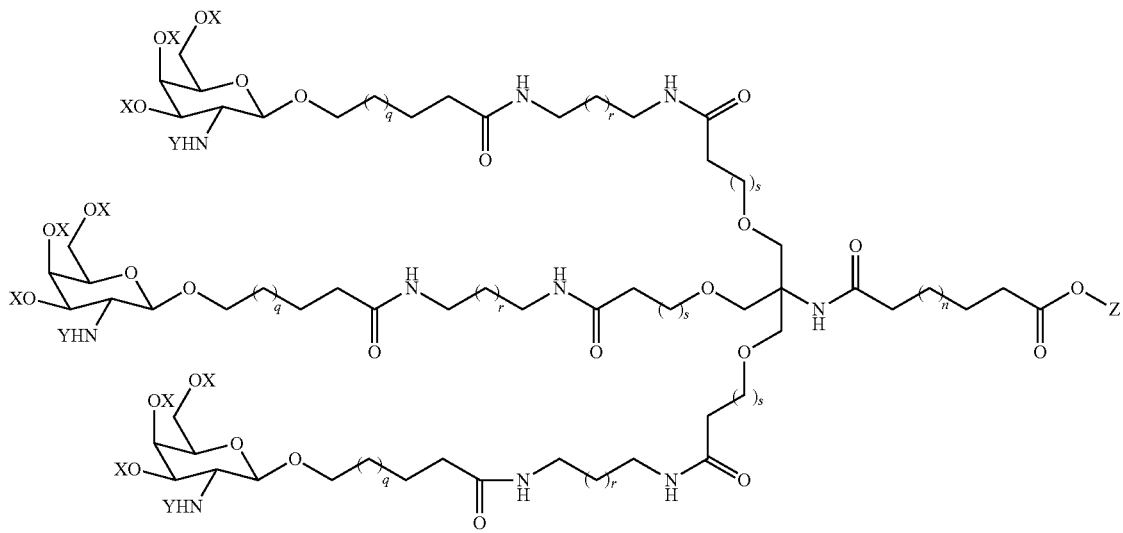

wherein Z is an acid protecting group;

(2) deprotecting Z in the compound of formula (IV), followed by coupling with a hydroxyl proline (V):

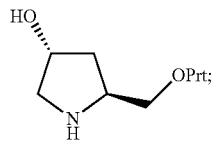

(V)

and (3) coupling the product of step (2) with succinic anhydride; and (4) coupling the product of step (3) to a solid support to afford a compound of formula (I). In the event the process does not include step (4), the intermediate formed is subsequently converted to a compound of formula (I) or (A). The compound of formula (I) is useful for preparing carbohydrate conjugated iRNA agents, such as those of formula (A).

In one embodiment, the process includes (i) step (2) (but not necessarily with steps (1), (3), and (4)), and (ii) converting the prolinol intermediate formed in step (2) to a compound of formula (A) or (I).

In one embodiment, the process is carried out in 25, 24, 23, 22, 21, 20, 19, 18, 17, 16, or 15 steps or less from the galactosamine hydrochloride salt.

In one embodiment, the process is carried out in 25, 24, 23, 22, 21, 20, 19, 18, 17, 16, or 15 steps or less staring from tris(hydroxymethyl)aminomethane.

In one embodiment, step (1) is carried out using a peptide coupling reagent in the presence of a base. Optionally, the exchange of the protecting group(s) of the galactosamine moiety (e.g., X and Y) are carried out by deprotecting a first protecting group, then reintroducing a new protecting group. For example, a benzoyl protecting group is replaced with an acetyl protecting group.

In another embodiment, step (2) is carried out by first deprotecting Z, followed by coupling to the corresponding acid with hydroxyl proline hydroxyl proline (V),

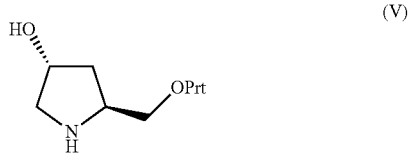

(V)

with a peptide coupling reagent in the presence of a base.

In one example, Z is an acid protecting group such as alkyl, substituted alkyl, aryl, or substituted aryl. Exemplary Z groups in accordance with the above definition include, but are not limited to, methyl, ethyl, sec-butyl, tert-butyl, chloromethyl, bromomethyl, 2-iodoethyl, 2-fluoropropyl, phenyl, 2-bromophenyl, 4-chlorophenyl, 4-methoxyphenyl, p-tolyl, o-tolyl, 4-benzyloxyphenyl, 3-carbamylphenyl, 4-chloro-3-cyanophenyl, 4-methoxy-2-tolyl, 4-trifluoromethylphenyl, benzyl, 4-methoxybenzyl, 4-iodobenzyl, 3-methanesulfonamidobenzyl, 3-nitrobenzyl, 3-chloro-4-benzyloxybenzyl, 2-ethylbenzyl, phenoxymethyl, 4-bromophenoxymethyl, 2-methoxyphenoxymethyl, 4-tolyloxymethyl, 4-chlorophenoxymethyl, 4-carbamylphenoxymethyl, 3-chloro-4-ethoxyphenoxymethyl and like groups. $R^1$ can also be 2-furylmethyl, 2-thienylmethyl, 3-thienylmethyl, cyclohexadienylmethyl, carbomethoxy, 4-nitrobenzyloxycarbonyl, 4-methoxybenzyoxycarbonyl, tert-butoxycarbonyl, and benzhydryloxycarbonyl.

In one embodiment, X is benzyl (Bz) or acetyl (Ac).

In one embodiment, Y is Ac.

In one embodiment, n is 6 and q, r, and s are 1.

In another embodiment, n is 7 and q, r, and s are 1.

In one embodiment, the processes described herein are carried out under metal free conditions.

In one embodiment, the overall yield of the process for preparing the compound of formula (I) from the compound of formula (II) is at least about 15%, such as at least about 20%, at least about 25%, at least about 30%, at least about 35%, at least about 40%, at least about 45%, or at least about 50% calculated using tris(hydroxymethyl)aminomethane or galactosamine hydrochloride salt as the starting material.

Another embodiment is a compound of formula (I):

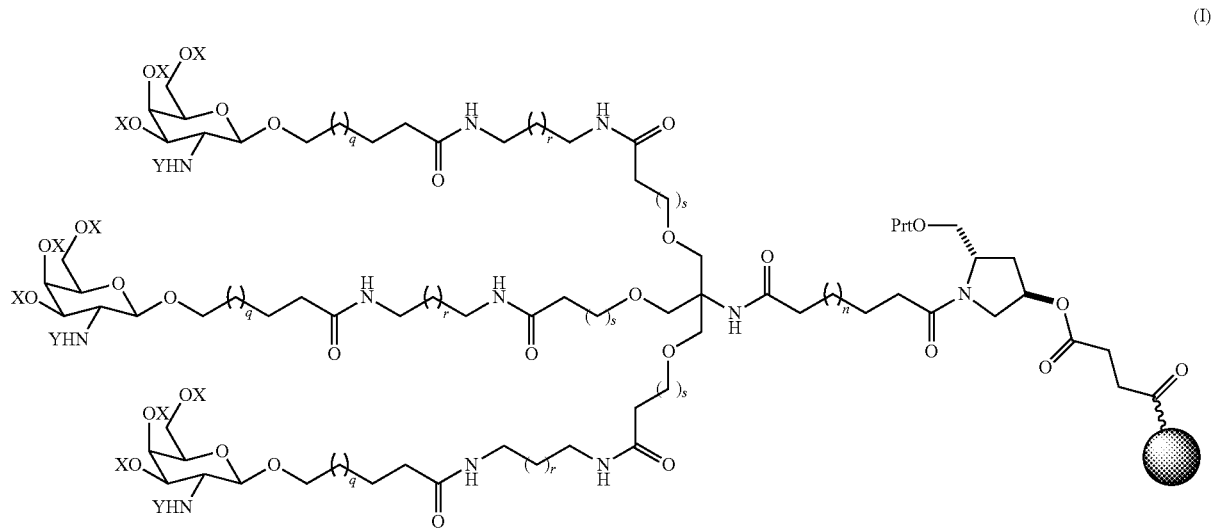

wherein X, Y, Prt, n, q, r, s, and  are as defined above, prepared by any one of the processes described herein, or a process including any one or more steps recited in the processes described herein.

Yet another embodiment is a compound of formula (A):

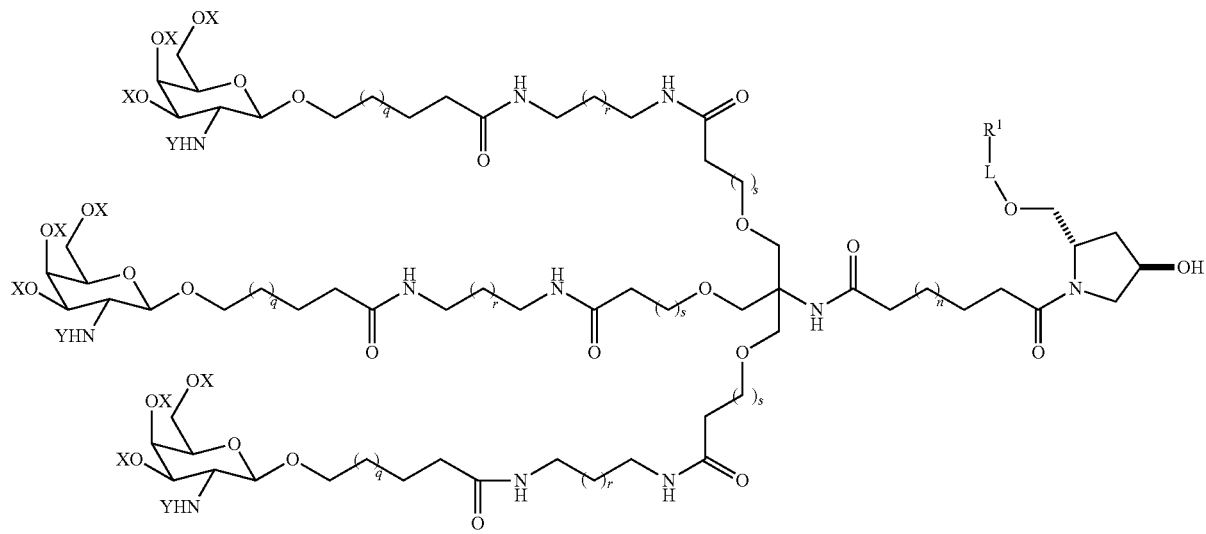

wherein L, $R^1$, X, Y, n, q, r, and s are as defined above with respect to formula (A), prepared by any one of the processes described herein, or a process including any one or more steps recited in the processes described herein.

In one embodiment of the invention, the compound of formula (I) is prepared from Tris, GalNAc, and trans-4-OH-Pro-OH with a solid support, and in the absence of any metal reagents.

In one embodiment, any of the processes described herein are used for large scale synthesis of the compound of formula (I), such as on a greater than 1 kilogram scale.

In one embodiment, any of the processes described herein are carried out in an inert solvent, such as, for example, dimethyl foramide, dimethyl sulfoxide, dichloromethane, methanol, pyridine, acetonitrile, hexane, petroleum ether, benzene, toluene, xylene; ethers (such as diethyl ether, diisopropyl ether, tetrahydrofuran, dioxane, ethylene glycol dimethyl ether), and mixtures thereof.

In other aspects, the invention further relates to increasing product yield for intermediate and large scale production of a compound of Formula (A) or (I). The compound of Formula (I) is a particularly useful intermediate in the synthesis of carbohydrate conjugated iRNA agents (such as formula (A)).

DETAILED DESCRIPTION OF THE INVENTION

Definitions

The term "linking group" refers to any suitable group for coupling the iRNA agent to the GalNAc$_3$ moiety. Examples of linking groups are provided in International Publication No. WO 2009/082607 and U.S. Patent Publication No. 2012/0136042, both of which are hereby incorporated by reference.

The term "iRNA agent" refers to an RNA agent (or agent that can be cleaved into an RNA agent) which can down regulate the expression of a target gene (e.g., a siRNA), preferably an endogenous or pathogen target RNA. While not wishing to be bound by theory, an iRNA agent may act by one or more of a number of mechanisms, including post-transcriptional cleavage of a target mRNA (referred to in the art as RNAi), or pre-transcriptional or pre-translational mechanisms. An iRNA agent can include a single strand or can include more than one strands, e.g., it can be a double stranded iRNA agent. If the iRNA agent is a single strand it can include a 5' modification which includes one or more phosphate groups or one or more analogs of a phosphate group. In one preferred embodiment, the iRNA agent is double stranded.

The iRNA agent typically includes a region of sufficient homology to the target gene, and is of sufficient length in terms of nucleotides, such that the iRNA agent, or a fragment thereof, can mediate down regulation of the target gene. The iRNA agent is or includes a region which is at least partially, and in some embodiments fully, complementary to the target RNA. It is not necessary that there be perfect complementarity between the iRNA agent and the target, but the correspondence is preferably sufficient to enable the iRNA agent, or a cleavage product thereof, to direct sequence specific silencing, e.g., by RNAi cleavage of the target RNA, e.g., mRNA.

The nucleotides in the iRNA agent may be modified (e.g., one or more nucleotides may include a 2'-F or 2'-OCH$_3$ group), or be nucleotide surrogates. The single stranded regions of an iRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. Modifications can also include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. In some embodiments, the different strands will include different modifications.

In some embodiments, it is preferred that the strands be chosen such that the iRNA agent includes a single strand or unpaired region at one or both ends of the molecule. A double stranded iRNA agent preferably has its strands paired with an overhang, e.g., one or two 5' or 3' overhangs (preferably at least a 3' overhang of 2-3 nucleotides). Preferred iRNA agents will have single-stranded overhangs, preferably 3' overhangs, of 1 or preferably 2 or 3 nucleotides in length at each end. The overhangs can be the result of one strand being longer than the other, or the result of two strands of the same length being staggered.

Preferred lengths for the duplexed regions between the strands of the iRNA agent are between 6 and 30 nucleotides in length. The preferred duplexed regions are between 15 and 30, most preferably 18, 19, 20, 21, 22, and 23 nucleotides in length. Other preferred duplexed regions are between 6 and 20 nucleotides, most preferably 6, 7, 8, 9, 10, 11 and 12 nucleotides in length.

The term "solid support," as used herein denotes in particular any particle, bead, or surface upon which synthesis of an oligonucleotide can occur. Solid supports which can be used in the different embodiments of the processes described herein can be selected for example from inorganic supports and organic supports. Inorganic supports are preferably selected from silica gel and controlled pore glass (CPG). Organic supports are preferably selected from highly crosslinked polystyrene, Tentagel (grafted copolymers consisting of a low crosslinked polystyrene matrix on which polyethylene glycol (PEG or POE) is grafted), polyvinylacetate (PVA), Poros—a copolymer of polystyrene/divinyl benzene, aminopolyethyleneglycol and cellulose. Preferred solid supports amenable to this invention include those that are hydrophobic. Preferred embodiments of the invention utilize polystyrene based solid supports. Many other solid supports are commercially available and amenable to the present invention.

The term "hydroxy protecting group," as used herein, refers to a labile chemical moiety which protects a hydroxyl group against undesired reactions during synthetic procedure(s). After the synthetic procedure(s), the hydroxy protecting group may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, and triisopropylsilyl. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which protects an amino group against undesired reactions during synthetic procedures. After the synthetic procedure(s), the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, acetyl, t-butoxycarbonyl, 9-fluorenylmethoxycarbonyl, and benzyloxycarbonyl.

The term "carboxylic acid protecting group" refers to carboxylic acid protecting groups employed to block or protect the carboxylic acid functionality while reactions involving other functional sites of the compound are carried out. Such carboxy protecting groups may be noted for their ease of cleavage by hydrolytic or by hydrogenolytic methods to the corresponding carboxylic acid. Examples of carboxylic acid ester protecting groups include, but are not limited to, methyl, tert-butyl, benzyl, 4-methoxybenzyl, C2-C6 alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri(C1-C3 alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and other acid chlorides in the presence of a tertiary amine base. Other known carboxy protecting groups such as those described by E. Haslam in *Protective Groups in Organic Chemistry*, supra, Chapter 5, are suitable. The ester forming protecting groups are preferred.

In the foregoing definitions hydroxy and carboxy protecting groups are not exhaustively defined. The function of such groups is to protect the reactive functional groups during the preparative steps and then to be removed at some later point in time without disrupting the remainder of the molecule. Many protecting groups are known in the art, and the use of other protecting groups not specifically referred to hereinabove are equally applicable.

Suitable peptide coupling reagents include, but are not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O-(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). EDC, HOAT, BOP-Cl and PyBrOP are preferred peptide coupling reagents. The amount of peptide coupling reagent is in the range of about 1.0 to about 10.0 equivalents. Optional reagents that may be used in the amide bondforming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-norbornene-2,3-dicarboxamide), in amounts ranging from about 1.0 to about 10.0 equivalents.

The term "halo" refers to any radical of fluorine, chlorine, bromine or iodine.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally interrupted with N, O, or S. For example, $C_1$-$C_{10}$ indicates that the group may have from 1 to 10 (inclusive) carbon atoms in it. The term "alkylene" refers to a divalent alkyl (i.e., —R—).

The term "alkoxy" refers to an —O-alkyl radical.

The term "alkylenedioxo" refers to a divalent species of the structure —O—R—O—, in which R represents an alkylene.

The term "aminoalkyl" refers to an alkyl substituted with an amino group.

The term "mercapto" refers to an —SH radical.

The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl and naphthyl.

The terms "arylalkyl" and "aralkyl" refers to an alkyl substituted with an aryl.

The term "arylalkoxy" refers to an alkoxy substituted with an aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively), and 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, and thiazolyl.

The terms "heteroarylalkyl" and "heteroaralkyl" refer to an alkyl substituted with a heteroaryl.

The term "heteroarylalkoxy" refers to an alkoxy substituted with a heteroaryl.

The term "heterocyclyl" refers to a non-aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively), and 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, and tetrahydrofuranyl.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by one or more substituents.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Reaction Schemes

As shown in any of Schemes 1-8 below, Ac and Bz may be replaced by any hydroxy protecting group, as described herein. Boc may be replaced by any amino protecting group, as described herein.

Conversion of Compound 1 to Compound 7A

Compound 1 may be converted to compound 7A via the sequence of reactions shown in Scheme 1 below.

Scheme 1

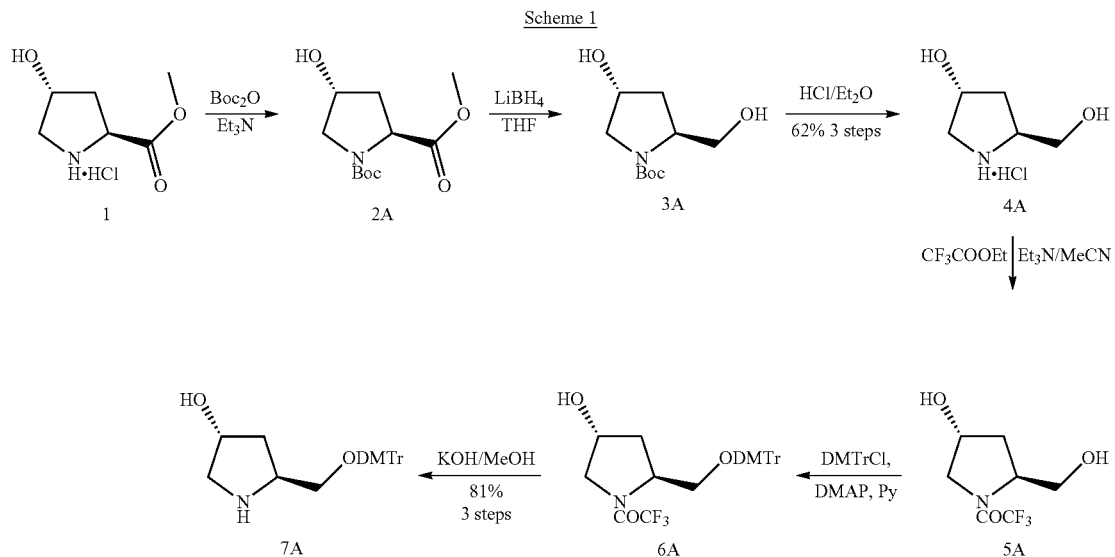

Compound 1 is converted to a nitrogen protected compound, such as compound 2A, for example, via reaction with Boc$_2$O and triethylamine. The methyl ester compound 2A is subsequently reduced to the corresponding alcohol, for example, with lithium borohydride as the reducing agent in a polar solvent such as THF. Reaction of 3A with hydrochloric acid affords the hydrochloride salt 4A. The overall yield for this three step conversion of 1 to 4A is ~62%.

The nitrogen atom of the prolinol compound 4A is protected, for example with a —COCF$_3$ group as in 5A, such as via reaction with CF$_3$CO$_2$Et in acetonitrile in the presence of an amine such as triethyl amine. The hydroxymethyl group of compound 5A is converted to —CH$_2$—ODMTr of 6A, for example, via reaction with DMTrCl (4,4'-dimethoxytrityl chloride) in the presence of DMAP and pyridine. The nitrogen atom of compound 6A is then deprotected, for example, by reaction of 6A with a base (e.g., potassium hydroxide) in an alcohol (e.g., methanol), to afford compound 7A.

Advantages of the process described in Scheme 1 include (i) no hydrogenation reactions are involved, thereby eliminating the need to use costly reagent such as Pd on carbon, (ii) compound 4A is crystalline, which makes it easier to handle and purify, and (iii) no heavy metal contaminants (such as Pd) are introduced into the system.

Alternative Conversion of Compound 1 to Compound 4A

Alternatively, compound 1 may be converted to compound 4A in a one step process by reacting compound 1 with an alkoxide, such as sodium methoxide, adding a reducing agent (e.g., sodium borohydride) and then adding hydrochloric acid. The overall yield of this one step process is 84%.

Conversion of Compound 8 to Compound 13A

Compound 8 may be converted to Compound 13A via the sequence of reactions shown in Scheme 2 below.

Scheme 2

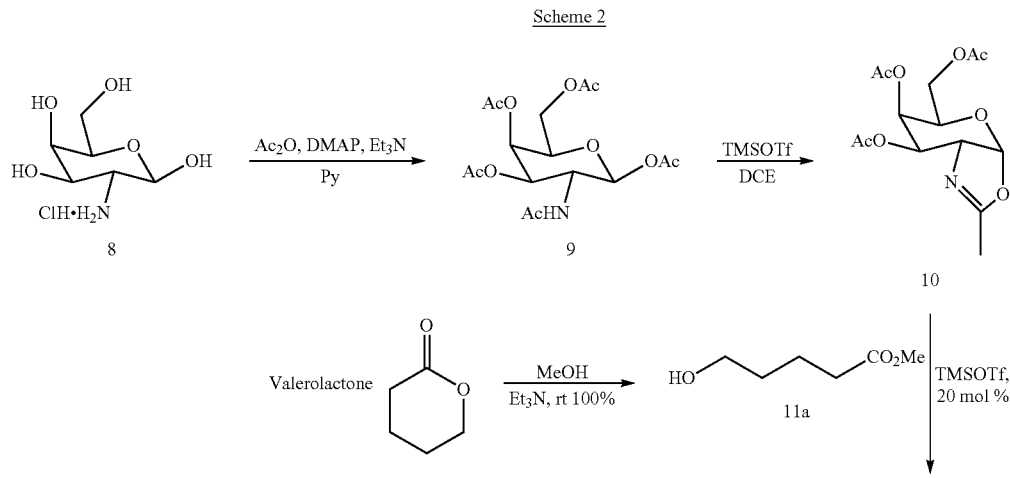

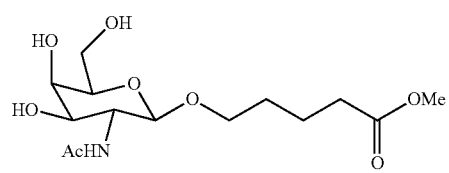

12B

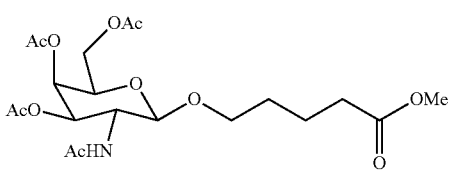

12A

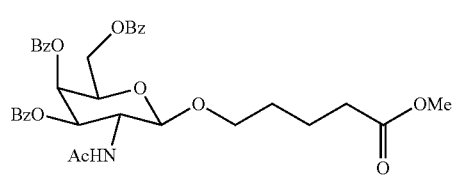

12C

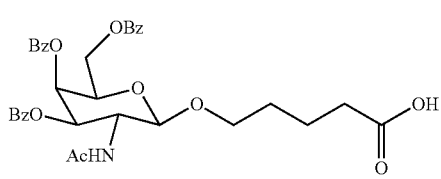

13A

The hydroxyl groups at the 1-, 3-, 4-, and 6-positions of the sugar compound 8 are protected, for example with acetyl (Ac) groups, and the amino group at the 2-position is substituted, for example, with an acetyl group, to yield compound 9. For instance, compound 8 may be reacted with $Ac_2O$ and DMAP in the presence of triethylamine to afford compound 9. The hydroxyl group at the 1-position is then activated, for example, by converting compound 9 to compound 10 by reaction with TMSOTf in dichloroethane. Reaction of compound 10 with compound 11A (which can be formed from valerolactone and methanol) affords compound 12A. The hydroxyl groups at the 3-, 4-, and 6-positions are then deprotected, for example, by reaction with triethylamine in methanol, to yield compound 12B. The alcohol groups may be re-protected, for example, with benzyl groups by reaction with $Bz_2O$ in the presence of DMAP and pyridine to afford compound 12C. The methyl ester group in compound 12C is then hydrolyzed to yield compound 13A, for example, by reaction with lithium iodide and pyridine, followed by the addition of triethylamine, sodium chloride and water.

Advantages of the process described in Scheme 2 include (i) no heavy metal (such as ruthenium) oxidation step is involved, and (ii) compounds 12B and 12C are crystalline, which makes them easier to handle and purify.

Conversion of Compound 16 to Compound 19A

Compound 16 may be converted to Compound 19A via the sequence of reactions shown in Scheme 3 below.

Scheme 3

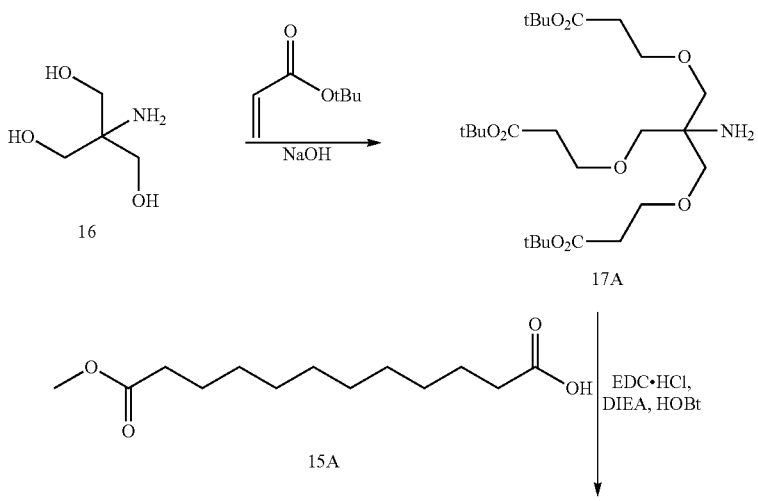

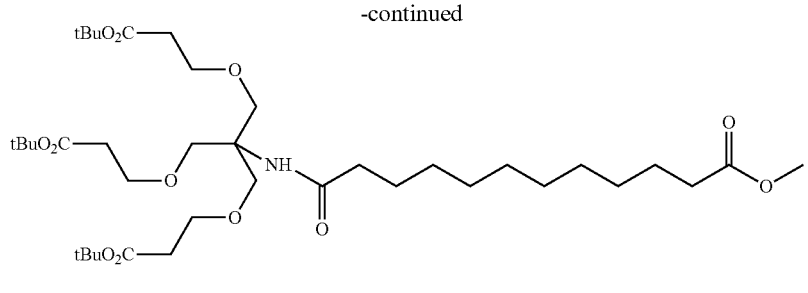

18A

HCOOH | 24 h, RT

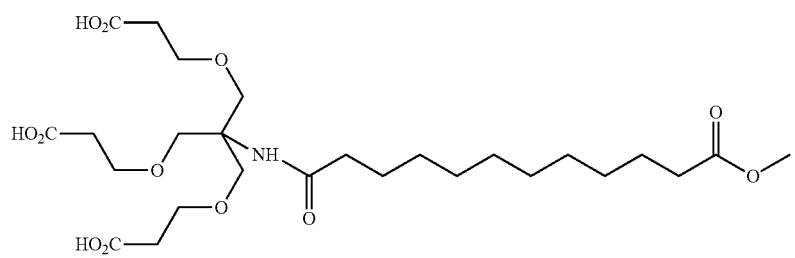

19A

Compound 16 is converted to compound 17A, for example, by reaction with t-butyl acrylate and sodium hydroxide. Reaction of compound 17A with compound 15A in the presence of a peptide coupling reagent (such as EDC), HCl, DIEA and t-butanol affords compound 18A, which is converted to the tris-acid 19A, for example, by reaction with methanoic acid.

Advantages of the process described in Scheme 3 include (i) the use of benzyl chloroformate is eliminated, (ii) no hydrogenation reactions are required (thereby avoiding the possible introduction of heavy metals such as Pd), and (iii) compound 19A is crystalline. Moreover, the use of compound 15A, which is commercially available, reduces the number of synthetic steps, as no additional synthetic steps are required to prepare a mono ester protected analog, such as 12-(benzyloxy)-12-oxododecanoic acid, which can be prepared from 1,12-dodecanoic acid.

Conversion of Compound 19A to Compound 25A

Compound 16 may be converted to Compound 19A via the sequence of reactions shown in Scheme 4 below.

Scheme 4

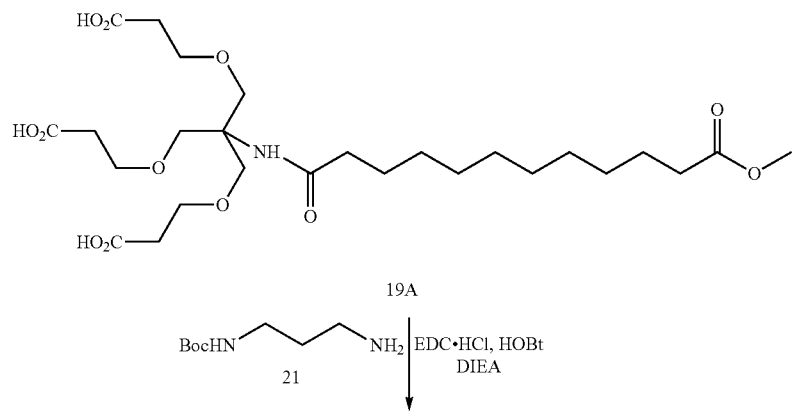

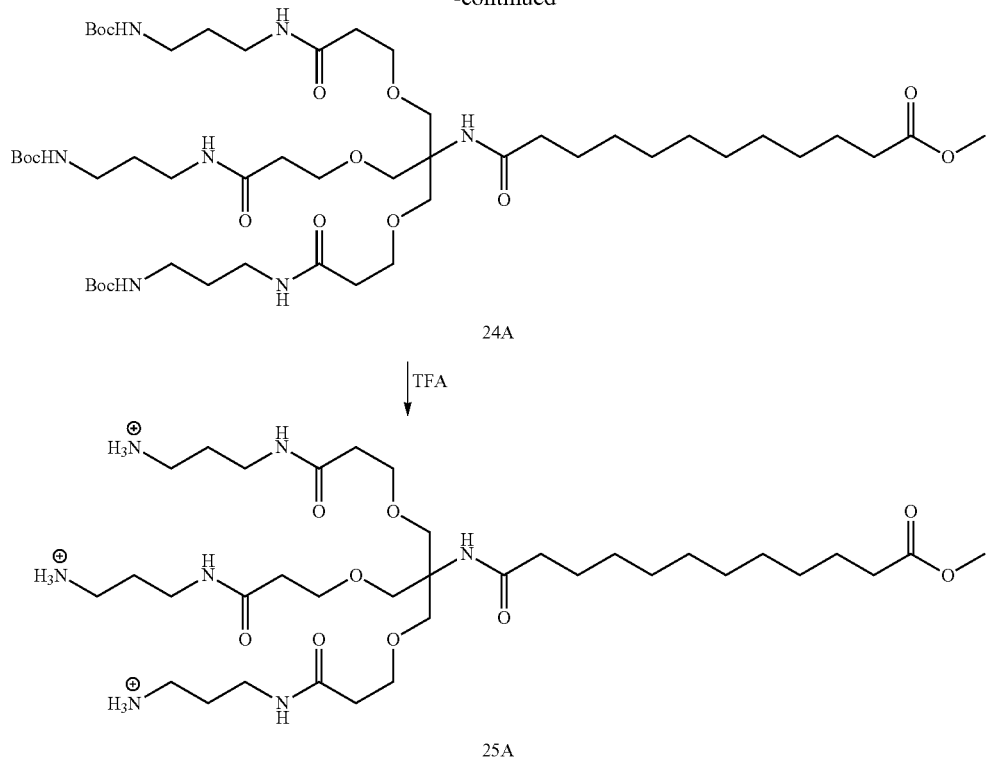

24A

↓ TFA

25A

Reaction of compound 19A with compound 21 in the presence of a peptide coupling reagent (such as EDC), HCl, DIEA and t-butanol affords compound 24A. The terminal amino groups of compound 24A are deprotected, for example by reaction with TFA (trifluoroacetic acid) to afford compound 25A.

Alternatively, compound 24A may be deprotected by reaction with a sulfonic acid (e.g., p-toluene sulfonic acid or methane sulfonic acid) in an alcoholic solvent. The use of a sulfonic acid (in an alcoholic solvent such as methanol) affords greater deprotection (i.e. reduces the possibility of incomplete deprotection) of the compound of compound 24A, likely due to the enhanced solubility of the triamine in the alcohol.

Conversion of Compound 25A to Compound 26A

Compound 25A may be converted to Compound 26A via the sequence of reactions shown in Scheme 5 below.

Scheme 5

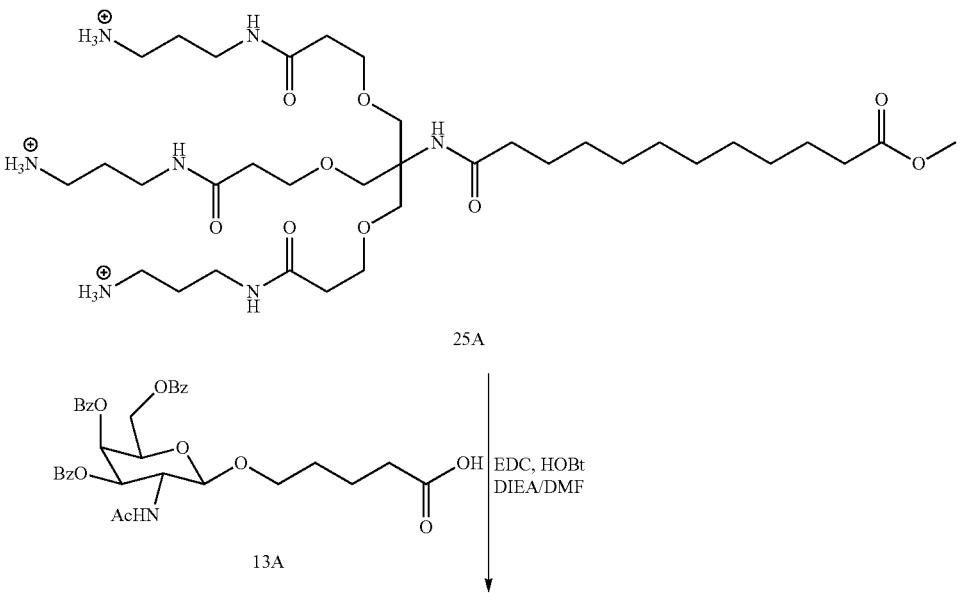

-continued

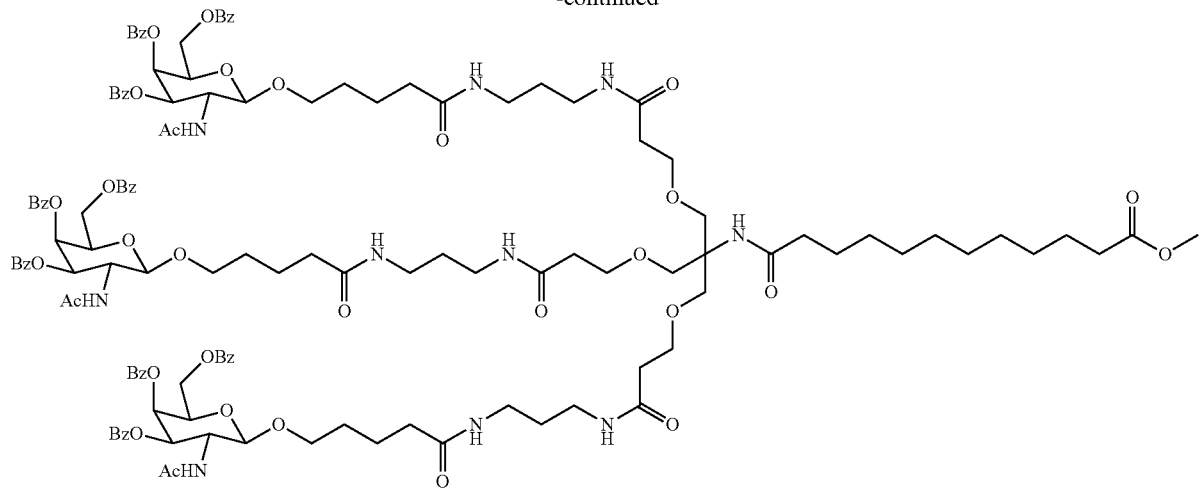

26A

Reaction of compound 25A with a peptide coupling reagent (such as EDC), DIEA in dimethylformamide and t-butanol affords compound 26A. The use of EDC as the coupling agent affords a higher yield of compound 26A.

Conversion of Compound 26A to Compound 27A

Compound 26A may be converted to Compound 27A via the sequence of reactions shown in Scheme 6 below.

Scheme 6

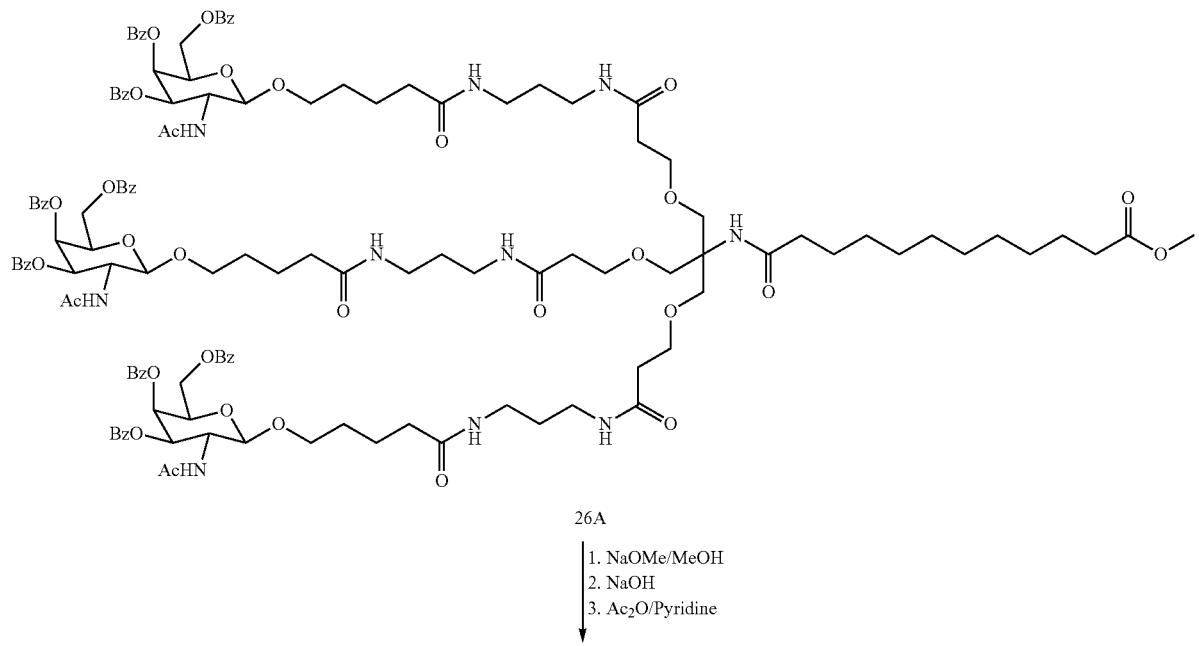

26A

1. NaOMe/MeOH
2. NaOH
3. Ac₂O/Pyridine

-continued

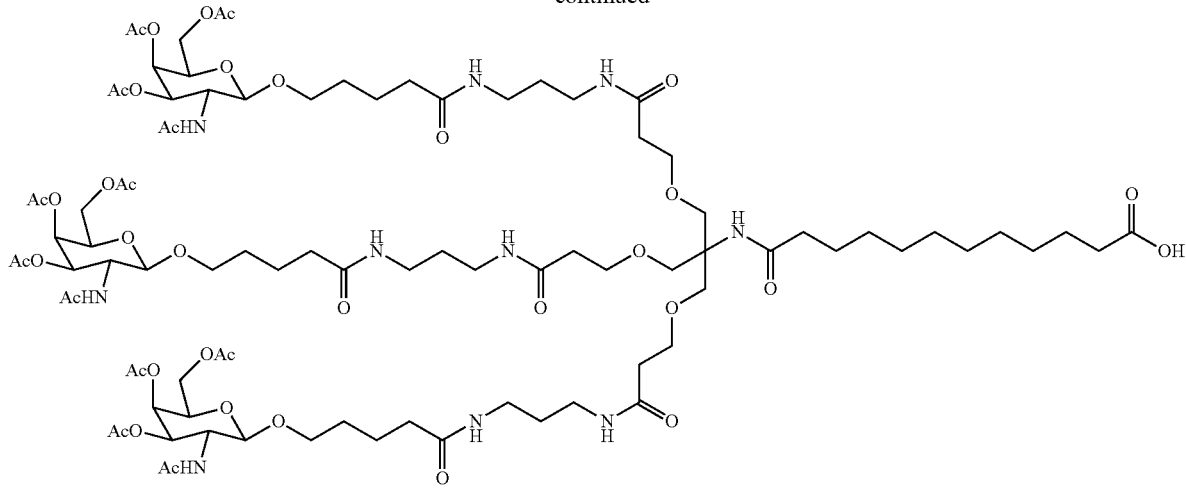

27A

The carboxylic acid terminus in compound 26A is deprotected to afford compound 27A. Compound 26A may be converted to compound 27A by reaction with (i) an alkoxide (e.g., sodium methoxide) in an alcohol (e.g., methanol), (ii) a hydroxide (e.g., sodium hydroxide) and (iii) Ac$_2$O in pyridine. No hydrogenation step is required in this conversion of 26A to 27A.

Conversion of Compound 27A to Compound 29A

Compound 27A may be converted to Compound 29A via the sequence of reactions shown in Scheme 7 below.

Scheme 7

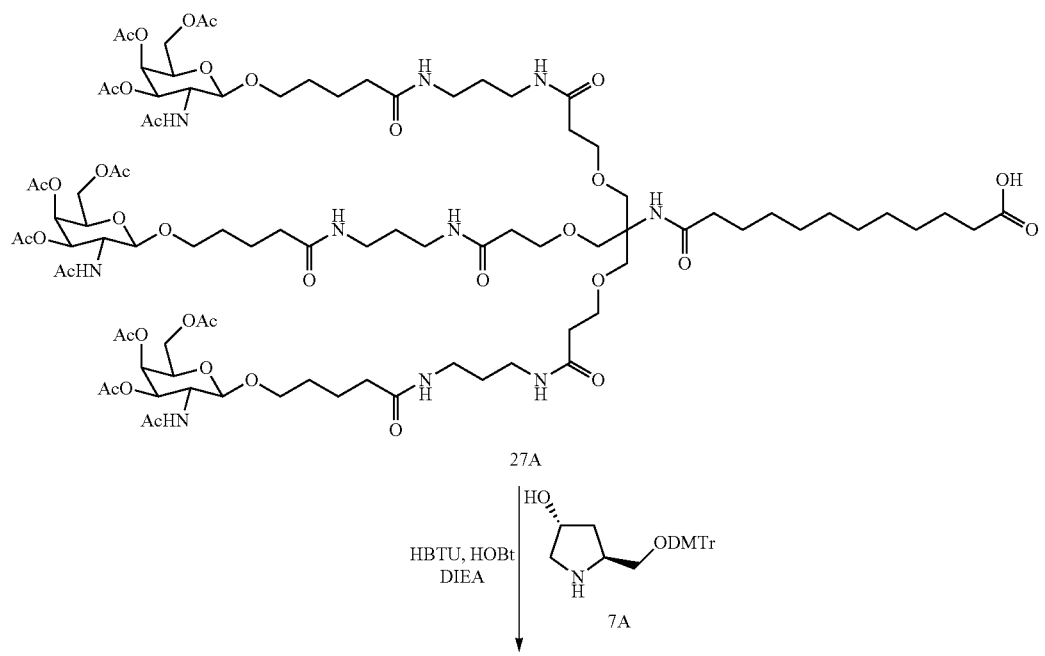

-continued

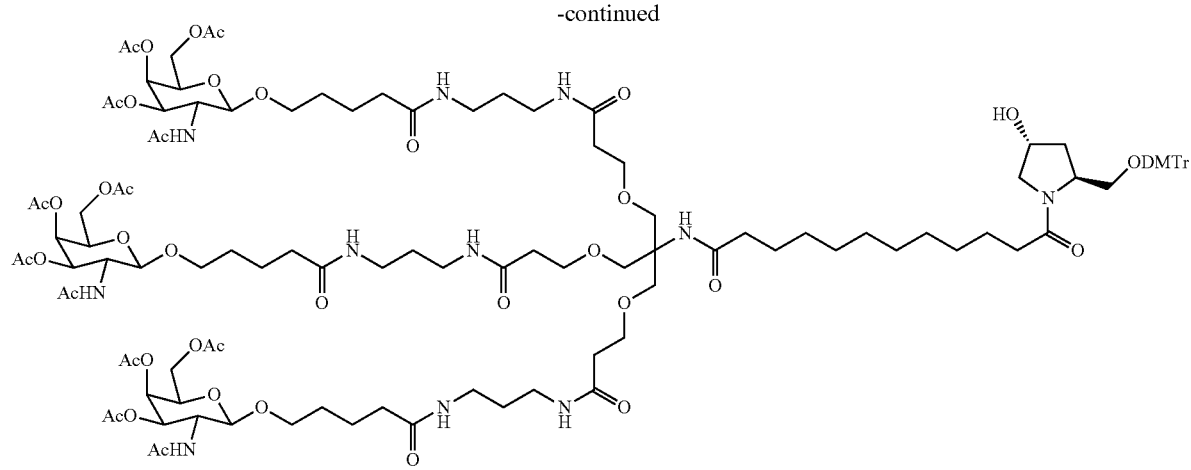

29A

Reaction of compound 27A with compound 7A (which may be prepared as described above) in the presence of a peptide coupling reagent (such as HBTU), DIEA and t-butanol affords compound 29A. Advantages of the process described in Scheme 7 include (i) the use of a fluoride salt (i.e., fluoride ion) is not required, thereby eliminating impurity formation (such as compounds 29-1 and 29-2 shown below) due to possible side reactions that may occur due to the presence of the basic fluoride ion, and (ii) the costly use of pyridine and hydrofluoric acid is eliminated.

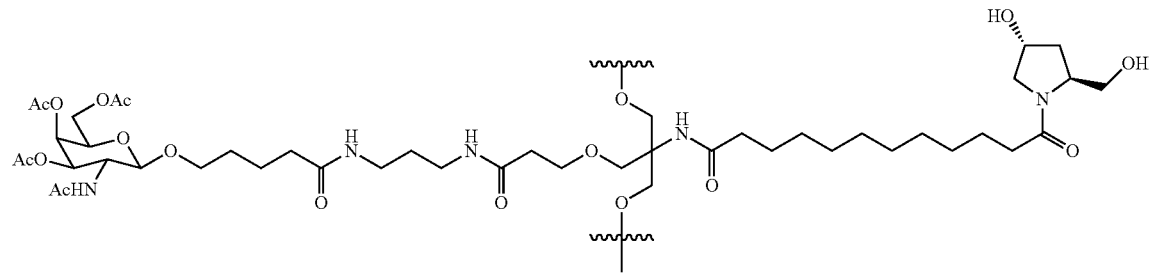

29-1

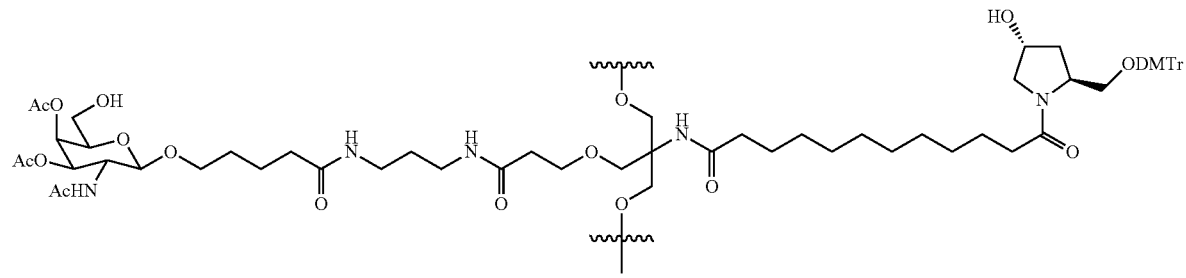

29-2

Conversion of Compound 29A to Compound 31
Compound 29A may be converted to Compound 31 via the sequence of reactions shown in Scheme 8 below.
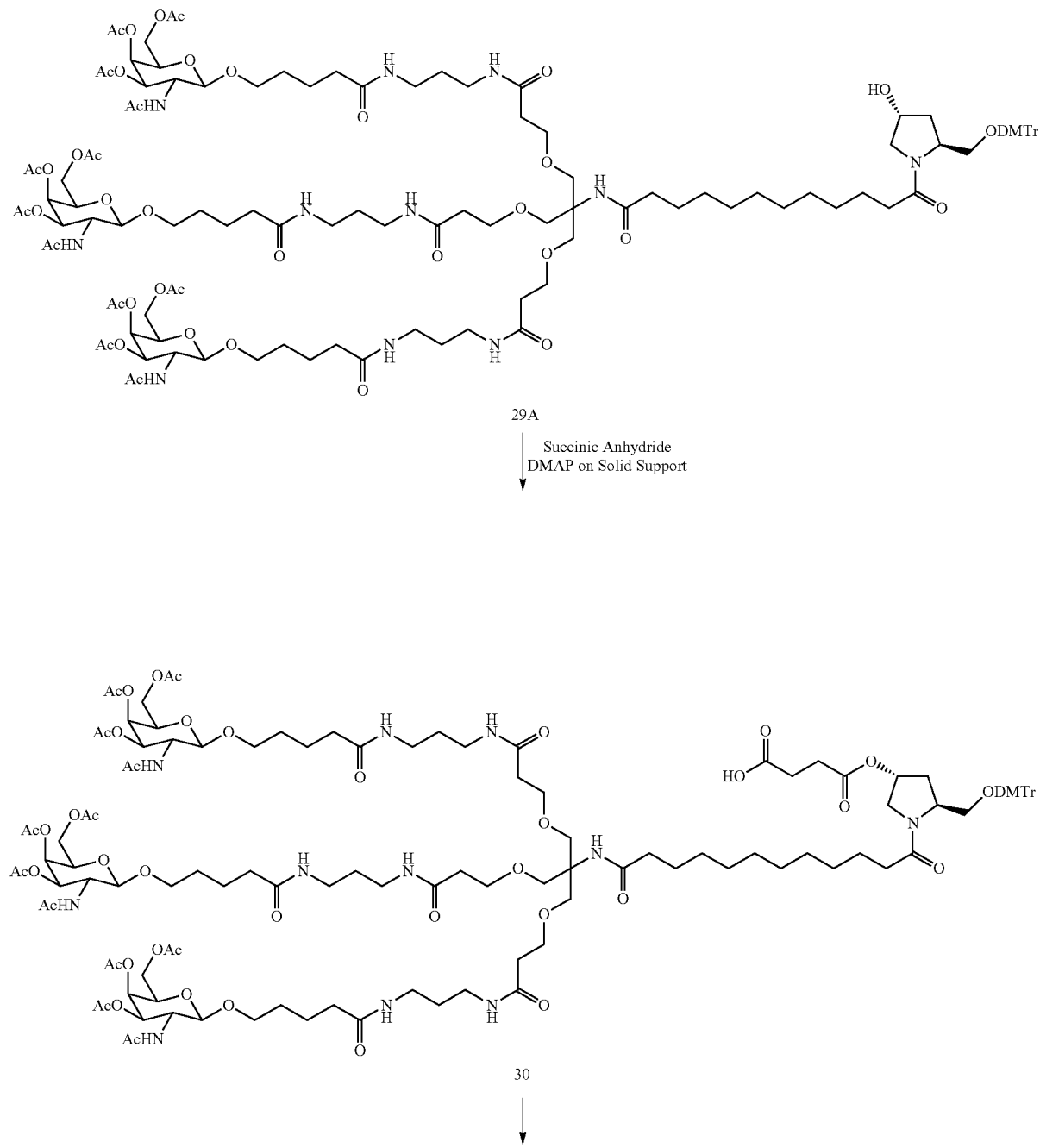

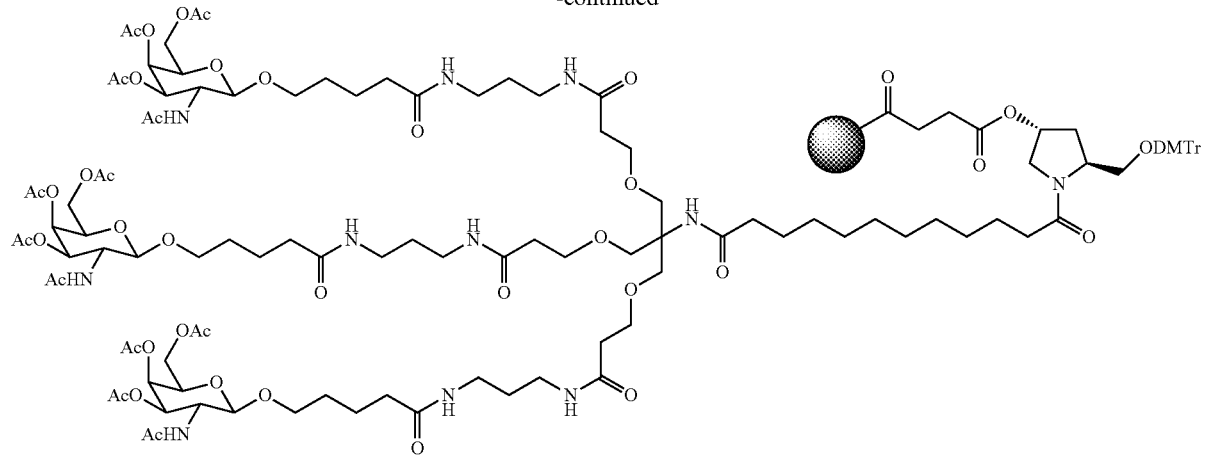

31

Reaction of compound 29A with succinic anhydride in the presence of a base (e.g., triethylamine) affords compound 30, which may be loaded onto a solid support to afford compound 31.

Advantages of the process shown in Scheme 8 include (i) the use of expensive catalysts typically used in this reaction such as DMAP (dimethylamino pyridine) or an immobilized DMAP (such as PS-DMAP, a polystyrene bound equivalent of DMAP) is eliminated, (ii) the number of potential impurities in the product (due to oligomerization reactions) is reduced, and (iii) the possibility of contamination by heavy metals (such as Pd or Ru when used as catalysts) is eliminated.

The invention is further illustrated by the following examples, which should not be construed as further limiting. The contents of all references, pending patent applications and published patents, cited throughout this application are hereby expressly incorporated by reference.

EXAMPLES

Experimental Procedure: GalNAc Process

Example 1

Synthesis of Compound 2

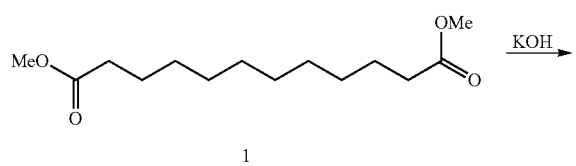

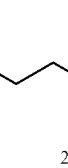

To a stirred solution of dimethyl ester 1 (200 g, 774.65 mmol) in diethylether and acetonitrile was added KOH (891.4 mmol) dissolved in MeOH dropwise at 0-5° C. over 1 hour and the reaction mixture was stirred at the same temperature for additional 48 hours. Filtered the white solid using sintered funnel followed by washing it with diethylether (100 mL) and suction dried for 3 hour. The above obtained white solid was dissolved in water (500 mL) followed by acidification with 1N HCl to pH ~3-4 and the white solid was collected by filtration followed by washing it with water (50 mL×2). This material was air dried for one day followed by drying in the presence of $P_2O_5$ gave the product 2 (166 g, 88%) as white powder.

Example 2

Synthesis of Compound 5

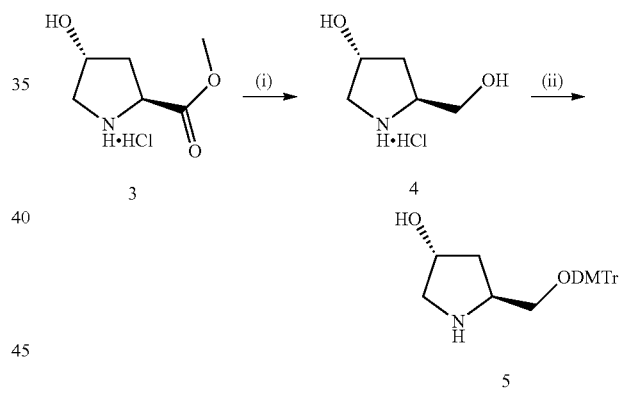

Reagents and conditions: (i)[1]. $Boc_2O$, $Et_3N$, DCM, (i)[2]. $LiBH_4$, THF and (i)[3]. HCl in ether. (H)[1] Ethyl trifluoroacetate, $Et_3N$; (ii)[2] DMTr-Cl/Py or DMTr-Cl, DMAP/Py and (ii)[3] aq. KOH Synthesis of Compound 4

Step (i)[1]: To a suspension of trans hydroxy proline methyl ester.HCL 3 (100 g, 552.3 mmol) and $Boc_2O$ (132.5 g, 607.57 mmol) in DCM (3 L) was added $Et_3N$ drop wise at ~0-5° C. over 1 hour and slowly brought to room temperature overnight. Water (50 mL) was added and concentrated the organic solvent followed by followed by concentration of the solvent gave the crude material (~115 g) which was used for the next step without purification. $^1H$ NMR ($CDCl_3$): 1.42, 1.46 (s, 9H), 1.75-1.77 (m, 2H), 2.07-2.11 (m, 1H), 2.26-2.34 (m, 1H), 3.44-3.67 (m, 3H), 3.74 (s, 3H), 4.4 (t, J=8.0 Hz, 1H), 4.48-4.51 (m, 1H).

Step (i)[2]: To a stirred solution of NBoc protected prolinol methyl ester (115 g, 469 mmol) in THF at ~0° C. was added $LiBH_4$ portion wise over one hour and the reaction mixture was stirred at room temperature for overnight. 50 mL of 1N NaOH solution was added and concentrated the solvent followed by extraction with DCM (2×500 mL), washing with water and brine. The organic layer was dried over Na$_2$SO$_4$. Concentration of the solvent gave crude diol (92 g) as colorless oil (92 g). $^1$H NMR (CDCl$_3$): 1.48 (s, 9H), 1.74 (br s, 1H), 2.02-2.08 (m, 1H), 2.63 (br s, 2H), 3.42-3.75 (m, 4H), 4.11-4.17 (m, 1H), 4.38-4.39 (m, 1H).

Step (i)[3]: To a stirred solution of NBoc diol (57 g, 262.52 mmol) in ether (150 mL) was added HCl in ether (50 mL) and stirred for overnight. The white solid was filtered and washed with ether (50 mL). The filtrate was kept at ~0° C. for 6 h and the solid was filtered and washed with ether (25 mL). Both batches were combined and dried in the presence of P$_2$O$_5$ under reduced pressure to constant weight 4 (31 g). $^1$H NMR (D$_2$O): 1.94-2.01 (m, 1H), 2.14-2.19 (m, 1H), 3.30-3.48 (m, 2H), 3.71-3.76 (m, 1H), 3.93-4.08 (m, 2H), 4.67-4.75 (m, 1H).

Synthesis of Compound 5

Step (ii)[1]: The reaction was performed in a 5 necked 15 L glass reactor fitted with an overhead stirrer over an ice bath. To a stirred solution of 4 (450 g, 2.94 mole) in acetonitrile (8 L) were added Et$_3$N (1 L, 7.2 mole) and ethyl trifluoroacetate (1000 g, 7.04 mole), and stirred at room temperature overnight. The white solid (Et$_3$N.HCl) was filtered over sintered funnel and washed with ethyl acetate (4 L). The organic solution was concentrated followed by co-evaporation with toluene (2 L×2) and dried under reduced pressure overnight in a 22 L rotary evaporator to obtain crude product as a gummy mass (~600 g).

Step (ii)[2]: Above obtained crude compound (2.94 mole) was dissolved in 2 L of anhyd. pyridine and transferred to the four necked 15 L flask. Another 6 L of anhyd. pyridine was added. This solution was cooled to ~5° C. using ice bath followed by addition of DMTr-Cl (1000 g, 2.95) portion wise under nitrogen atmosphere over 20 min. and the reaction mixture was stirred at room temperature overnight. 12 L of water was added while stirring and let it stand for 6 h. The compound was settled at the bottom of the flask as a brownish gummy mass. Water-pyridine layer was decanted using transfer pump and the aqueous layer was extracted with ethyl acetate (2×5 L). Combined the ethyl acetate extract with the viscous material remained in the reactor, after decanting water layer. Concentration of the solvent gave the corresponding product as viscous oil which was used for the next step without purification.

Step (ii)[3]: To a stirred solution of trifluoroacetyl compound (2.94 mole) in MeOH (5 L) was added KOH (330 g, 5.88 mole) dissolved in water (2 L) drop wise over 30 min. and stirred at room temperature for 1 h. Concentrated to 3 L volume followed by addition of 15 L of water and allowed to stand overnight. The product was settled at the bottom as reddish brown viscous oil. Decanted the water using transfer pump followed by addition of 6 L of DCM to dissolve, washed with 5 L of water and separated the organic solvent. Concentration of the solvent followed by silica gel column chromatography (4 Kg silica, eluent: hexane/ethyl acetate and ethyl acetate/MeOH) purification gave compound 5 (1000 g, 81%) as foamy yellowish white solid. $^1$H NMR (CDCl$_3$): 1.35-1.42 (m, 1H), 1.65-1.70 (m, 1H), 2.33 (br s, 1H), 2.59-2.62 (m, 1H), 2.72-2.75 (m, 1H), 2.82-2.91 (m, 2H), 3.36-3.41 (m, 1H), 3.71 (s, 6H), 4.1 (br s, 1H), 4.525 (d, J=4.0 Hz, 1H).

Example 3

Synthesis of Compound 31

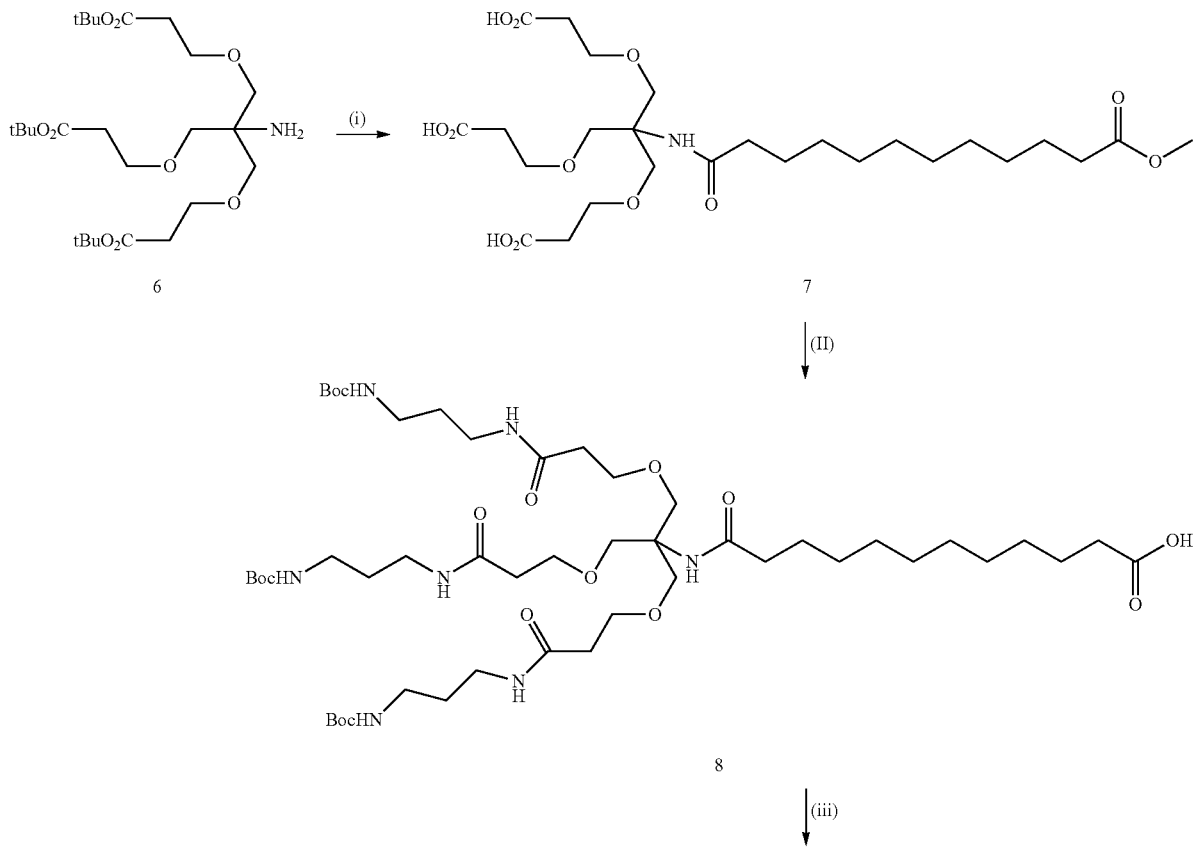

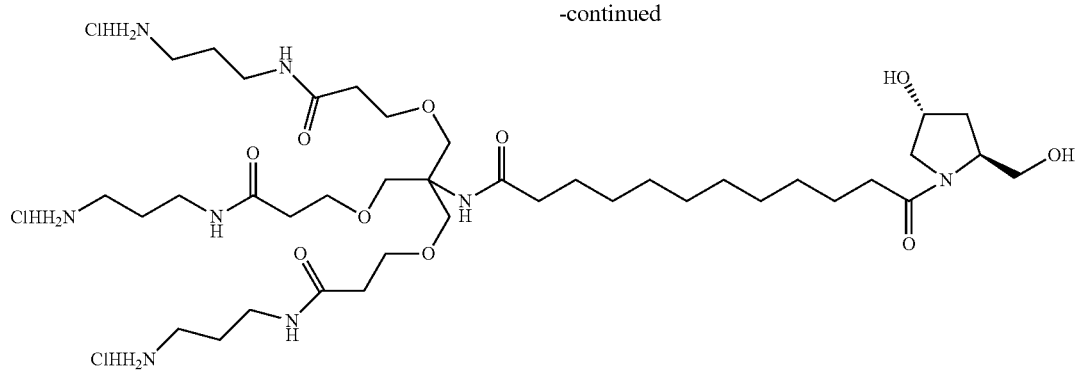

9

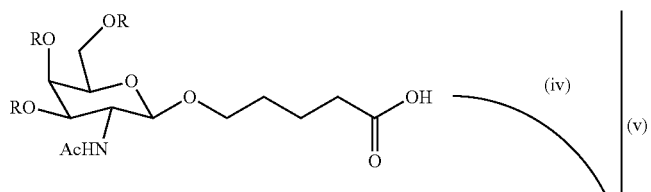

R = Ac or Bz

25

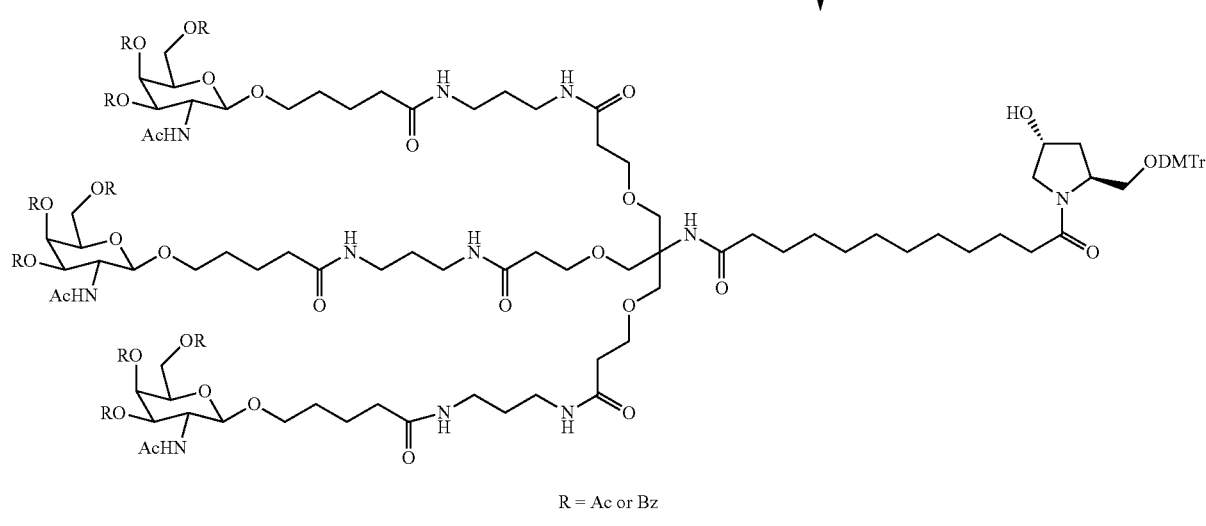

R = Ac or Bz

31

50

Reagents and conditions: (i)[1]. EDC.HCl, DIEA, HOBt/DCM-DMF or HBTU, DIEA/DCM-DMF or HBTU, DIEA, HOBt/DCM-DMF or EDC.HCl, DIEA, N-hydroxysuccinimide or EDC.HCl, DIEA, pentafluorophenol or DCC, DMAP/DCM-DMF or any other carboxylic acid activator for amidation/esterification and monomethyl dodecanedoic acid (i)[2] HCOOH or HCl in ether/dioxane/dioxane-DMF or TFA, (ii)[1]. step (i)[1] plus Mono Boc 1,3-propanediamine and (ii)[2] LiOH or NaOH or KOH in aq. THF; (iii)[1] step (i)[1] plus compound 5 and (iii)[2]. step (i)[2]; (iv) (i)[1] plus compound 9; (v) DMTr-Cl/Py or DMTr-Cl, DMAP/py.

Synthesis of Compound 7

Step (i)[1]: Commercially available compound 6 (1081 g, 2.139 mol), Dodecanoic acid monn methyl ester (653 g, 2.673 mole) and HOBt (433.5 g, 3.209 mol) were dissolved in a mixture of DCM (6 L) and DMF (1 L) in a 12 L 3 neck RB flask equipped with overhead stirrer under argon. The reaction mixture was cooled in an ice-water bath and maintained the temperature ~10° C. EDAC.HCl (531 g, 2.673 mol) was added slowly portion wise followed by DIEA (1.12 L, 6.42 mol) over period of 30 minutes. The reaction mixture kept stirring under argon for two days. TLC checked after two days using KMnO₄ stain and transferred to a rotavapor flask and removed the volatiles under reduced pressure. After removing most of the dichloromethane the flask transferred to a hood and added 15 L of water with stirring and kept mixture for settling overnight. The top layer was decanted and bottom viscous layer was dissolved in 4 L of EtOAc and washed with water (2×4 L), 10% aqueous citric acid (2×3.5 L), 2×4 L of aq. NaHCO₃ solution, followed by saturated brine (2.5 L). The organic layer was dried over sodium sulfate and removed the solvents. The crude product was dried under high vacuum overnight and used for the next reaction without any other purification (1641 g, quantitative). LC-MS, Cal. For $C_{38}H_{69}NO_{12}$ MW: 731.48. Found 732.3 (M+H). 1H NMR (400 MHz, DMSO) δ 6.85 (s, 1H), 3.53 (dd, J=12.9, 6.9 Hz, 16H), 3.30 (s, 1H), 2.49 (dd, J=3.5, 1.7 Hz, 2H), 2.37 (t, J=6.1 Hz, 7H), 2.26 (t, J=7.4 Hz, 2H), 2.02 (t, J=7.3 Hz, 2H), 1.56-1.44 (m, 3H), 1.44-1.34 (m, 32H), 1.21 (s, 13H).

Step (i)[2]: The above compound from Step (i)[1] (1560 g, 2.134 mole) was taken in 22 L 3 neck RB flask equipped with overhead stirrer under argon. Formic acid (10 Kg) was added to acid and stirred the mixture for 24 hrs. TLC showed small amount of starting material remained. More formic acid (4 L) was added and continued the stirring for another 24 hrs. TLC and mass spectra showed completion of reaction and the mixture transferred to 20 L rotary evaporator and removed the volatiles under reduced pressure. After the removal of formic acid the residue was co-evaporated with toluene (4.5 L×2). To the above residue 8 L of 50% EtOAc/hexane was added with slow rotation, white solid precipitated from the solution and the mixture stirred for 2 hrs. The mixture was filtered and washed with 4 L of 50% EtOAc/hexane followed by 4 L of anhydrous ether. The compound 7 was air dried at 45° C. until it reaches constant weight (Yield 1096 g, 91%). LC-MS Cal. for $C_{26}H_{45}NO_{12}$ MW: 563.29. Found 564.3 (M+H). $^1$H NMR (400 MHz, DMSO) δ 12.08 (bs, 3H), 6.89 (s, 1H), 3.65-3.43 (m, 7H), 2.41 (dt, J=12.7, 6.3 Hz, 3H), 2.26 (t, J=7.4 Hz, 1H), 2.02 (t, J=7.3 Hz, 1H), 1.44 (ddd, J=19.5, 13.3, 6.7 Hz, 2H), 1.21 (s, 5H).

Synthesis of Compound 8

Step (ii)[1]: To a stirred solution of 7 (89.5 g, 158.7), NBoc propane diamine (103.6 g, 595 mmol), EDC (113.7 g, 595 mmol), HOBt (96.4 g, 630 mmol) in DCM/DMF (1.5 L/0.5 L) was added DIEA (207.4 mL, 1190 mmol) drop wise over 10 min. and stirred at room temperature for 14 h. 100 mL water was added and evaporated DCM under reduced pressure. Another 1 L of water was added followed by decanted the water layer carefully and this procedure was repeated twice. The obtained viscous oil was dissolved in DCM (500 mL) followed by washing with water (500 mL), 10% citric acid (500 mL), sat. NaHCO$_3$ (250 mL), brine (200 mL) and dried over Na$_2$SO$_4$. Concentration of the solvent gave the corresponding product (157 g) as colorless viscous oil. LCMS: Calculated: 1031.67 (M$^+$). Found: 1066.4 (M$^+$+Cl$^-$).

Step (ii)[2]: To a stirred solution of methyl ester (135 g, 131 mmol) in 1.5 L of THF was added aq. LiOH (13 g in 0.5 L of water, 309.5 mmol) and stirred at room temperature for 14 h. The solvent was evaporated to ~1 L followed by 2 L of water was added. This aqueous solution was washed with ethyl acetate (1 L×2) followed by the pH was adjusted to 2-3 with 20% citric acid, extracted with DCM (1 L×2), washed with brine, dried over Na$_2$SO$_4$ and concentration of the solvent gave 8 (107 g) as colorless viscous oil. LCMS for compound 8: Calculated: 1017.66 (M$^+$). Found: 1016.6 (M$^+$−1).

Synthesis of Compound 9

Step (iii)[1]: To a stirred solution of acid 8 (28 g, 27.514 mmol) trans hydroxyl prolinol 4 (6.3 g, 41.27 mmol) and HOBt (16.84 g, 110.06 mmol) in DCM/DMF (250 mL/250 mL) was added DIEA (17.75 g, 137.57 mmol) drop wise at room temperature over 5 min. and stirred for 30 min. To the above solution was added HBTU (13.05, 34.39 mmol) portion wise over 10 min. and stirred for 3 h. 100 mL of water was added followed by evaporation of DCM and then 500 mL of water was added and left at standing for 1 h. Decanted the turbid solution and the sticky solid was ringed with water (100 mL×3). The gummy material was dissolved 20% MeOH in DCM (500 mL) and concentrated followed by co-evaporation with toluene (100 ml x 2) to obtain the corresponding product (31 g) as yellowish foamy solid. LCMS: Calculated: 1116.73 (M$^+$). Found: 1117.7 (M$^+$+1), 1139.6 (M$^+$+Na).

Step (iii)[2]: To a stirred solution of the above compound (29 g, 25.9 mmol) in 150 mL of MeOH was added 2M HCl in diethyl ether drop wise over 10 min. and stirred for 3 h. 300 mL of anhydrous diethyl ether was added and left it stands for 30 min. The organic solvent was decanted, washed with diethyl ether (200 mL×2). Dried the gummy material under reduce pressure to get white powder 9 (23.2 g). LCMS for compound 9: Calculated: 816.57 (M$^+$). Found: 817.4 (M$^+$+1), 839.3 (M$^+$+Na).

Alternate Methods for Step(iii)[2]:
(A) The above NBoc compound (0.475 g, 0.425 mmol) was dissolved in 10 mL of 95% HCOOH and stirred for 3 h. The organic solvent was concentrated to yield the corresponding product in quantitative yield. LCMS for compound 9: Calculated: 816.57 (M$^+$). Found: 817.4 (M$^+$+1), 839.3 (M$^+$+Na).
(B) The above NBoc compound (0.475 g, 0.425 mmol) was dissolved in 10 mL of 20% TFA in DCM and stirred for 3 h. The organic solvent was concentrated to yield the corresponding product in quantitative yield. LCMS for compound 9: Calculated: 816.57 (M$^+$). Found: 817.4 (M$^+$+1), 839.3 (M$^+$+Na).

Synthesis of Compound 31

Step (iv): To a stirred solution of 25 (10 g, 15.79), EDC (3.79 g, 19.84 mmol), N-hyroxy succinimide (2.27 g, 19.73 mmol) in DCM (200 mL) was added DIEA (5.09 g, 39.46 mmol) drop wise over 5 min. and stirred at room temperature for 14 h. 50 mL water was added followed by extraction with DCM (2×100 mL), washed with water, 10% citric acid (100 mL), sat. NaHCO$_3$ (250 mL), brine (200 mL) and dried over Na$_2$SO$_4$. Concentration of the solvent gave the corresponding product (12 g) as yellowish solid and used for the next step without purification.

To a stirred solution of the amine 9 (22 g, 23.8 mmol) in DMF (500 mL) were added Et$_3$N drop wise and NHS-sugar (55.6 g, 76.16 mmol, obtained from above step) in one shot and the reaction mixture was stirred at room temperature for overnight (12 h). 1 L of water was added into the reaction mixture and left at standing for 1 h. The turbid water/DMF solution was decanted, ringed with water (100 mL×2). The gummy material was dissolved in DCM (~500 mL), dried over Na$_2$SO$_4$. Concentration of the solvent gave the crude material, which was purified by column chromatography (0-20% MeOH in DCM) to obtain the corresponding product (27.5 g, 48%). MALDI: Calculated: 2662.20 (M$^+$). Found: 2686.08 (M$^+$+Na), 2702.74 (M$^+$+K).

Step (v): To a stirred solution of alcohol (420 mg, 0.158 mmol) in dry pyridine (10 mL) were added DMTrCl (64 mg, 0.19 mmol) and DMAP (10 mg, 0.08 mmol). This reaction mixture was stirred at room temperature overnight. Another 107 mg (0.32 mmol) of DMTrCl was added and stirred for 6 h. The reaction was quenched with water (10 mL) followed by concentration to 10 mL volume. Decanted the water layer and the gummy material was ringed with 10 mL water twice. This material was dissolved in DCM (10 mL), dried over Na$_2$SO$_4$ and concentration of the solvent gave the crude material which was purified by column chromatography to obtain 11 (250 mg, yield 74%). MALDI for compound 11: Calculated: 2964.33 (M$^+$). Found: 2988.85 (M$^+$+Na), 3002.77 (M$^+$+K).

Example 4
Synthesis of Monocarboxylic Acid 30
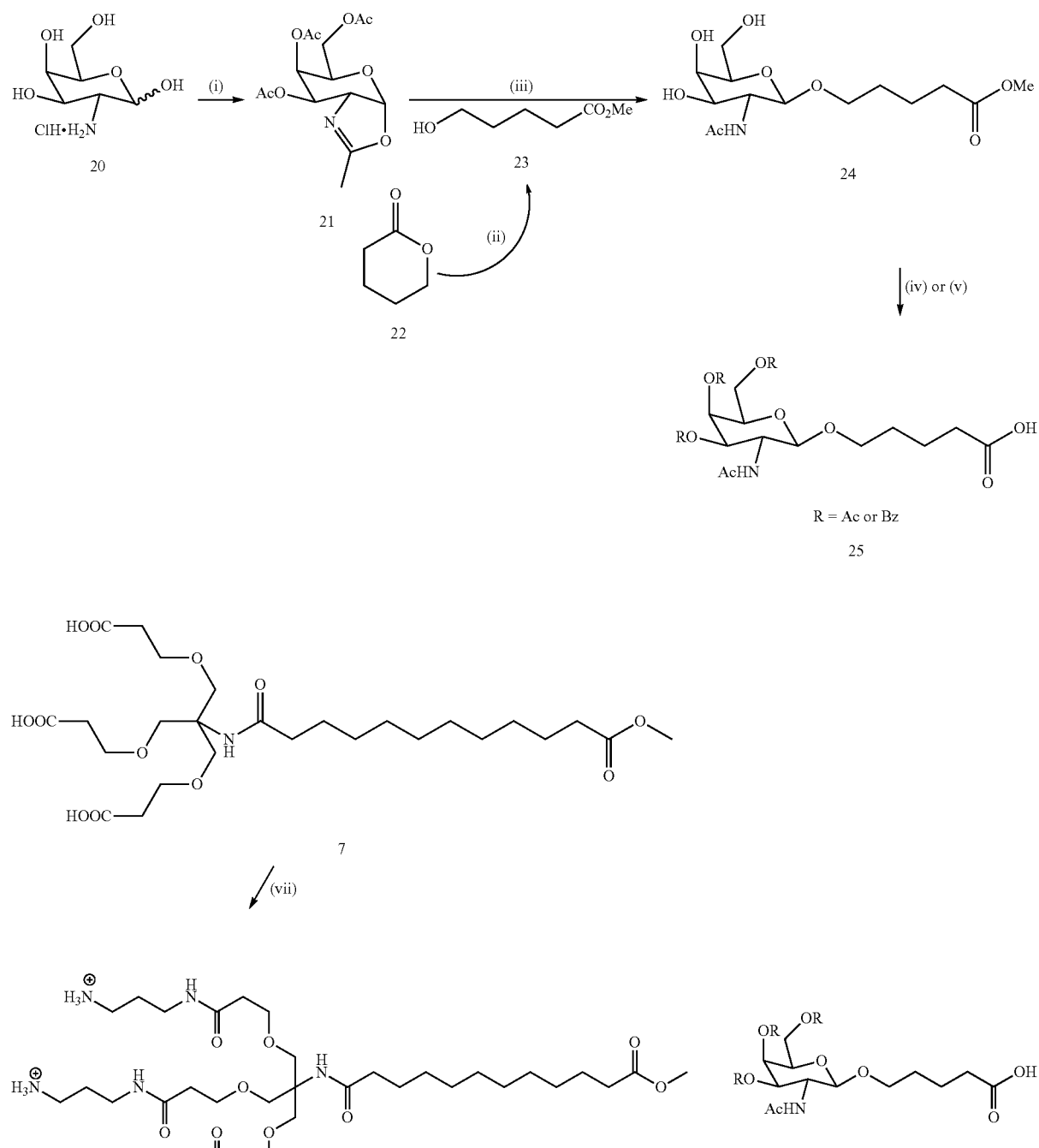
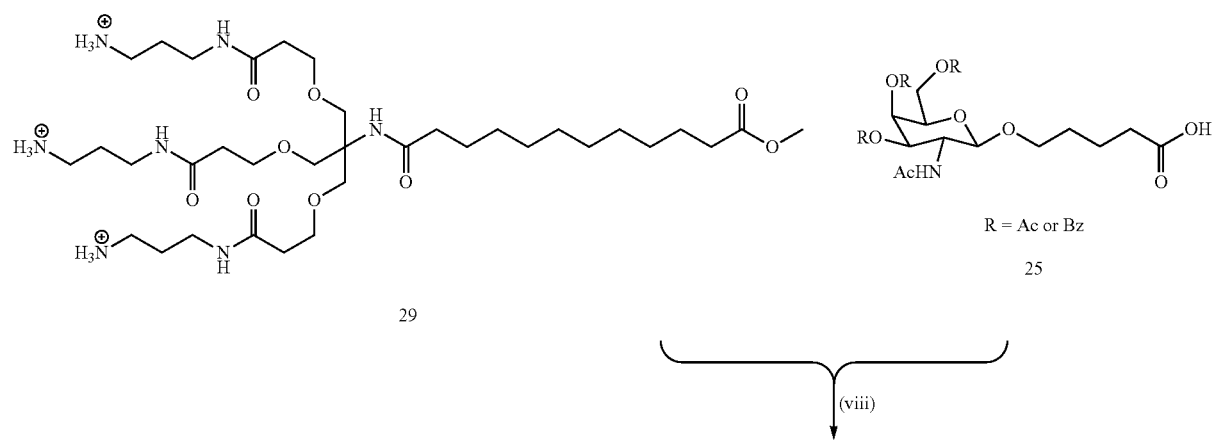

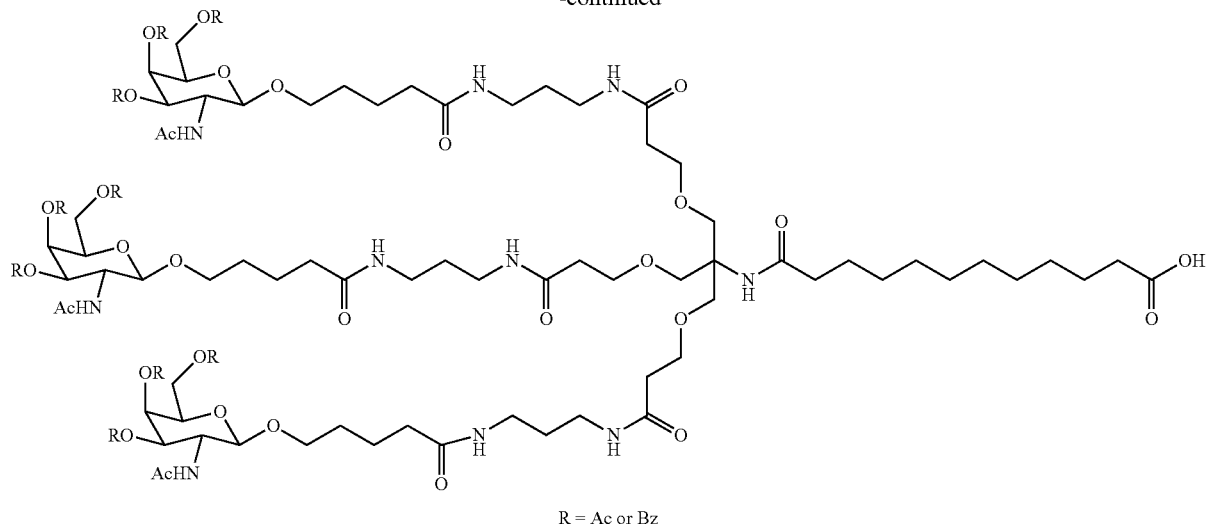

R = Ac or Bz

30

Reagents and conditions: (i)[1]. Ac₂O, DMAP, ET₃N/Py and (i)[2]. TMSOTf/1,2-dichloroethane; (ii) MeOH, Et₃N; (iii)[1]. TMSOTf/1,2-dichloroethane and (iii)[2]. ET₃N/MeOH; (iv)[1]. Bz₂O, DMAP/Py and (iv)[2]. LiI/Py, reflux for R=Bz; (v)[1]. Aq. NaOH and (v)[2]. Ac₂O, DMAP/Py for R=Ac; (vii)[1]. EDC.HCl, DIEA, HOBt/DCM-DMF or HBTU, DIEA/DCM-DMF or HBTU, DIEA, HOBt/DCM-DMF or EDC.HCl, DIEA, N-hydroxysuccinimide or EDC.HCl, DIEA, pentafluorophenol or DCC, DMAP/DCM-DMF or any other carboxylic acid activator for amidation/esterification and Mono Boc 1,3-propanediamine (vii)[2]. TFA, anisole, rt; or HCl/MeOH/Doxane or p-Toluene sulfonic acid/MeOH at 60-70° C. (viii)[1]. step (vii)[1], [2]. NaOMe/MeOH, (viii)[3]. Aq. NaOH and (viii)[4]. Ac₂O/Py.

Synthesis of Compound 21

Step (i)[1]: Anhydrous pyridine (7.2 L) was added to a stirred and cooled (over ice bath) suspension of galactosamine.HCl 20 (1.63 kg, 7.55 mol) in acetic anhydride (5.3 L) in 40 L reactor under Ar atmosphere. DMAP (79 g), and triethylamine (1.05 L, 7.55 mol) were added consecutively, and the mixture was stirred over the ice bath overnight during which time dissolution of 20 followed by crystallization of peracetylated sugar and triethylamine hydrochloride occurred along with exothermic effect up to 30° C. for the first 2 hours. The mixture was filtered through a sintered glass filter, and the residue was washed with toluene (~4 L×2) followed by water (~3 L×2). The crystalline residue was dried overnight on the glass filter, transferred to drying dishes and dried on air at 70° C. on a hot plate for two days to afford 2.53 kg (86%) of pure compound peracetylated compound.

Step (i)[2]: The reaction was performed in a 20 L reactor under Ar atmosphere. TMSOTf (1.40 L, 7.74 mol) was added slowly (10 min) to a stirred suspension of the peracetylated sugar intermediate (2.52 kg, 6.49 mol) in anhyd. DCE (4.0 L) under Ar atmosphere. The mixture was stirred at rt overnight and transferred via transfer line to a vigorously stirred mixture of NaHCO₃ (1.64 kg, 19.4 mol), ice (5.5 L) and water (5.5 L) in an open 40 L reactor. The stirring was continued for 40 min, the organic layer was separated, the water layer was washed with DCM (×2), and the combined organic extracts were dried over anhyd. Na₂SO₄. The mixture was filtered, the solvent was evaporated, oily residue was dried on rotary evaporator (15 mbar at 30° C.), redissolved in anhyd. DCE (4.0 L), and the solvent was evaporated again, and dried on rotary evaporator (3 mbar at 30° C. bath temperature) to afford 2.14 kg of crude 21. The crude compound in the rotary evaporator was redissolved in anhyd. DCE (4.0 L) and the resulting solution was used in the next step.

Synthesis of Hydroxy Acid 23

The reaction was performed in a 20 L rotary evaporation flask under slow flow of argon. A solution of valerolactone 22 (98% purity (TCI), 1.0 kg, 10 mol) and triethylamine (140 mL, 1 mol) in dry methanol (4 L) was stirred at rt for 1 h, during which time slight exothermic effect (up to 28° C.) was observed. The mixture was concentrated in vacuum (25° C. heating bath), diluted with dry toluene (4 L), and evaporated under the reduced pressure, and the residue was dried on rotary evaporator at 4 mbar/25° C. followed by stirring under high vacuum (0.4-0.6 torr, rt) overnight to afford 23 as a colorless liquid, 1.39 kg (100%), containing <1% of toluene.

Synthesis of Compound 24

Step (iii)[1]: The reaction was performed in a 20 L reactor fitted with a cooling jacket under Ar atmosphere. TMSOTf (250 mL, 1.38 mol) was added to a stirred and cooled (12° C.) solution of crude 21 (2.14 kg, ≤6.49 mol) and hydroxyester 23 (0.94 L, 7.14 mol) in anhyd. DCE (6.5 L). Immediate exothermic effect (up to 23° C.) observed, the cooler was turned off, and the mixture was stirred at rt for 3 h and transferred to a 22 L open flask with a vigorously stirred mixture of NaHCO₃ (168 g, 2.0 mol), water (3 L), and some ice. The organic phase was separated, dried over anhyd. Na₂SO₄, the solvent was evaporated, and oily residue was dried on rotary evaporator at 12 mbar/30° C. to afford 3.09 kg of crude product that was used in the next step without further purification.

Step (iii)[2]: The reaction was performed in a 20 L filtration reactor fitted with a heating/cooling jacket. Crude product obtained from previous step (3.09 kg, ≤6.49 mol) was dissolved in anhydrous methanol (10 L) under Ar atmosphere, and triethylamine (0.90 L, 6.49 mol) was added. The mixture was heated at 50° C. for 2 days, and toluene (4 L) was added and the solution was allowed to cool to rt overnight during which time bulk crystallization occurred. The slurry was cooled to 0° C., stirred overnight, filtered, and the solid was washed with 10% methanol in toluene (8.8 L) and dried on air at 65° C. over a hot plate to afford 0.97 kg of 24. Filtrate was concentrated in vacuum till bulk crystallization, and dry ethyl alcohol (4.0 L) was added. The slurry was triturated on rotary evaporator at rt overnight, filtered, and the solid was washed with toluene-ethanol mixture (1:1, ~2 L) to afford additional 191 g of 24 after drying on air at 65° C. over a hot plate. Total yield: 1.16 kg, 54% based on 9, ~95% purity.

Synthesis of Compound 25 (R=Bz)

Step (iv)[1]: Compound 24 (1.06 kg, 3.15 mol, ~95% purity) and DMAP (384 g, 3.15 mol) were dissolved in anhydrous pyridine (9.0 L) under Ar atmosphere. Benzoic anhydride (2.49 kg, 11.02 mol) was added, the mixture was stirred overnight, water (200 mL) was added, and the stirring was continued for additional 0.5 h. Pyridine was evaporated, and the residue was dried on rotary evaporator at 10 mbar over 35° C. bath temperature (crystallization occurred). The residue was partitioned between water (2 L) and EtOAc (4 L) in rotary evaporator flask till complete dissolution of solids, transferred to an extraction vessel, and diluted with additional EtOAc (8 L) and water (5 L). The organic layer was separated and washed consecutively with water (10 L), sat. NaHCO$_3$ (5 L×2), and again water (5 L×2). The organic layer was separated, the solvent was evaporated in vacuum till viscous mass, the oily residue was redissolved in ethanol (3.8 L), the solvent was evaporated again, and the residue was dried on rotary evaporator at 20 mbar/35° C. The residue was redissolved in ethanol (10.6 L) at 35° C. and transferred to a 20 L filtration reactor fitted with heating/cooling jacket. Water (6.0 L) was added portion wise, and the mixture was allowed to cool down to 22° C., and seeds of the product were added. Bulk crystallization occurred after stirring overnight; the mixture was cooled to 0° C., stirred for additional 5 h, and filtered. The precipitate was pre-dried by passing air overnight, transferred to drying dishes, and dried on air at 65° C. over hotplates for 2 days (till constant mass) to afford 1.70 kg (84%) of the benzoylated product (~97% purity).

Step (iv)[2]: A mixture of the perbonzoylated product obtained (608 g, 0.938 mol), anhyd. LiI ("ultra dry"—Alfa-Aesar, 503 g, 3.75 mol), and anhyd. pyridine (1.6 L) was heated under Ar atmosphere, gentle reflux, for 24 h, cooled to rt, and diluted with water (0.5 L). Pyridine was evaporated, the oily residue was dried on rotary evaporator at 4 mbar/30° C., and partitioned between chilled 20% H$_3$PO$_4$ (5 L) and ethylacetate-hexane mixture (2:1, 5 L). The organic phase was separated, washed with 5% aq. NaCl (2 L), 3% aq. sodium bisulfite (2 L), and dried over anhyd. Na$_2$SO$_4$. The solution (total volume 6 L) was decanted form the drying agent and filtered through wet-loaded in ethylacetate-hexane mixture (2:1) plug of 900 g silica gel on a sintered glass filter funnel. The silica gel cake was washed with AcOEt-hexane 2:1 mixture, until no substantial amount of acid in the filtrate was observed by TLC (18 L). The combined filtrates were evaporated, the foamy product was dissolved in ACN (1.6 L), and the ACN was evaporated. The last procedure was repeated, and the product was dried at 0.4 torr for 1 day to afford 25 (584.3 g, 98%). $^1$H NMR (400 MHz, DMSO-d6): δ 1.54 (S, 4H), 1.71 (S, 3H), 2.22 (t, 2H), 3.54 (m, 1H), 3.81 (m, 1H), 4.39 (m, 2H), 4.48 (m, 2H), 4.74 (d, 1H), 5.37 (dd, 1H), 5.76 (d, 1H), 7.40 (t, 2H), 7.50 (t, 2H), 7.58 (m, 3H), 7.65 (t, 1H), 7.73 (m, 3H), 7.92 (t, 4H), 8.11 (d, 2H), 12.11 (s, 1H). $^{13}$C NMR (100 MHz, DMSO-d6): δ 21.0, 22.6, 28.3, 33.2, 49.7, 62.0, 67.9, 68.4, 70.0, 71.8, 100.8, 128.5, 128.6, 128.9, 129.0, 129.1, 133.4, 133.6, 164.8, 165.1, 169.3, 174.3. LC-MS: 634 (M+1)+.

Synthesis of Compound 25 (R=Ac)

Step (v)[1]: Compound 24 (12.70 g, 38 mmol) was dissolved in a solution of NaOH (1.88 g, 47 mmol) in methanol (50 mL) and water (5 mL), the mixture was stirred overnight, neutralized with acetic acid (0.51 mL, 9 mmol), diluted with anhydrous ethanol (200 mL) and evaporated to dry. After drying overnight at 0.4 torr, 15.38 g of white foam was obtained that was triturated with 150 mL of anhydrous pyridine followed by acetic anhydride (30 mL, 152 mmol). The mixture was stirred at 30° C. overnight, cooled to 0° C., and water (14 mL) was added. Cooling bath was removed, the mixture was stirred at rt for 1 h, most of the solvents were removed in vacuum, the residue was partitioned between saturated brine (150 mL) and ethylacetate (100 mL), the organic layer was separated, washed with a mixture of 20% phosphoric acid and 20% brine (1:1, 250 mL), saturated brine 3 times, dried over anhyd sodium sulfate, and evaporated in vacuum. The residue was co-evaporated with n-butanol (×3) followed by ACN (×3) to afford 14.46 g (83%) of 25. $^1$H NMR (400 MHz, DMSO-d6): δ 1.54 (S, 4H), 1.71 (S, 3H), 2.22 (t, 2H), 3.54 (m, 1H), 3.81 (m, 1H), 4.39 (m, 2H), 4.48 (m, 2H), 4.74 (d, 1H), 5.37 (dd, 1H), 5.76 (d, 1H), 7.40 (t, 2H), 7.50 (t, 2H), 7.58 (m, 3H), 7.65 (t, 1H), 7.73 (m, 3H), 7.92 (t, 4H), 8.11 (d, 2H), 12.11 (s, 1H). $^{13}$C NMR (100 MHz, DMSO-d6): δ 21.0, 22.6, 28.3, 33.2, 49.7, 62.0, 67.9, 68.4, 70.0, 71.8, 100.8, 128.5, 128.6, 128.9, 129.0, 129.1, 133.4, 133.6, 164.8, 165.1, 169.3, 174.3. LC-MS: 634 (M+1)+.

Synthesis of Compound 29

Step (vii)[1]: Compound 7 (1090 g, 1.936 mol) and HOBt (1170 g, 8.667 mol) were taken in a 22 L flask equipped with overhead stirrer under argon. 4 L of DCM and 2 L of DMF were added with stirring and cooled the mixture in an ice-water mixture to ~10° C. A solution of mono boc propyl amine 21 (1265 g, 7.260 mol) in 2 L of DCM was added to the above solution with stirring. Slowly all the reagents went in to solution. A slurry of EDAC. HCl (1439 g, 7.260 mol) in 4 L of DCM was slowly added to the reaction mixture while maintaining the temperature around 10° C. DIEA (2.40 L, 13.55 mol) was added slowly over a period of 1.5 hr. The reaction mixture kept stirring overnight under argon. TLC checked and the reaction mixture was transferred to a rotary evaporator funnel and removed the volatiles under reduced pressure. The flask was transferred to the hood and added 10 L of water to the residue with stirring and left the mixture for settling overnight. Two layers were separated overnight and decanted the top layer. The bottom layer dissolved in 8 L of EtOAc and transferred to a separatory funnel and washed with water (2×4 L), aq. NaHCO$_3$ solution (2.5 L) and 10% aq. Citric acid (2×3.5 L) and water (1×4 L) and saturated brine (2.5 L). The organic layer was dried over sodium sulfate and removed the solvents under reduced pressure. The residue was co-evaporated with toluene and dichloromethane and dried under high vacuum (Yield 2026 g, quantitative). LC-MS Cal. for $C_{50}H_{93}N_7O_{15}$ MW: 1031.67. Found 1032.6 (M+H). 1H NMR (400 MHz, DMSO) δ 7.79 (t, J=5.6 Hz, 1H), 6.94 (s, 1H), 6.72 (t, J=5.3 Hz, 1H), 3.61-3.45 (m, 5H), 3.01 (dd, J=12.8, 6.6 Hz, 2H), 2.89 (dd, J=12.7, 6.5 Hz, 2H), 2.26 (t, J=6.3 Hz, 3H), 2.03 (t, J=7.3 Hz, 1H), 1.55-1.38 (m, 3H), 1.36 (d, J=10.7 Hz, 8H), 1.21 (s, 3H).

Step (vii)[2]: The compound from step (vii)[1] (52 g, 50.40 mmol) was dissolved in 100 mL of DCM with 20 mL of anisole. To the above mixture TFA (200 mL) was added and stirred the mixture overnight. Solvents were removed and the residue co-evaporated with toluene (2×100 mL) to get a gummy liquid. This residue was dissolved in MeOH (30 mL) and precipitated with anhydrous ether. The mixture kept in the cold room overnight to settle and decanted. Compound was dried under high vacuum to get a white fluffy solid 29 as its TFA salt (yield 52.10 g, 96%). LC-MS Cal. for $C_{35}H_{69}N_7O_9$ MW: 731.52. Found 732.50 (M+H). 1H NMR (400 MHz, DMSO) δ 8.04 (t, J=5.6 Hz, 1H), 7.82 (s, 3H), 3.65-3.42 (m, 5H), 3.18-3.02 (m, 2H), 2.84-2.69 (m, 2H), 2.28 (dt, J=12.2, 6.9 Hz, 2H), 2.03 (t, J=7.3 Hz, 1H), 1.78-1.57 (m, 2H), 1.56-1.35 (m, 1H), 1.21 (s, 3H).

Synthesis of Compound 30 (R=Ac)

Step (viii)[1] for Acetate: To a solution of GalNAc acid 25-Ac (50.65 g, 113.27 mmol), HBTU (52 g, 136 mmol) and HOBt (19 g, 135 mmol) in DCM (500 mL) was added DIEA (52 ml, 10 eq.) and stirred the mixture for 10 minutes at 15° C. To this mixture a solution of amine 29 (32 g, 29.80 mmol) in DMF (100 mL) was added stirred the mixture for 4 hrs. TLC checked and the solvents were removed. To the residue water was added and extracted with EtOAc. Washed the organic layer with water (2×200 mL), Aq. Bicarbonate solution (1×200 mL) and brine (200 mL), the organic layer was dried over sodium sulfate and removed the solvents. The crude product was purified by a short silica gel column using EtOAc/MeOH mixture as eluent to get the compound as an off white solid 26a (yield, 42.3 g, 70%). MALDI-MS Cal. for $C_{92}H_{150}N_{10}O_{39}$ MW: 2019.01. Found 2042.10 (M+Na).

Step (viii)[1] for Benzoate:
Method A: To a solution of GalNAc acid 25-Bz (35.86 g, 56.63 mmol), HBTU (28 g, 73.61 mmol) and HOBt (11.48 g, 84.90 mmol) in DCM (200 mL) was added DIEA (26 ml, 10 eq.) and stirred the mixture for 10 minutes at 15° C. To this mixture a solution of amine 29 (15.70 g, 14.90 mmol) in DMF (50 mL) was added stirred the mixture for 4 hrs. TLC checked and the solvents were removed. To the residue water was added and extracted with EtOAc. Washed the organic layer with water (2×100 mL), Aq. Bicarbonate solution (1×100 mL) and brine (150 mL), the organic layer was dried over sodium sulfate and removed the solvents. The crude product was purified by a short silica gel column using EtOAc/MeOH mixture as eluent to get the compound as an off white solid 26b (yield, 25.20 g, 67%). MALDI-MS Cal. for $C_{137}H_{168}N_{10}O_{39}$ MW: 2577.15. Found 3000.10 (M+Na). 1H NMR (400 MHz, DMSO) δ 8.04-7.80 (m, 1H), 7.79-7.33 (m, 2H), 6.96 (s, 1H), 5.74 (d, J=3.3 Hz, 1H), 5.36 (dd, J=11.1, 3.3 Hz, 1H), 4.73 (d, J=8.5 Hz, 1H), 4.55-4.19 (m, 1H), 4.01 (q, J=7.1 Hz, 1H), 3.86-3.73 (m, 1H), 3.64-3.45 (m, 1H), 3.31 (s, 1H), 3.02 (d, J=5.0 Hz, 1H), 2.36-2.15 (m, 1H), 2.13-1.99 (m, 1H), 1.69 (s, 1H), 1.61-1.35 (m, 1H), 1.31-1.02 (m, 1H).

Method B: To a solution of GalNAc acid 25-Bz (30.78, 48.62 mmol), EDAC.HCl (10.70 g, 54 mmol) and HOBt (9.11 g, 67.5 mmol) in DCM/DMF (2:1) (200 mL) was added DIEA (24 ml, 10 eq.) and stirred the mixture for 15 minutes at 15° C. To this mixture a solution of amine 29 A (14.50 g, 13.50 mmol) in DMF (100 mL) was added stirred the mixture overnight. TLC checked and the solvents were removed. To the residue water was added and the compound precipitated out. The precipitated residue dissolved in the EtOAc and washed the organic layer with water (2×200 mL), Aq. Bicarbonate solution (1×200 mL), 5% phosphoric acid (1×200 mL) and brine (150 mL), the organic layer was dried over sodium sulfate and removed the solvents. The crude product was purified by a short silica gel column using EtOAc/MeOH mixture as eluent to get the compound as an off white solid 26b (yield, 30.10 g, 87%). MALDI-MS Cal. for $C_{137}H_{168}N_{10}O_{39}$ MW: 2577.15. Found 3000.10 (M+Na).

Step (viii)[2-4]:
Triantennary GalNAc acid 30 from ester 26a

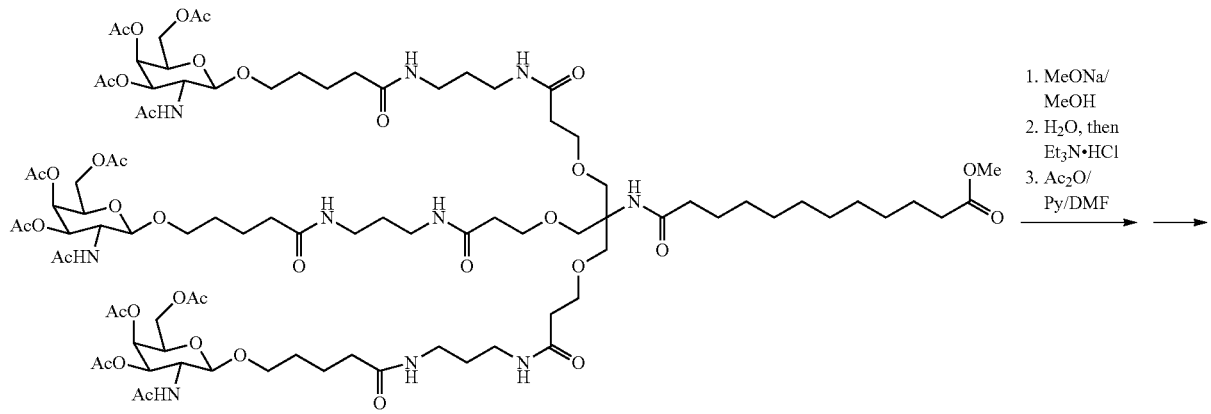

26a

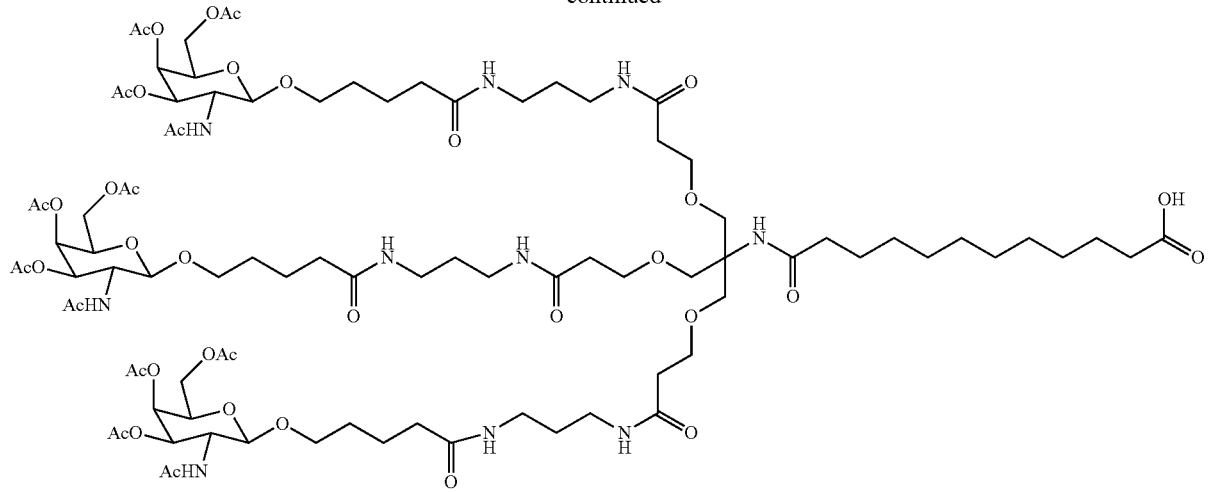

30

To a solution of triantennary ester 26a (10.2 g, 5 mmol) in anhydrous methanol (20 mL) at 0° C. was added 25 wt % solution of NaOMe (5.7 mL, 25 mmol) under Ar atmosphere. The mixture was stirred for 5 min and evaporated in vacuum till viscous oily residue that was re-dissolved in 15 mL of methanol and 2 mL of water. The mixture was stirred at rt overnight, neutralized with triethylamine hydrochloride (3.44 g, 25 mmol), and diluted with anhydrous pyridine (60 mL). The solvents were evaporated till viscous oily residue that was redissolved in anhyd. DMF (30 mL) under Ar atmosphere and the solution was transferred via cannula to a vigorously stirred mixture of pyridine (32 mL) and acetic anhydride (18.9 mL, 200 mmol). The mixture was stirred at rt overnight, cooled to 0° C., and water (11 mL) was added. The mixture was stirred at rt for 0.5 h, and evaporated at 45° C. till viscous oily residue. The residue was coevaporated with water (10 mL×2) followed by n-butanol (100 mL×2) to afford 15.0 g of residue. The latter was dissolved in ethyl acetate-isopropanol (5:1, 150 mL), and loaded on a filtration column with silicagel (45 g) deactivated with 2% TEA in ethylacetate. The filtration column was eluted with 150 mL each: ethyl acetate-isopropanol (5:1, ×2), ethyl acetate-methanol (5:1, ×2), (2:1, ×2), and (1:1, ×2). Fractions containing product were collected, evaporated in vacuum, the residue was re-dissolved in ACN (30 mL), filtered through celite and evaporated. The product was dried at 0.4 torr overnight, obtained 9.45 g (94%) of 30-Ac. $^1$H NMR (400 MHz, DMSO-D6): δ 1.21-1.15 (m, 12H), 1.49-1.46 (m, 22H), 1.76 (s, 9H), 1.88 (s, 9H), 1.98 (s, 12H), 2.01 (m, 9H), 2.09 (s, 9H), 2.21 (t, 2H), 2.27 (t, 6H), 2.9 (m, 1H), 3.02 (m, 14H), 3.52 (m, 12H), 3.70 (m, 10H), 3.88 (q, 3H), 4.0 (s, 9H), 4.1 (m, 1H), 4.48 (d, 3H), 4.7-4.5 (m, 1H), 4.98 (d, 3H), 5.21 (d, 3H), 6.84 (m, 4H), 7.02 (s, 1H), 7.17 (m, 5H), 7.28 (m, 4H), 7.79 (m, 3H), 7.88 (m, 6H). MALDI-MS: 2429 (M+Na)+.

Step (viii)[2-4]:

Triantennary GalNAc acid 30 from ester 26b

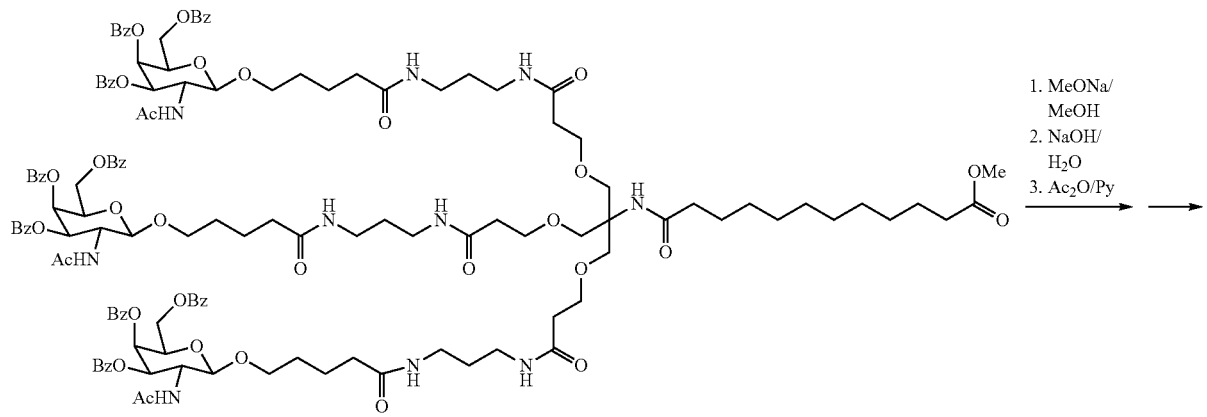

26b

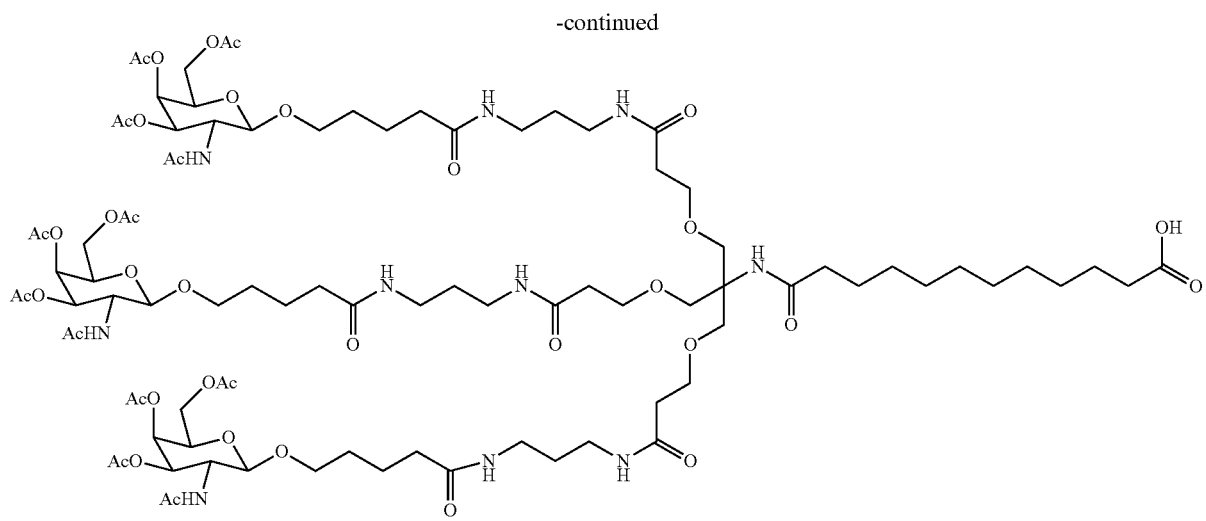

30

To a solution of triantennary ester 26b (13.5 g, 5.2 mmol) in anhydrous methanol (60 mL) at 0° C. was added 25 wt % solution of NaOMe (1.2 mL, 5.2 mmol) under Ar atmosphere. Cooling bath was removed, the mixture was stirred at rt for 1 h, neutralized with triethylamine hydrochloride (0.85 g, 6.2 mmol), evaporated in vacuum, and the residue was partitioned between 1% aq. NaCl (70 mL) and ethylacetate (40 mL). The aqueous layer was separated, washed with 40 mL ethylacetate and vacuumed on rotary evaporator until ~60 mL of the solution remained. NaOH (0.64 g, 16 mmol) was added, the mixture was stirred overnight at rt, neutralized with triethylamine hydrochloride (2.48 g, 18 mmol), diluted with 60 mL of pyridine, and the solvents were evaporated in vacuum till viscous oily residue that was coevaporated with additional 60 mL of pyridine and dissolved again in 60 mL of pyridine. The precipitate was filtered, washed with pyridine, and the combined filtrates were evaporated in vacuum and dried at 4 mbar/30° C. for 3 h to afford 11.06 g of residue. The latter was dissolved in anhyd. pyridine (40 mL) under Ar atmosphere and the solution was transferred via cannula to a vigorously stirred mixture of pyridine (50 mL) and acetic anhydride (25 mL, 260 mmol). The mixture was stirred at rt overnight, cooled to 0° C., and water (30 mL) was added. The mixture was stirred at rt for 0.5 h, and evaporated at 45° C. till viscous oily residue that was dried at 4 mbar/45° C. for 1.5 h. The residue was dissolved in a stirred mixture of ethylacetate (50 mL), isopropanol (15 mL) and 25% sodium chloride (50 mL), triethylamine was added drop wise till steady pH=7 (8 mL), and the liquids were decanted from solid NaCl to a separatory funnel. Organic layer was separated, washed 25% NaCl (50 mL), sat. NaCl (30 mL), dried over anhyd. sodium sulfate, the solvents were evaporated, the residue was coevaporated with ACN (×2), and dried at 0.4 torr overnight to afford 9.95 g (96%) of 30.

Example 5

Synthesis of Solid Supported GalNAc Monomer 32

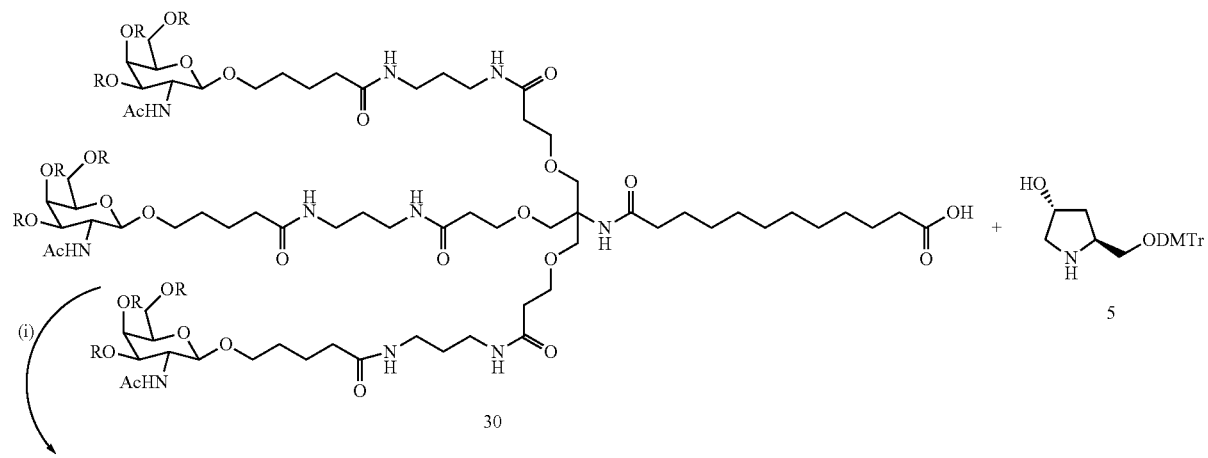

-continued

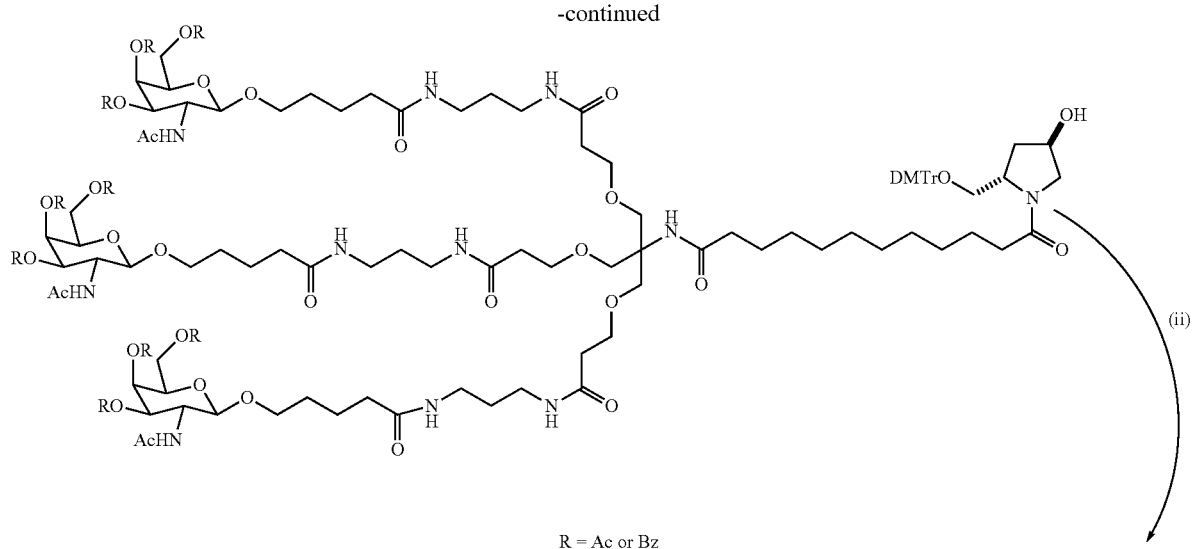

R = Ac or Bz

31

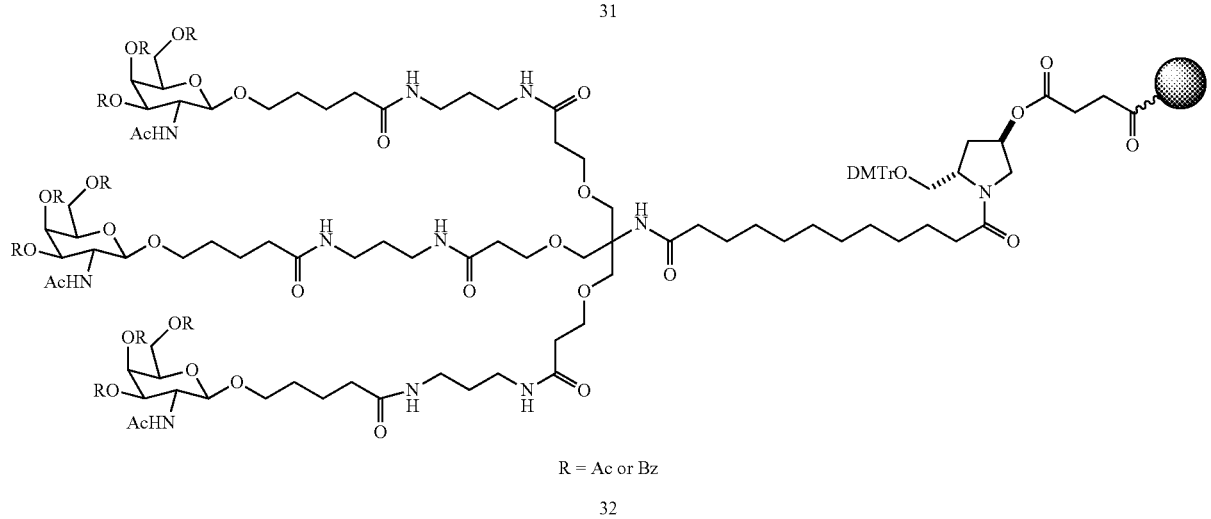

R = Ac or Bz

32

Reagents and conditions: (i) EDC.HCl, DIEA, HOBt/DCM-DMF or HBTU, DIEA/DCM-DMF or HBTU, DIEA, HOBt/DCM-DMF or EDC.HCl, DIEA, N-hydroxysuccinimide or EDC.HCl, DIEA, pentafluorophenol or DCC, DMAP/DCM-DMF or any other carboxylic acid activator for amidation/esterification; (ii)(1). Succinic anhydride, DMAP or succinic anhydride and DMAP immobilized on any solid support or succinic anhydride, pyridine or succinic anhydride and DIEA or succinic anhydride and $ET_3N$ and (ii)(2) step (i) and hydroxy or amino functionalized solid supports (e.g., control pore glass or any polymer support)

Triantennary Derivative 31 (Ac):

Step (i): To a stirred mixture of triantennary acid 30 (5.00 g, 2.5 mmol), hydroxyprolinol derivative 5 (1.17 g, 2.8 mmol), HBTU (1.14 g, 3.0 mmol), HOBt (1.01 g, 7.5 mmol) in anhyd. DCM (50 mL) was added DIEA (1.3 mL, 7.5 mmol). The mixture was stirred overnight, quenched with water (60 mL), the organic layer was separated, dried over anhyd. sodium sulfate, and evaporated to afford 9.21 g of residue. The latter was dissolved in a mixture of ethylacetate (80 mL) and DCM (30 mL), and loaded on a filtration column with silicagel (20 g) deactivated with 2% TEA in ethylacetate. The filtration column was eluted with 90 mL each: ethylacetate-TEA (2%) (×6), ethylacetate-methanol (10:1, ×1), and (3:1, ×3). Fractions containing product were collected, evaporated in vacuum, and the residue was coevaporated with ACN (×2). The product was dried at 0.4 torr overnight, obtained 4.77 g (80%) of 31 (Ac). $^1$H NMR (400 MHz, DMSO-D6): δ 1.21-1.15 (m, 12H), 1.49-1.46 (m, 22H), 1.76 (s, 9H), 1.88 (s, 9H), 1.98 (s, 12H), 2.01 (m, 9H), 2.09 (s, 9H), 2.21 (t, 2H), 2.27 (t, 6H), 2.9 (m, 1H), 3.02 (m, 14H), 3.52 (m, 12H), 3.70 (m, 10H), 3.88 (q, 3H), 4.0 (s, 9H), 4.1 (m, 1H), 4.48 (d, 3H), 4.7-4.5 (m, 1H), 4.98 (d, 3H), 5.21 (d, 3H), 6.84 (m, 4H), 7.02 (s, 1H), 7.17 (m, 5H), 7.28 (m, 4H), 7.79 (m, 3H), 7.88 (m, 6H). MALDI-MS: 2429 (M+Na)+.

Step (ii)[1]-Ac:

| S. No | Chemicals/Reagents & solvents | M. Wt. | Mol. | Eq. | Qty. |
|---|---|---|---|---|---|
| 1 | Compound from step (i)-Ac | 2407.69 | 0.06229 | 1 | 150 g |
| 2 | Succinic anhydride | 100.07 | 0.31146 | 5 | 31.17 g |
| 3 | PS-DMAP | — | — | 2 | 75 g |

-continued

| S. No | Chemicals/Reagents & solvents | M. Wt. | Mol. | Eq. | Qty. |
|---|---|---|---|---|---|
| 4 | Triethylamine | 101.19 | 0.9344 | 15 | 94.5 g |
| 5 | Dichloromethane (DCM) | — | — | 10V | 1500 ml |

A solution of compound from step (i) in DCM was prepared in a 2 L RB flask under nitrogen atmosphere at ambient temperature. To this solution, was added triethylamine during 10 minutes. Then succinic anhydride was added to it followed by PS-DMAP at ambient temperature. It was stirred for 12 hrs at ambient temperature (TLC and HPLC). The reaction mass was filtered through celite bed and washed with DCM (500 ml). Then the organic layer was diluted with DCM (1 L) and washed with water (3×4500 ml). Charcoal (7.5 g) was added to organic layer and stirred for 15 minutes. It was then filtered through celite bed and washed with DCM (500 ml). The filtrate was dried over anhydrous sodium sulfate and evaporated at reduced pressure at 30° C. to get the compound as off white solid 140 g (86%). $^1$H NMR (400 MHz, DMSO-D$_6$): δ 1.21 (m, 12H), 1.47-1.51 (m, 22H), 1.78 (s, 9H), 1.89 (s, 9H), 1.99 (s, 9H), 2.05 (m, 8H), 2.10 (s, 9H), 2.29 (m, 3H) 2.36 (m, 6H), 2.39 (q, 2H), 2.42 (q, 2H), 3.04 (m, 14H), 3.42 (q, 4H), 3.53 (m, 12H), 3.7 (m, 10H), 3.87-3.90 (q, 3H), 4.03 (s, 9H), 4.2 (m, 1H), 4.49-4.52 (d, 3H), 4.97-4.99 (d, 3H), 5.22 (s, 3H), 5.35 (s, 1H), 6.87 (m, 4H), 7.02 (s, 1H), 7.17 (m, 5H), 7.28 (m, 4H), 7.79 (m, 3H), 7.88 (m, 6H). $^{13}$C NMR (100 MHz, DMSO-D$_6$): δ 10.51, 2042, 21.84, 22.71, 24.48, 25.34, 28.54, 28.88, 28.99, 29.29, 29.72, 30.30, 33.10, 34.07, 35.04, 36.02, 36.26, 36.34, 45.37, 49.38, 52.34, 54.98, 59.48, 61.41, 63.24, 66.69, 67.31, 68.27, 68.64, 69.83, 70.50, 72.58, 85.29, 100.98, 113.11, 126.61, 127.58, 127.80, 129.61, 135.74, 158.03, 169.50, 169.66, 169.95, 170.02, 170.24, 172.09, 172.51, 172.63, 174.35. MALDI-MS: 2529 (M+Na).

Step (ii)[1]-Bz:

| S. No | Chemicals/Reagents & solvents | M. Wt. | mmol. | Eq. | Qty. |
|---|---|---|---|---|---|
| 1 | Compound from step (i)-Bz | 2964.63 | 29.68 | 1 | 88 g |
| 2 | Succinic anhydride | 100.07 | 59.37 | 2 | 5.94 g |
| 3 | PS-DMAP | — | — | 2 | 40 g |
| 4 | Triethylamine | 101.19 | — | — | 25 mL |
| 5 | Dichloromethane (DCM) | — | — | 10V | 800 ml |

Compound from step(i)-Bz was dissolved in DCM and triethyl amine. To this solution succinic anhydride and PS-DMAP were added and stirred the solution for 48 hrs. The mixture was filtered and washed with water and brine. The organic layer was dried over sodium sulfate and the solvents were removed under reduced pressure to get the compound as an off white solid (89.23 g, 95%). MALDI-MS cal. 3064.33. Found 3087.30 (M+Na).

Step (ii)[2]: General Process for the Synthesis of GalNAc Solid Supports 32 (Ac or Bz)-CPG, Polystyrene-Amino, Polystyrene-Amino Based Supports).

Example for polystyrene amino based support: Succinate from step (ii)[i] (32.50 g, 12.46 mmol) was taken in Acetonitrile (1000 mL) to that HBTU (11.80 g, 31.16 mmol) and DIEA (10 mL, 4 eq.) were added and mix reaction mixture for 5 minutes. Amino terminated polystyrene support (160 g) was added and shakes mixture for 24 hrs at room temperature. It was filtered and washed successively with DCM, 10% MeOH/DCM, DCM and Diethyl ether. It was dried under vacuum and checked the loading. The dried solid support was capped using 25% Ac$_2$O/Py for 3 hrs, washed and dried to get the required solid support (186 g, 67 µmol/g loading).

Reaction Conditions for Loading GalNAc Succinate Step (ii)[1] to Different Solid Supports Step (ii)[2]:

| GalNAc Support (PS) | Reaction Conditions | µmol of succinate/g of solid support | Loading | Quantity |
|---|---|---|---|---|
| Batch 1 | HBTU/DMF | 81 mmol/g | 60 mmol/g | 168 g |
| Batch 2 | HBTU/DMF | 80 mmol/g | 54 mmol/g | 167 g |
| Batch 3 | HBTU/DMF | 80 mmol/g | 40 mmol/g | 172 g |
| Batch 4 | HBTU/DMF | 76 mmol/g | 60 mmol/g | 2.70 g |
| Batch 5 | HBTU/DCM | 76 mmol/g | 48 mmol/g | 2.60 g |
| Batch 6 | HBTU/CH$_3$CN | 76 mmol/g | 64 mmol/g | 2.70 g |
| Batch 7 | HBTU/CH$_3$CN | 79 mmol/g | 67 mmol/g | 186 g |
| Batch 8 | HBTU/CH$_3$CN | 75 mmol/g | 63 mmol/g | 210 g |

Three different conditions were tried to make the polystyrene solid support results are shown below.

Loading of GalNAc succinate Step(i)[1] to Hydroxyl Terminated Polystyrene Support Following the same protocols described above different hydroxyl terminated polymer supports were loaded and the results are given below.

| Batch Number | Solvent | Pore size (Å) | Native Loading | µmol of succinate/ g of solid support | Loading | Quantity |
|---|---|---|---|---|---|---|
| Batch 9 | CH$_3$CN | 500 | 124 mmol/g | 77 mmol/g | 55 mmol/g | 5.00 g |
| Batch 10 | CH$_3$CN | 1000 | 96 mmol/g | 77 mmol/g | 38 mmol/g | 5.00 g |
| Batch 11 | CH$_3$CN | 1500 | 66 mmol/g | 77 mmol/g | 28 mmol/g | 5.00 g |
| Batch 12 | DMF | 500 | 124 mmol/g | 77 mmol/g | 42 mmol/g | 5.00 g |
| Batch 13 | DMF | 1000 | 96 mmol/g | 77 mmol/g | 22 mmol/g | 5.00 g |
| Batch 14 | DMF | 1500 | 66 mmol/g | 77 mmol/g | 15 mmol/g | 5.00 g |
| Batch 15 | CH$_3$CN | 500 | 124 mmol/g | 77 mmol/g | 65 mmol/g | 5.00 g |
| Batch 16 | CH$_3$CN | 1000 | 96 mmol/g | 77 mmol/g | 38 mmol/g | 5.00 g |
| Batch 17 | CH$_3$CN | 1500 | 66 mmol/g | 77 mmol/g | 28 mmol/g | 5.00 g |

Loading of GalNAc Succinate Step(i)[1] to Hydroxyl Terminated Polystyrene Support Following the same protocols described above different hydroxyl terminated polymer supports were loaded and the results are given below.

| Batch Number | Solvent | Material | µmol of succinate/g of solid support | Loading | Quantity |
|---|---|---|---|---|---|
| Batch 18 | CH$_3$CN | High loaded | 77 mmol | 72 mmol/g | 5.00 g |
| Batch 19 | CH$_3$CN | Low loaded | 77 mmol | 73 mmol/g | 5.00 g |
| Batch 20 | CH$_3$CN | High loaded | 153 mmol | 110 mmol/g | 2.50 g |
| Batch 21 | CH$_3$CN | High loaded | 77 mmol | 72 mmol/g | 5.70 g |
| Batch 22 | CH$_3$CN | High loaded | 153 mmol | 119 mmol/g | 3.30 g |
| Batch 23 | CH$_3$CN | High loaded | 202 mmol | 137 mmol/g | 2.70 g |

Example 6

Synthesis of DMTr-Prolinol 7A

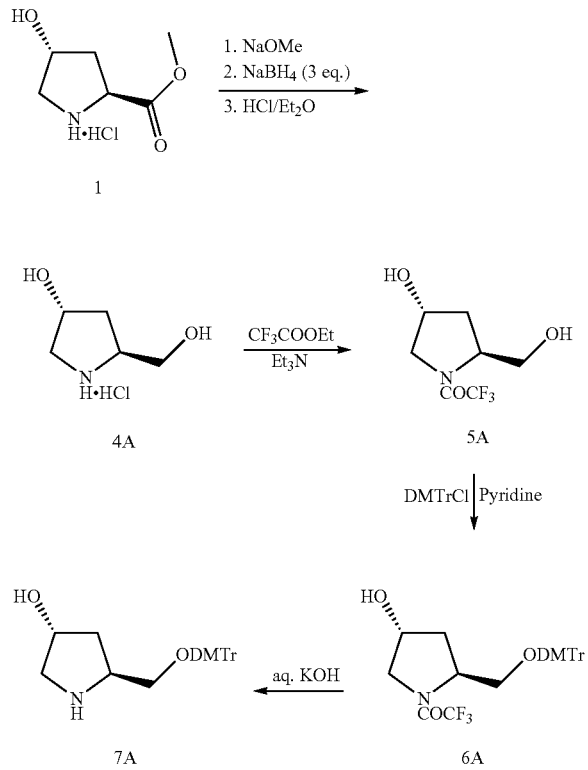

Step 1. trans-4-Hydroxyprolinol Hydrochloride 4A:

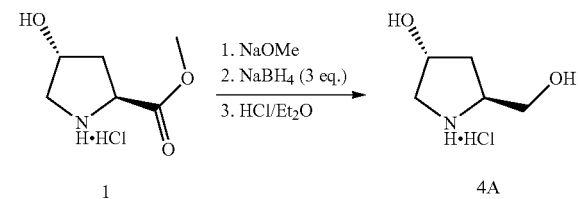

| | Reagents | MW | Qty Used | Moles | Mol. Eq. |
|---|---|---|---|---|---|
| 1 | Compound 1 | 181.6 | 131.6 g | 0.725 | 1 |
| 2 | NaOMe (25 wt % in MeOH) | 54.0 | 166 mL | 0.725 | 1 |
| 3 | NaBH$_4$ | 37.83 | 90.8 g | 2.39 | 3.3 |
| 4 | HCl in Dioxane (4M) | 36.5 | 800 mL | 3.2 | 4.4 |
| 5 | Anhyd. MeOH | | 1.3 L | | Solvent |
| 6 | Acetonitrile-low water | | >1.5 L | | Solvent |

Procedure 1:

The reaction was carried out in a 5 L flask fitted with a gas inlet, thermometer, reflux condenser and a gas outlet placed over a reflux condenser and connected to a bubbler. 25 wt. % Solution of NaOMe in MeOH (166 mL, 0.725 mol) was added to a cooled (0° C.) and stirred solution of 1 (131.6 g, 0.725 mol) in anhyd. MeOH (1.3 L) under Ar atm followed by portion-wise addition of NaBH$_4$ (90.8 g, 2.39 mol) for ~1.5 h. Significant exothermic effect observed during the addition of the first ⅓-portion of borohydride and the rate of addition was adjusted to maintain the reaction temperature below 20-25° C. The ice-water cooling bath was replaced with tap-water cooling bath and the mixture was stirred overnight while maintaining the temperature between 20-25° C. until hydrogen evolution ceased (gas bubbler monitoring). The reaction mixture was cooled to 0° C.; 4M solution of HCl in dioxane (3.2 mol, 800 mL) was added (exothermicity up to 30° C.), the cooling bath was removed and the mixture was stirred at rt for 2 h. The reaction mixture was filtered through a fine-porosity glass filter and the filtrate was evaporated under reduced pressure (80 mbar, 30° C.) until bulk crystallization occurred (~2 L of the solvent removed). Dry MeCN (1.5 L) was added, the mixture was triturated on rotary evaporator (20° C., 2 h) filtered, crystalline residue was washed once with MeCN, and dried overnight in slow flow of nitrogen to afford 93.0 g (84%) of pure 4A. Additional portion of 11.0 g (9%) of 4A slowly precipitated from the mother liquor that was contaminated with NH$_4$Cl and other minor impurities. $^1$H NMR (D$_2$O): 1.94-2.01 (m, 1H), 2.14-2.19 (m, 1H), 3.30-3.48 (m, 2H), 3.71-3.76 (m, 1H), 3.93-4.08 (m, 2H), 4.67-4.75 (m, 1H).

Procedure 2:

In order to optimize the above procedure in a larger scale the conversion of 1 to 4A was carried out in 3 mole scale and the procedure is given below.

| | Reagents | MW | Qty Used | Moles | Mol. Eq. |
|---|---|---|---|---|---|
| 1 | Compound 1 | 181.62 | 544.86 g | 3 | 1 |
| 2 | NaOMe (25 wt % in MeOH) | 54.00 | 686 mL | 3 | 1 |
| 3 | NaBH$_4$ (Aldrich Cat # 480886 (Granular) | 37.83 | 300 g | 7.93 | 2.64 |
| 4 | HCl in Dioxane (4M) | 36.5 | 3 L | 12 | 4 |
| 5 | Anhyd. MeOH | | 5 L | | Solvent |
| 6 | Acetonitrile | | 5 L | | Solvent | trans-4-Hydroxyproline methyl ester hydrochloride (1, 544.86 g, 3 mol) was added to a 20 L jacketed glass reactor fitted with a thermometer, reflux condenser and a solid addition funnel; the solid was dissolved in anhydrous methanol (5 L) under Ar atm and the solution was cooled to 0° C. A solution of NaOMe in MeOH (25 wt. %, 686 mL, 3 mol) was added to the cold solution under constant stirring and constant flow of Ar; followed by portion-wise addition of NaBH$_4$ (300 g, 2.64 mol) through the solid addition funnel for ~1.5 h. The rate of addition was adjusted to maintain the reaction temperature below 20-25° C. The reaction mixture was stirred overnight while maintaining the temperature between 25-30° C. until hydrogen evolution ceased (gas bubbler monitoring). The mixture was cooled back to 5° C.; 4M solution of HCl in dioxane (12 mol, 3 L) was added slowly under stirring; filtered through a fine-porosity glass filter and the filtrate was evaporated under reduced pressure (8 L of the solvent removed, initial crystallization of the product was observed). Anhydrous MeCN (4 L) was added to the slurry and the mixture was stirred at rt; filtered and the crystalline product was washed once with MeCN (1 L), and dried overnight in a vacuum oven at 40° C. to afford 423.0 g (92%) of 4A. However NMR analysis of the product indicated presence of unreacted ester 1 (<5%) The solid product was dissolved in hot methanol (800 mL) and filtered under hot to remove undissolved solids (presumably NaCl). The clear filtrate was diluted with 4 L of EtOAc and the solution was cooled oven an ice bath. Filtration of the crystallized product followed by drying provided the pure product 4A (1st crop 270 g+2nd crop 61 g=total 331 g, 72%) as white crystalline solid. $^1$H NMR (500 MHz, DMSO-d$_6$): δ 9.48 (s, 1H), 8.75 (d, J=187.3 Hz, 1H), 5.34 (dd, J=16.9, 11.7 Hz, 2H), 4.37 (s, 1H), 3.83-3.59 (m, 2H), 3.61-3.42 (m, 1H), 3.15 (t, J=26.0 Hz, 1H), 3.01 (t, J=21.2 Hz, 1H), 1.98-1.61 (m, 2H). $^{13}$C NMR (126 MHz, DMSO DMSO-d$_6$): δ 94.27, 68.77, 59.89, 59.86, 59.68, 52.42, 52.35, 35.39.

Example 7

Synthesis of Compound 5A

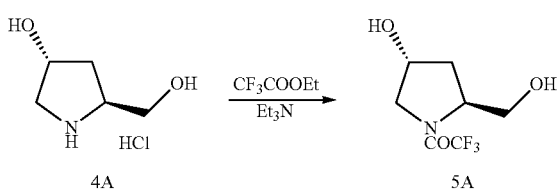

4A → 5A

| | Reagents | MW | Qty Used | Moles | Mol. Eq. |
|---|---|---|---|---|---|
| 1 | Compound 4A | 153.61 | 450 g | 2.94 | 1 |
| 2 | Et$_3$N | 101.19 | 1 L | 7.2 | 2.45 |
| 3 | CF$_3$COOEt | 142.08 | 1000 g | 7.04 | 2.4 |
| 4 | Acetonitrile | | 8 L | | Solvent |

The reaction was performed in a 5 necked 15 L glass reactor fitted with an overhead stirrer over an ice bath. To a stirred solution of 4A (450 g, 2.94 mol) in acetonitrile (8 L) were added Et$_3$N (1 L, 7.2 mol) and ethyl trifluoroacetate (1000 g, 7.04 mol), and stirred at room temperature overnight. The white solid (Et$_3$N.HCl) was filtered over sintered funnel and washed with EtOAc (4 L). The organic solution was concentrated followed by co-evaporation with toluene (2×2 L) and dried under reduced pressure overnight in a 22 L rotary evaporator to obtain crude 5A as a gummy mass (~600 g). Compound 5A thus obtained could be used for next step without further purification.

Example 8

Synthesis of Compound 7A

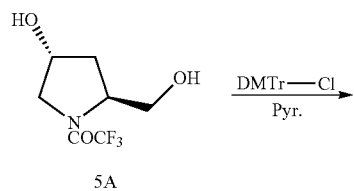

5A

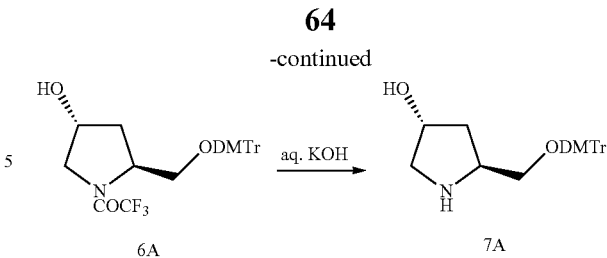

6A → 7A

| | Reagents | MW | Qty Used | Moles | Mol. Eq. |
|---|---|---|---|---|---|
| 1 | Compound 5A | 213.15 | 600 g (crude) | 2.94 | 1 |
| 2 | DMTr-Cl | 338.83 | 1000 g | 2.95 | 1 |
| 3 | KOH | 56.11 | 330 g | 5.88 | 2.0 |
| 4 | Anhy. Pyridine | | 8 L | | Solvent |
| 5 | MeOH | | 5 L | | Solvent |

The reaction was performed in a 5 necked 15 L glass reactor under nitrogen fitted with an overhead stirrer over an ice bath. The crude compound 5A (2.94 mol) was dissolved in 2 L of anhyd. pyridine and transferred to the 15 L flask. Another 6 L of anhydrous pyridine was added. This solution was cooled over an ice bath to ~5° C. followed by addition of DMTr-Cl (1000 g, 2.95 mol) portion wise under nitrogen atm over 20 min and the reaction mixture was stirred at rt overnight. Completion of the reaction was confirmed by TLC. Water (12 L) was added while stirring and let it stand for 6 h. The compound was settled at the bottom of the flask as a brownish gummy mass. Water-pyridine layer was decanted using transfer pump and the aqueous layer was extracted with ethyl acetate (EtOAc, 2×5 L). Combined the EtOAc extract with the viscous material remained in the reactor, after decanting water layer. Concentration of the solvent gave compound 6A as viscous oil which was used for the next step without purification.

The reaction (TFA deprotection) was performed in a 5 necked 15 L glass reactor fitted with an overhead stirrer. To a stirred solution of 6A (2.94 mol) in MeOH (5 L) was added KOH (330 g, 5.88 mol) in 2 L of water drop wise over 30 min and stirred at room temperature for 1 h. The reaction mixture was concentrated to 3 L volume under reduced pressure; 15 L of water was added to the concentrate and allowed to stand overnight. The product was settled at the bottom as reddish brown viscous oil. Decanted the water layer using transfer pump and 6 L of dichloromethane (DCM) was added to dissolve the settled product, washed with 5 L of water and separated the organic solvent. Concentration of the solvent followed by silica gel column chromatography (4 Kg silica, eluent: hexane/ethyl acetate and ethyl acetate/MeOH, see Table below for details) purification gave compound 7A (1000 g, 81% from compound 4A) as foamy yellowish white solid. $^1$H NMR (CDCl$_3$): 1.35-1.42 (m, 1H), 1.65-1.70 (m, 1H), 2.33 (br s, 1H), 2.59-2.62 (m, 1H), 2.72-2.75 (m, 1H), 2.82-2.91 (m, 2H), 3.36-3.41 (m, 1H), 3.71 (s, 6H), 4.1 (br s, 1H), 4.525 (d, J=4.0 Hz, 1H).

Example 9
Synthesis of $^{Bz}$GalNAc C$_5$ Acid 13B
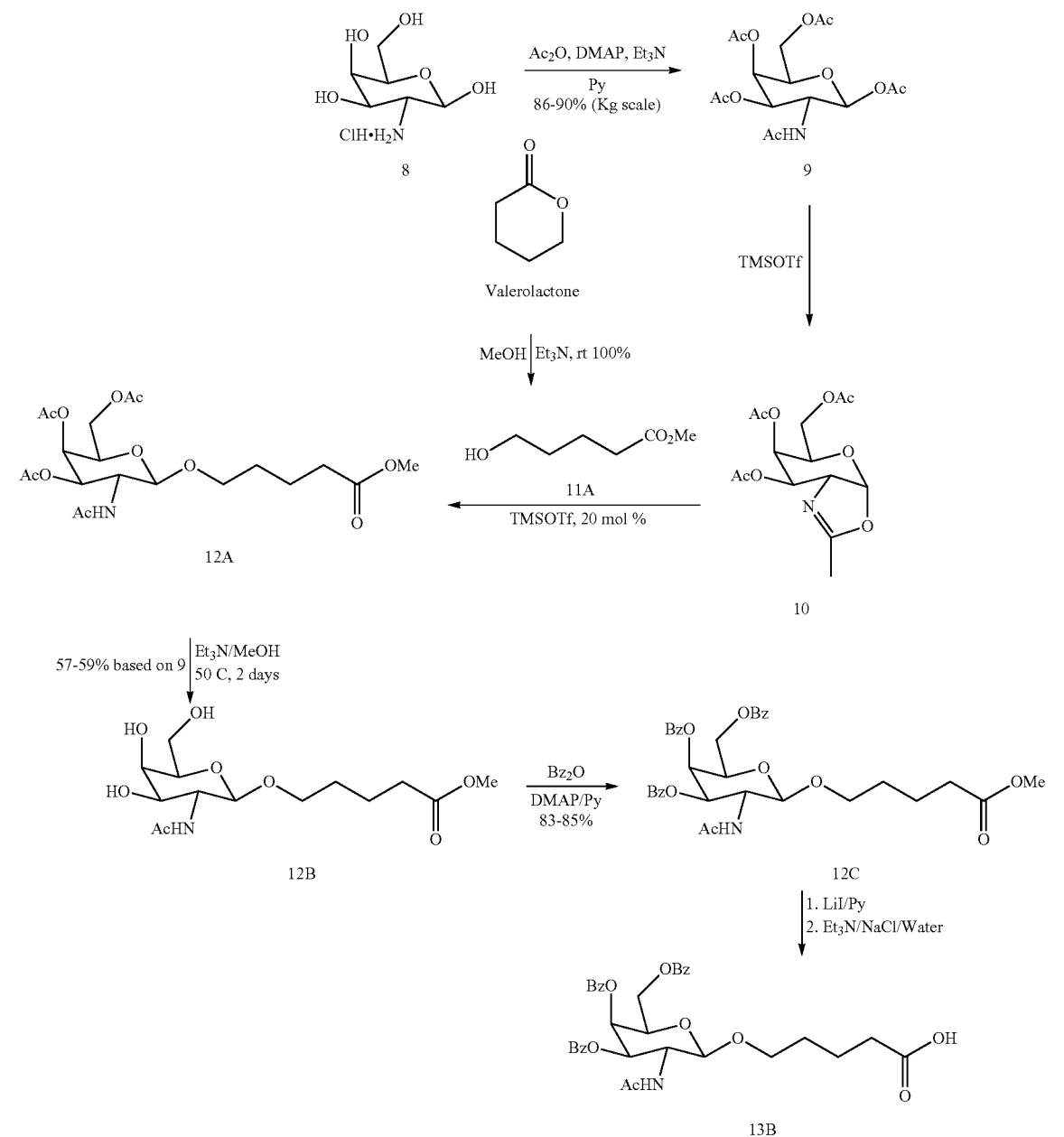
Pentaacetyl D-(+)-2-aminogalactose (9)
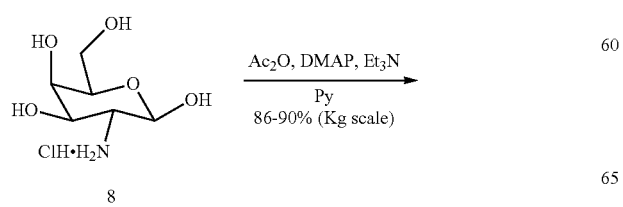
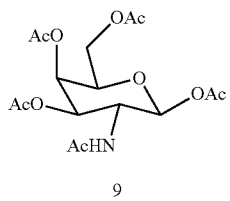

| | Reagents | MW | Qty Used | Moles | Mol. Eq. |
|---|---|---|---|---|---|
| 1 | Compound 8 | 215.6 | 1.63 kg | 7.55 | 1 |
| 2 | DMAP | 122.2 | 79 g | 0.646 | 0.085 |
| 3 | Triethylamine | 101.2 | 1.05 L | 7.55 | 1 |
| 4 | Acetic Anhydride | | 5.3 L | | Solvent |
| 5 | Anhy. Pyridine | | 7.2 L | | Solvent |
| 6 | Toluene | | 8 L | | Solvent |

Anhydrous pyridine (7.2 L) was added to a stirred and cooled (ice bath) suspension of D-(+)-galactosamine hydrochloride 8 (1.63 kg, 7.55 mol) in acetic anhydride (5.3 L) in a 40 L reactor under Ar atm. DMAP (79 g), and triethylamine (1.05 L, 7.55 mol) were added consecutively, and the mixture was stirred in the ice bath overnight during which time dissolution of 8 followed by crystallization of 9 and triethylamine hydrochloride occurred along with exothermic effect up to 30° C. for the first 2 hours. The mixture was filtered through a sintered glass filter, and the residue was washed with toluene (~4 L×2) followed by water (~3 L×2). The crystalline residue was dried overnight on the glass filter, transferred to drying dishes and dried on air (70° C. hot plate) for two days to afford 2.53 kg (86%) of pure 9. $^1$H NMR (400 MHz, DMSO) δ 7.88 (d, J=9.2 Hz, 1H), 5.63 (d, J=8.8 Hz, 1H), 5.26 (d, J=3.1 Hz, 1H), 5.05 (dd, J=11.3, 3.3 Hz, 1H), 4.34-3.82 (m, 4H), 2.11 (s, 3H), 2.03 (s, 3H), 1.98 (s, 3H), 1.90 (s, 3H), 1.77 (s, 3H).

Methyl 5-hydroxypentanoate 11A

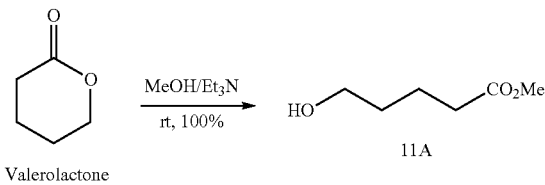 [SMILES: O=C1CCCCO1 ; COC(=O)CCCCO]

| | Reagents | MW | Qty Used | Moles | Mol. Eq. |
|---|---|---|---|---|---|
| 1 | Valerolactone | 100.1 | 1.0 kg | 10 | 1 |
| 2 | Triethylamine | 101.2 | 140 mL | 1 | 0.1 |
| 3 | Anhyd. MeOH | | 4 L | | Solvent |
| 4 | Anhyd. Toluene | | 4 L | | Solvent |

The reaction was performed in a 20 L rotary evaporation flask under slow flow of argon. A solution of valerolactone (98% purity, purchased from TCI, 1.0 kg, 10 mol) and triethylamine (140 mL, 1 mol) in dry methanol (4 L) was stirred at rt for 1 h, during which time slight exothermic effect (up to 28° C.) was observed. The mixture was concentrated in vacuum (25° C. heating bath), diluted with dry toluene (4 L), and evaporated under reduced pressure, and the residue was dried on rotary evaporator at 4 mbar/25° C. followed by stirring under high vacuum (0.4-0.6 torr, rt) overnight to afford 11A as a colorless liquid, 1.39 kg (100%), containing <1% of toluene. $^1$H NMR (400 MHz, CD$_3$CN) δ 3.61 (s, 3H), 3.49 (t, J=6.2 Hz, 2H), 2.55 (bs, 1H), 2.31 (t, J=7.4 Hz, 2H), 1.62 (dt, J=14.9, 7.1 Hz, 2H), 1.55-1.42 (m, 2H).

Oxazolidine Intermediate 10 (Crude)

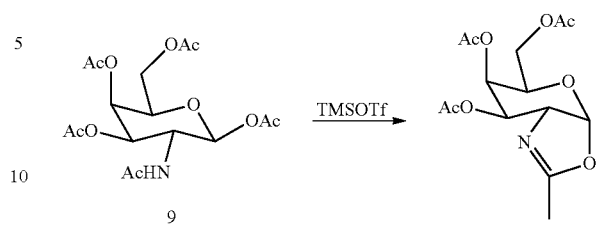

| | Reagents | MW | Qty Used | Moles | Mol. Eq. |
|---|---|---|---|---|---|
| 1 | Compound 9 | 389.4 | 2.52 kg | 6.49 | 1 |
| 2 | TMS triflate | 222.3 | 1.40 L | 7.74 | 1.2 |
| 3 | Sodium bicarbonate | 84.0 | 1.64 kg | 19.4 | 3 |
| 4 | Anhy. DCE | | 4 L | | Solvent |

The reaction was performed in a 20 L reactor under Ar atmosphere. TMSOTf (1.40 L, 7.74 mol) was added slowly (10 min) to a stirred suspension of 9 (2.52 kg, 6.49 mol) in anhyd. 1,2-dichlroethane (DCE, 4.0 L) under Ar atm. The mixture was stirred at rt overnight and transferred via transfer line to a vigorously stirred mixture of NaHCO$_3$ (1.64 kg, 19.4 mol), ice (5.5 L) and water (5.5 L) in an open 40 L reactor. The stirring was continued for 40 min, the organic layer was separated, the water layer was washed with dichloromethane (DCM 0.5 L×2), and the combined organic extracts were dried over anhyd. Na$_2$SO$_4$. The mixture was filtered, the solvent was evaporated, oily residue was dried on rotary evaporator (15 mbar at 30° C.), re-dissolved in anhyd. DCE (4.0 L), and the solvent was evaporated again and the residue was dried on rotary evaporator (3 mbar, 30° C.) to afford 2.14 kg of crude 10 that was re-dissolved in anhyd. DCE (4.0 L) and the solution thus obtained was used in the next step.

Peracetylated GalNAc Glycoside 12A (Crude)

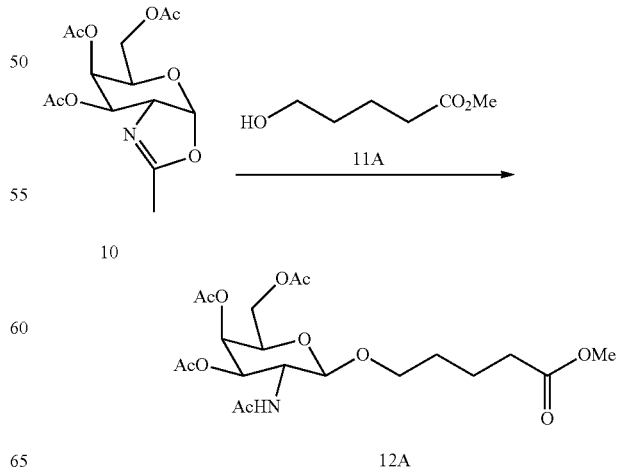

| | Reagents | MW | Qty Used | Moles | Mol. Eq. |
|---|---|---|---|---|---|
| 1 | Compound 10 (crude) | 329.3 | 2.14 kg | <6.49 | 1 |
| 2 | Compound 11A | 132.2 | 0.94 L | 7.14 | 1.1 |
| 3 | TMS triflate | 222.3 | 250 mL | 1.38 | 0.2 |
| 4 | Sodium bicarbonate | 84.0 | 168 g | 2.0 | 0.3 |
| 5 | Anhyd. DCE | | 6.5 L | | Solvent |

The reaction was performed in a 20 L reactor fitted with a cooling jacket under Ar atm. TMSOTf (250 mL, 1.38 mol) was added to a stirred and cooled (12° C.) solution of crude 10 (2.14 kg, ≤6.49 mol) and the methyl 5-hydroxypentanoate (11A, 0.94 L, 7.14 mol) in anhyd. DCE (6.5 L). Immediate exothermic effect (up to 23° C.) observed, the cooler was turned off, and the mixture was stirred at rt for 3 h and transferred to a 22 L open flask with a vigorously stirred mixture of NaHCO$_3$ (168 g, 2.0 mol), water (3 L), and some ice. The organic phase was separated, dried over anhyd. Na$_2$SO$_4$; solvent was evaporated, and the oily residue was dried on the rotary evaporator at 12 mbar/30° C. to afford 3.09 kg of crude 12A that was used in the next step without further purification. $^1$H NMR (400 MHz, CDCl$_3$): δ 5.73 (d, J=8.6 Hz, 1H), 5.35 (d, J=3.1 Hz, 1H), 5.26 (dd, J=11.2, 3.3 Hz, 1H), 4.68 (d, J=8.4 Hz, 1H), 4.34 (t, J=5.6 Hz, 1H), 4.21-4.04 (m, 3H), 3.93 (tdd, J=17.7, 11.1, 7.0 Hz, 3H), 3.72 (s, 3H), 3.70-3.62 (m, 4H), 3.57-3.41 (m, 2H), 2.55 (t, J=6.9 Hz, 1H), 2.32 (dt, J=23.8, 11.7 Hz, 3H), 2.18-2.11 (m, 4H), 2.11-1.78 (m, 14H), 1.78-1.44 (m, 5H).

Deprotected GalNAc Methyl Ester 12B

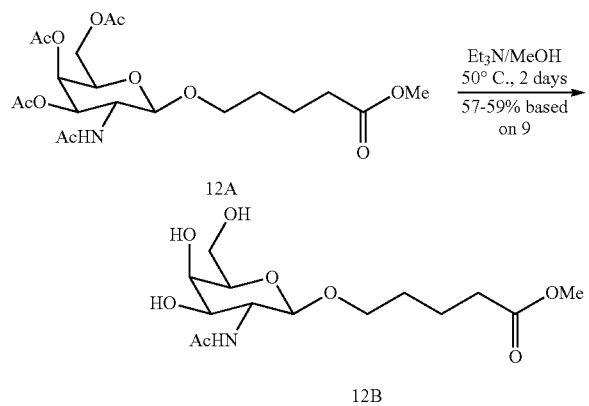

| | Reagents | MW | Qty Used | Moles | Mol. Eq. |
|---|---|---|---|---|---|
| 1 | Compound 12A (crude) | 461.5 | 3.09 kg | <6.49 | 1 |
| 2 | Triethylamine | 101.2 | 0.90 L | 6.49 | 1 |
| 3 | MeOH | | 10 L | | Solvent |
| 4 | Toluene | | 14 L | | Solvent |
| 5 | Ethanol | | 4 L | | Solvent |

The reaction was performed in a 20 L filtration reactor fitted with a heating/cooling jacket. Crude 12A (3.09 kg, ≤6.49 mol) was dissolved in anhydrous methanol (10 L) under Ar atm, triethylamine (0.90 L, 6.49 mol) was added to the solution and was heated at 50° C. for 2 days under stirring. The reaction mixture was diluted with toluene (4 L) and the solution was allowed to cool to rt overnight during which time bulk crystallization occurred. The slurry was cooled to 0° C., stirred overnight, filtered, and the solid was washed with 10% methanol in toluene (8.8 L) and dried on air (65° C. on hot plate) to afford 0.97 kg of 12B. Filtrate was concentrated under reduced pressure till bulk precipitation begun. Dry ethanol (4.0 L) was added to the concentrate and the resulting slurry was triturated on the rotary evaporator at rt overnight, filtered, and the solid was washed with toluene-ethanol mixture (1:1, ~2 L) to afford additional 191 g of 12B after drying on air (65° C. on hot plate). Total yield: 1.16 kg, 54% based on 9, ~95% purity. $^1$H NMR (400 MHz, DMSO-d$_6$): δ 7.58 (d, J=9.1 Hz, 1H), 4.60-4.47 (m, 2H), 4.44 (d, J=4.3 Hz, 1H), 4.20 (d, J=8.4 Hz, 1H), 3.77-3.60 (m, 3H), 3.56 (s, 3H), 3.54-3.21 (m, 6H), 2.28 (t, J=7.4 Hz, 2H), 1.78 (d, J=6.6 Hz, 3H), 1.59-1.36 (m, 4H).

Perbenzoylated GalNAc Glycoside 12C

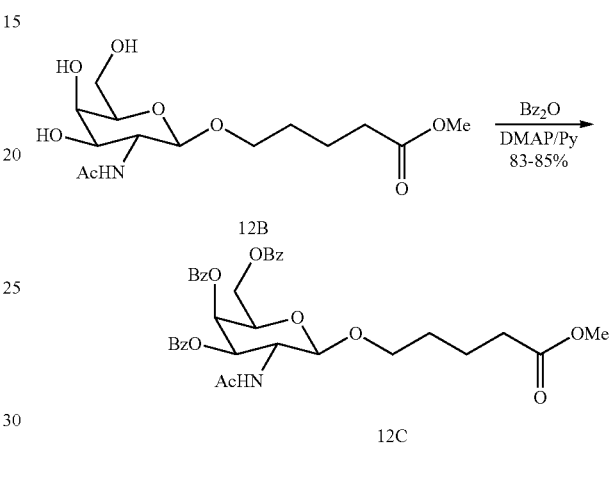

| | Reagents | MW | Qty Used | Moles | Mol. Eq. |
|---|---|---|---|---|---|
| 1 | Compound 12B (~95%) | 335.4 | 1.06 kg | 3.15 | 1 |
| 2 | DMAP | 122.2 | 384 g | 3.15 | 1 |
| 3 | Benzoic anhydride | 226.2 | 2.49 kg | 11.02 | 3.5 |
| 4 | Anhy. Pyridine | | 9.0 L | | Solvent |
| 5 | Ethyl acetate | | 12 L | | Solvent |
| 6 | Ethanol | | 14-15 L | | Solvent |

Glycoside 12B (1.06 kg, 3.15 mol, ~95% purity) and DMAP (384 g, 3.15 mol) were dissolved in anhyd. pyridine (9.0 L) under Ar atm. Benzoic anhydride (2.49 kg, 11.02 mol) was added and the mixture was stirred overnight; water (200 mL) was added to the reaction mixture and the stirring was continued for additional 0.5 h. Pyridine was removed from the reaction mixture under reduced pressure and the residue was dried on the rotary evaporator at 10 mbar/35° C. The residue was partitioned between water (2 L) and EtOAc (4 L) in the 20 L rotary evaporator flask till complete dissolution of solids, transferred to an extraction vessel, and diluted with additional EtOAc (8 L) and water (5 L). The organic layer was separated and washed consecutively with water (10 L), sat. NaHCO$_3$ (2×5 L), and again water (2×5 L). The organic layer was separated and the solvent was evaporated under reduced pressure till viscous mass. The oily residue was re-dissolved in ethanol (3.8 L) and evaporated again under reduced pressure. The residue thus obtained was dried on the rotary evaporator at 20 mbar/35° C. for ca 2 h. The residue was re-dissolved in ethanol (10.6 L) at 35° C. and transferred to a 20 L filtration reactor fitted with heating/cooling jacket. Water (6.0 L) was added portion wise at 35° C., and the mixture was allowed to cool down to 22° C., and seeds of 12C were added to the solution. Bulk crystallization occurred after stirring overnight; the mixture was cooled to 0° C., stirred for additional 5 h and filtered. The precipitate was pre-dried by passing air overnight, transferred to drying dishes, and dried on air (65° C. on hotplate for 2 days) till constant mass to afford 1.70 kg (84%) of 12C (~97% purity, containing ~3% of the corresponding methyl glycoside). $^1$H NMR (400 MHz, DMSO-$d_6$): δ 8.05-7.84 (m, 1H), 7.76-7.30 (m, 2H), 5.75 (d, J=3.2 Hz, 1H), 5.35 (dd, J=11.1, 3.3 Hz, 1H), 4.73 (d, J=8.5 Hz, 1H), 4.54-4.41 (m, 1H), 4.41-4.18 (m, 1H), 3.79 (dd, J=10.0, 4.7 Hz, 1H), 3.56 (s, 1H), 3.55-3.47 (m, 1H), 2.29 (t, J=7.0 Hz, 1H), 1.69 (s, 1H), 1.55 (dd, J=11.8, 9.1 Hz, 1H).

$^{Bz}$GalNAc $C_5$ Acid Sodium Salt 13B

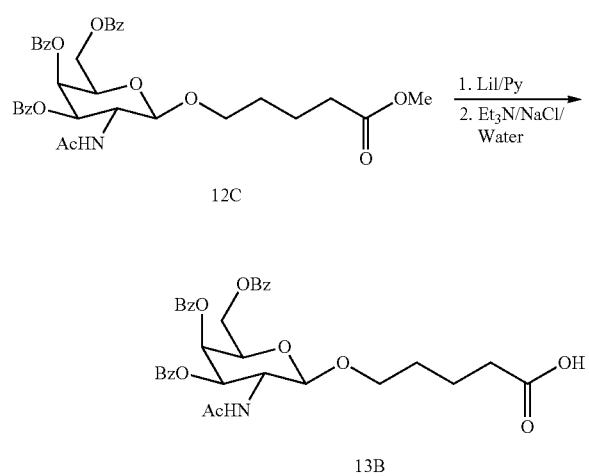

| | Reagents | MW | Qty Used | Moles | Mol. Eq. |
|---|---|---|---|---|---|
| 1 | Compound 12C (~97%) | 647.7 | 1.70 kg | 2.63 | 1 |
| 2 | Lithium Iodide anhyd. | 133.8 | 1.41 kg | 10.52 | 4 |
| 3 | Triethylamine | 101.2 | 384 mL | 2.76 | 1.05 |
| 4 | Anhy. Pyridine | | 4.5 L | | Solvent |
| 5 | Phosphoric acid | | 6.0 L | | |
| 6 | Silica gel | | 2.5 kg | | |
| 7 | Isopropanol | | 1 L | | Solvent |
| 8 | Acetonitrile | | 12 L | | Solvent |
| 9 | Ethyl acetate | | ~50 L (total) | | Solvent |
| 10 | Hexanes | | ~20 L (total) | | Solvent |

Anhyd. LiI ("ultra-dry"—Alfa-Aesar, 1.41 kg, 10.52 mol) was added portion wise for ~30 min to a stirred solution of methyl ester 12C (1.70 kg, 2.63 mol), in anhyd. pyridine (4.5 L) under Ar atm in a 12 L 4-neck flask fitted with gas inlet, thermometer, reflux condenser, and heating mantle. Exothermic effect up to 70° C. observed during the addition. The mixture was further heated under gentle reflux (125° C. in the flask) for 25 h, cooled to rt, and diluted with water (1.5 L). Pyridine was evaporated; the oily residue was dried on rotary evaporator at 11 mbar/35° C., diluted with water again (2 L), evaporated and dried at 10 mbar/35° C. for 3 h. The residue (4.86 kg) was partitioned between chilled 20% $H_3PO_4$ (6 L), water (2 L), and EtOAc-hexane mixture (2:1, 8 L). The organic phase was separated, and the water phase was washed again with EtOAc-hexane mixture (2:1, 3×3 L). Combined organic extracts were washed with 5% aq. NaCl (6 L), and dried over anhyd. $Na_2SO_4$. The solution (total volume ~20 L) was decanted form the drying agent and filtered through a plug of 2.5 kg silica gel (wet-loaded in EtOAc-hexane mixture (2:1) on a sintered glass 6 L filter funnel). The silica gel cake was washed with EtOAc-hexane 2:1 mixture, until no substantial amount of the acid in the filtrate was observed by TLC (45 L). The combined filtrates were evaporated and dried at 20 mbar/35° C. to afford crude acid as soft foam (1.78 kg) that was dissolved in EtOAc (4 L) and hexanes (2 L). Triethylamine (384 mL, 2.76 mol) followed by 5% NaCl solution (2.3 L) were added. The bottom aqueous layer containing triethylammonium salt of the acid 13B was separated, and the organic layer after washing with 5% NaCl (0.5 L×2) was discarded. The product was extracted from the combined aqueous layer into a mixture of EtOAc and isopropanol (5:1, 6 L); the organic layer was washed with 5% NaCl (4 L×3), saturated NaCl (1 L×2) and dried over anhyd. $Na_2SO_4$. The solvents were evaporated under reduced pressure; the residue was dried briefly on the rotary evaporator at 20 mbar/35° C., and dissolved in acetonitrile (ACN, 6 L). The solution was filtered from inorganic precipitate through a sintered glass filter, evaporated, dried briefly on the rotary evaporator at 20 mbar/30° C., redissolved in ACN (6 L), evaporated again, and dried under high vacuum to afford 1.58 kg (93%) of pure sodium salt 13B. $^1$H NMR (400 MHz, DMSO-$d_6$): δ 8.50 (d, J=9.1 Hz, 1H), 7.90 (dd, J=10.9, 4.0 Hz, 4H), 7.82-7.28 (m, 11H), 5.75 (d, J=3.2 Hz, 1H), 5.46-5.26 (m, 1H), 4.75 (dd, J=32.1, 8.6 Hz, 1H), 4.53-4.20 (m, 4H), 3.74 (dt, J=11.1, 5.7 Hz, 1H), 3.54 (dt, J=10.6, 5.5 Hz, 1H), 2.01-1.82 (m, 2H), 1.71 (s, 3H), 1.65-1.33 (m, 4H).

Example 9

Synthesis of Tris(tert-Butyl)-Tris amine 17A (tert-Butyl-3,3'-(2-amino-2-((3-tert-butoxy-3-oxo-propoxy)methyl)propane-1,3-diyl)bis(oxy)dipropanoate)

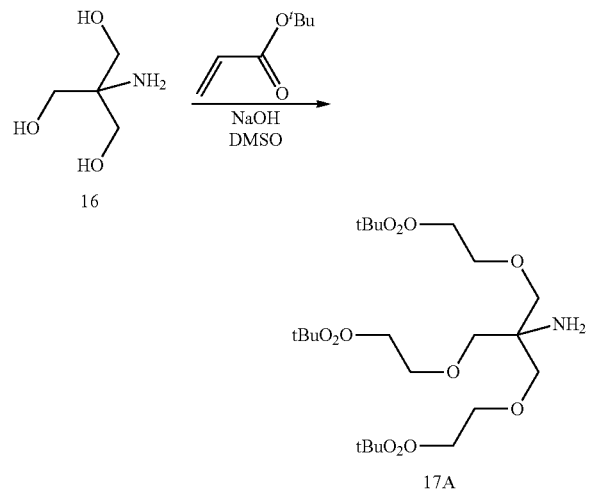

| Reagents | MW | Qty Used | Moles | Mol. Eq. |
|---|---|---|---|---|
| 1 Tris(hydroxymethyl)aminomethane (TRIS) | 121.07 | 500 g | 4.129 | 1 |
| 2 tert-Butyl Acrylate (d = 0.875) | 128.08 | 2300 mL + 1550 mL | 26.00 | 6.29 |
| 3 NaOH (5M in water)* | 40.00 | 2 × 83 mL | — | — |
| 4 DMSO | — | 830 mL | — | Solvent |
| 5 Ethyl acetate | | 48 L | | Solvent |
| 6 Hexane | | 24 L | | Solvent |
| 7 Toluene | | 4 L | | Solvent |
| 8 Methanol | | 1 L | | Solvent |

*40 g of NaOH was dissolved in 200 mL of water

TRIS (500 g) and DMSO (830 mL) were added under argon into a 12 L four necked flask equipped with an overhead stirrer over an ice-water bath. The reaction mixture was cooled to about 15° C. and stirred the mixture for about 10 min to dissolve TRIS completely (or until the reaction mixture become a homogeneous solution). 5 M NaOH (83 mL) was added at time and stirred the mixture for 5 min. tert-Butyl acrylate (2300 mL) was added to the above mixture slowly under constant stirring over a period of 1 h and maintained the reaction temperature at around ~15° C. during the addition. Slowly warmed the mixture to ambient temperature and continued stirring for 24 h under argon. TLC (eluent: 2% MeOH/EtOAc-basic KMnO$_4$ stain) and mass analysis of the reaction mixture after 24 h showed the presence of large excess of the di-addiction (di-adduct) product (incomplete Michael addition).

To drive the reaction to completion an additional 83 mL of 5M NaOH was added to the reaction mixture followed by 1550 mL of tert-butyl acrylate. The stirring was continued for another 24 h. The reaction mixture was transferred to a rotary evaporator and washed the flask with 2 L of EtOAc. Unreacted tert-butyl acrylate was removed and the residue was co-evaporated with toluene (2×2 L). The residue obtained was dissolved in EtOAc (4 L) and washed with equal volume of water, the layers were not separating well, upon addition of 2 L of saturated brine to the mixture separated the organic and aqueous phase. The washing process was repeated once again. The first aqueous layer was washed with 2 L of ethyl acetate and the combined organic layer was dried over sodium sulfate. Solvents were removed in vacuo and the residue (2.023 Kg, crude weight) was purified by filtration silica gel column followed by a second column chromatography as described below.

Filtration column chromatography: A slurry of 3 Kg of silica gel in hexane was packed and the crude compound was loaded, eluted successively with hexane (4 L) 1:3 EtOAc/hexane (4 L) and 1:1 EtOAc/hexane (8 L) and 2.5% MeOH in EtOAc (12 L). The di-addition product (di-adduct) was completely removed. Pooled all fractions containing the desired compound 17A (tri-adduct), evaporated (1530 g—crude weight) and divided into two halves for second column chromatographic purification.

Final Purification of 17A: The residue from the filtration column was divided into two halves for second purification. Column conditions: ~765 g of the crude from the filtration column was dissolved in minimum amount of EtOAc/hexane and loaded on 3 Kg silica gel (3 Kg) packed in hexane. Eluted successively with hexane (4 L), 1:3 EtOAc/hexane (4 L), 3:7 EtOAc/hexane (4 L), 3:1 EtOAc/hexane (4 L); and 2.5% MeOH in EtOAc (12 L).

The column chromatography was repeated under same conditions to isolate compound 17A from the second portion. Pooled pure fractions were evaporated under reduced pressure to obtain the pure compound 17A as viscous oil (1087 g, 56%). $^1$H NMR (400 MHz, DMSO-d$_6$): δ 3.54 (t, J=6.0 Hz, 6H), 3.16 (s, 6H), 2.38 (t, J=6.0 Hz, 6H), 1.39 (s, 27H). $^{13}$C NMR (101 MHz, DMSO-d$_6$): δ 171.06, 80.30, 73.13, 67.46, 56.42, 40.21, 40.21, 39.89 39.58, 36.50, 28.40.

Example 10

Synthesis of Tris(tert-Butyl) C$_{12}$ Methyl Ester 18A

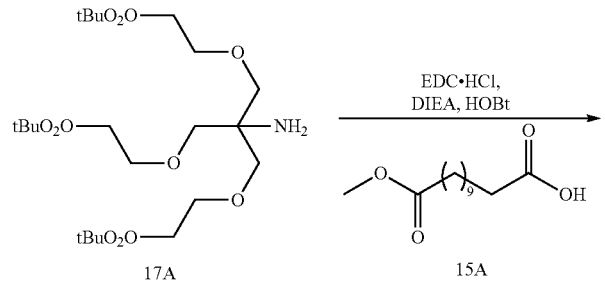

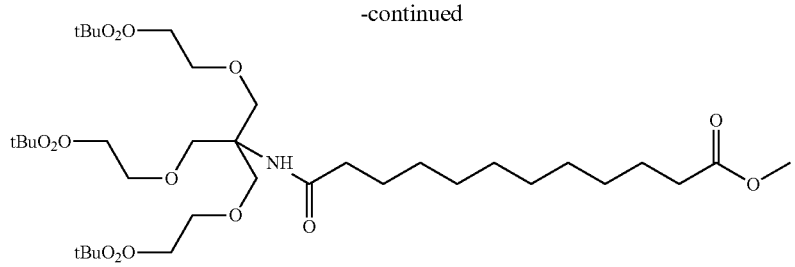

18A

| Reagents | MW | Qty Used | Moles | Mol. Eq. |
| --- | --- | --- | --- | --- |
| 1 Compound 17A | 505.33 | 1081.00 g | 2.139 | 1 |
| 2 Monomethyl-1,12-dodecanedioic acid (15A) | 244.17 | 653 g | 2.673 | 1.25 |
| 3 EDAC•HCl | 198.4 | 531 g | 2.673 | 1.25 |
| 4 HOBt | 135.1 | 433.54 | 3.209 | 1.50 |
| 5 DIEA (d 0.742) | 129.1 | 1.12 L | 6.42 | 3.00 |
| 6 Anhyd. DMF | — | 1 L | — | Solvent |
| 7 Anhyd. DCM | — | 6 L | — | Solvent |
| 8 Ethyl acetate | | 10 L | | Solvent |
| 9 Toluene | | 8 L | | Solvent |
| 10 DCM | | 4 L | | Solvent |

Compound 17A (1081 g, 2.139 mol), monomethyl ester 15A (653 g, 2.673 mol) and HOBt (433.5 g, 3.209 mol) were dissolved in a mixture of DCM (6 L) and DMF (1 L) in a 12 L four necked RB flask equipped with an overhead stirrer under argon. EDAC.HCl (531 g, 2.673 mol) was added portion wise to the reaction mixture under constant stirring. Stirred the reaction mixture for 15 min (or until the reaction mixture become a homogeneous solution) and cooled over an ice-water bath to about ~10° C. DIEA (1.12 L, 6.42 mol) was added over a period of 30 min while maintaining the temperature around ~10° C. Slowly warmed the reaction mixture to ambient temperature and stirred under argon for two days. TLC (eluent: 35% EtOAc/Hexanes, basic KMnO$_4$ stain) checked and transferred the solutions to a 20 L rotary evaporator; removed solvents and volatiles under reduced pressure. After removing most of the dichloromethane the flask was transferred to a hood and fitted with an overhead stirrer. Water (15 L) was added with stirring and a gummy liquid separated out. The above mixture was kept for settling overnight at ambient temperature. The top layer was decanted and bottom viscous layer was dissolved in 8 L of EtOAc and washed successively with water (2×4 L), 10% aqueous citric acid (2×3.5 L), aq. NaHCO$_3$ solution (2×2.5 L), followed by saturated brine (2.5 L) wash. The organic layer was separated and dried over sodium sulfate. Solvent was removed under reduced pressure and the residue was co-evaporated with anhydrous toluene (2 L). The residue was dried under high vacuum overnight to obtain compound 18A as a colorless viscous oil (1641 g, 77 g more than quantitative yield—small amount of HOBt and toluene were present) which was used for the next reaction without further purification. $^1$H NMR (400 MHz, DMSO-d$_6$): δ 6.85 (s, 1H), 3.53 (dd, J=12.9, 6.9 Hz, 16H), 3.30 (s, 1H), 2.49 (dd, J=3.5, 1.7 Hz, 2H), 2.37 (t, J=6.1 Hz, 7H), 2.26 (t, J=7.4 Hz, 2H), 2.02 (t, J=7.3 Hz, 2H), 1.56-1.44 (m, 3H), 1.44-1.34 (m, 32H), 1.21 (s, 13H). MS calc for C$_{38}$H$_{69}$NO$_{12}$: 731.48. found 732.3 (M+H).

Example 11

Synthesis of Tricarboxylic Acid C$_{12}$ Methyl Ester 19A

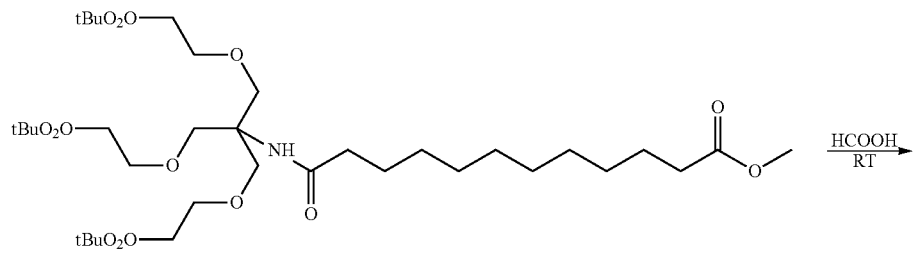

18A

-continued

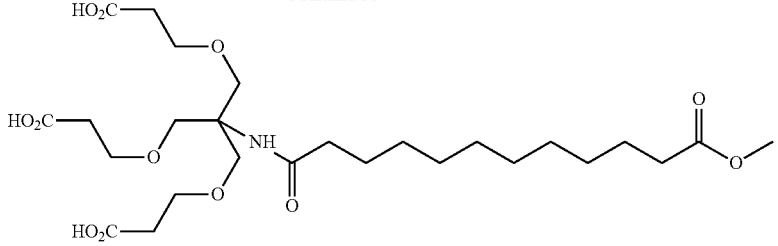

19A

| | Reagents | MW | Qty Used | Moles | Mol Eq. |
|---|---|---|---|---|---|
| 1 | Compound 18A | 731.48 | 1560 g | 2.134 | 1 |
| 2 | Formic acid 98% | — | 10 Kg (8.2 L) 5 Kg (4.1 L) | — | Solvent |
| 3 | Anhyd. Ether | | 4 L | | Solvent |
| 4 | Ethyl acetate | | 6 L | | Solvent |
| 5 | Toluene | | 9 L | | Solvent |
| 6 | Hexane | | 6 L | | Solvent |

Compound 18A (1560 g, 2.134 mol) was charged to a 22 L four necked RB flask equipped with an overhead stirrer under argon. Formic acid (10 Kg-8.2 L) was added to the reaction flask and all reagents went in to solution within 20 min and stirred for 24 h under argon. TLC (eluent: 35% EtOAc/Hexanes-basic KMnO$_4$ stain) showed incomplete reaction and presence of unreacted 18A. An additional 4.1 L of formic acid was added and continued the stirring for another 24 hrs. TLC and mass spectra showed completion of reaction and the mixture was transferred to a 20 L rotary evaporator and volatiles were removed under reduced pressure. After the removal of formic acid the residue was co-evaporated with toluene (2×4.5 L). Mixture of EtOAc and hexane (1:1, 8 L) was charged into the rotating flask on the rotary evaporator under slow rotation, white solid precipitated from the solution and the mixture was slowly rotated for another 2 h on the rotary evaporator (until free flowing solid separated out). The solid was filtered and washed with EtOAc/hexane (1:1, 4 L) followed by anhydrous ether (4 L). The solid was transferred to a tray and air dried at 45° C. until it reaches constant weight to get the compound 19A as a white powder (yield 1096 g, 91%).

Recrystallization of 19A from ethyl acetate affords product devoid of traces of partially deprotected tert-butyl ester. 19A (5.0 g) was dissolved in refluxed ethyl acetate (25 mL) and the hot clear solution was decanted from the flask that contains residual solids. The flask was rinsed with small amount of ethyl acetate, and the combined decanted solution was allowed to cool down to rt overnight. The precipitate was filtered and air-dried to afford 4.75 g (95%) of 19A. $^1$H NMR (400 MHz, DMSO-d$_6$): δ 12.08 (bs, 3H), 6.89 (s, 1H), 3.65-3.43 (m, 7H), 2.41 (dt, J=12.7, 6.3 Hz, 3H), 2.26 (t, J=7.4 Hz, 1H), 2.02 (t, J=7.3 Hz, 1H), 1.44 (ddd, J=19.5, 13.3, 6.7 Hz, 2H), 1.21 (s, 5H). $^{13}$C NMR (101 MHz, DMSO-d$_6$): δ 173.41, 172.70, 172.56, 68.21, 66.75, 59.57, 51.18, 40.13, 39.92, 39.71, 39.51, 39.30, 39.09, 38.88, 35.94, 34.67, 33.33, 28.99, 28.94, 28.89, 28.75, 28.57, 28.55, 25.35, 24.51. MS calc for C$_{26}$H$_{45}$NO$_{12}$: 563.29. found 564.3 (M+H).

Example 12

Synthesis of Tris($^{Boc}$Amine) Methyl Ester 24A

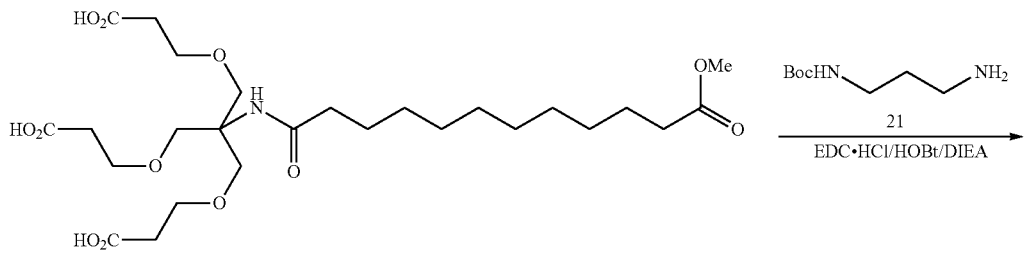

19A

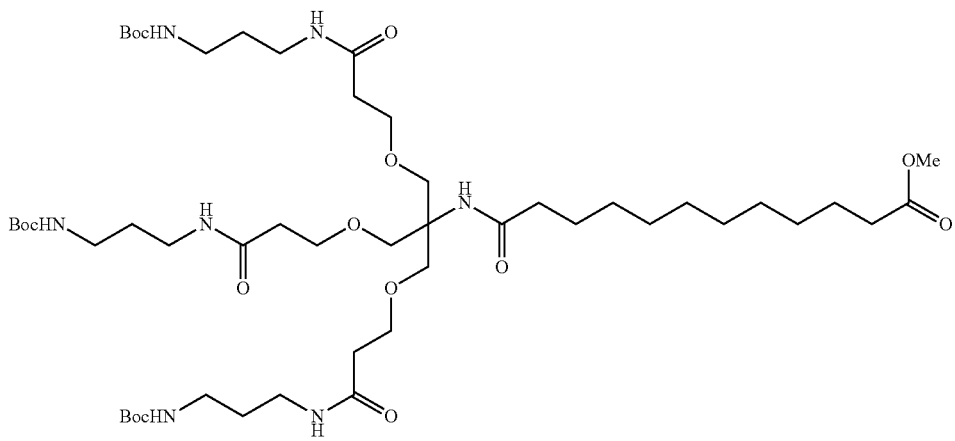

24A

| | Reagents | MW | Qty Used | Moles | Mol Eq. |
|---|---|---|---|---|---|
| 1 | Compound 19A | 563.29 | 1090.00 g | 1.936 | 1.00 |
| 2 | Mono Boc propanediamine 21 | 174.24 | 1265.00 g | 7.260 | 3.75 |
| 3 | EDAC•HCl | 198.4 | 1440 g | 7.260 | 3.75 |
| 4 | HOBt | 135.1 | 1170 g | 8.667 | 4.50 |
| 5 | DIEA (d 0.742) | 129.1 | 2.40 L | 13.55 | 7.00 |
| 6 | Anhydrous DMF | — | 2 L | — | Solvent |
| 7 | Anhydrous DCM | — | 9 L | — | Solvent |
| 8 | Ethyl acetate | | 8 L | | Solvent |
| 9 | Toluene | | 2.5 L | | Solvent |
| 10 | DCM | | 6 L | | Solvent |

Tricarboxylic acid 19A (1090 g, 1.936 mol) and HOBt (1170 g, 8.667 mol) were taken in a 22 L four necked flask equipped with an overhead stirrer under argon. 4 L of DCM and 2 L of DMF were added to the mixture with constant stirring. The reaction mixture was cooled over an ice-water bath to ~10° C. A solution of mono Boc propanediamine 21 (1265 g, 7.260 mol) in 2 L of DCM was added to the solution under stirring. Reaction became homogenous in 15 min. Slurry of EDAC.HCl (1440 g, 7.260 mol) in 4 L of DCM was slowly added to the reaction mixture followed by slow addition of DIEA (2.40 L, 13.55 mol) over a period of 1.5 h to the flask under argon while maintaining the temperature ~10° C. The color of the solution turned to light brownish yellow; the mixture was slowly warmed to ambient temperature and stirred overnight under argon atm. TLC (eluent: 10% MeOH/DCM, basic KMnO$_4$ stain) checked and the reaction mixture was transferred to a 20 L rotary evaporator; removed DCM and volatiles under reduced pressure. The flask was transferred to a hood and fitted with an overhead stirrer. 10 L of water was added to the residue with stirring to form a milky solution. The mixture was kept overnight for settling down. Two layers were separated by overnight and decanted the top layer using a transfer pump. The bottom layer was dissolved in 8 L of EtOAc and transferred to a separatory funnel. The EtOAc layer was washed successively with water (2×4 L water+2 L brine), aq. NaHCO$_3$ solution (2.5 L+1 L brine), 10% aq. citric acid solution (2×3.5 L+1 L brine), water (1×4 L+2 L brine) and saturated brine (2.5 L). The organic layer was dried over sodium sulfate and solvent was removed under reduced pressure. The residue was co-evaporated successively with toluene (2.50 L) and dichloromethane (6 L). The residue was dried under high vacuum overnight to obtain the compound 24A as a pale yellow gummy liquid (2026 g, 30 g more than quantitative yield, contaminated with small amount of HOBt and water). $^1$H NMR (400 MHz, DMSO-d$_6$): δ 7.79 (t, J=5.6 Hz, 1H), 6.94 (s, 1H), 6.72 (t, J=5.3 Hz, 1H), 3.61-3.45 (m, 5H), 3.01 (dd, J=12.8, 6.6 Hz, 2H), 2.89 (dd, J=12.7, 6.5 Hz, 2H), 2.26 (t, J=6.3 Hz, 3H), 2.03 (t, J=7.3 Hz, 1H), 1.55-1.38 (m, 3H), 1.36 (d, J=10.7 Hz, 8H), 1.21 (s, 3H). MS calc for C$_{50}$H$_{93}$N$_7$O$_{15}$: 1031.67. found 1032.6 (M+H).

Example 13

Synthesis of Triamine Trifluoroacetic Acid Salt 25A

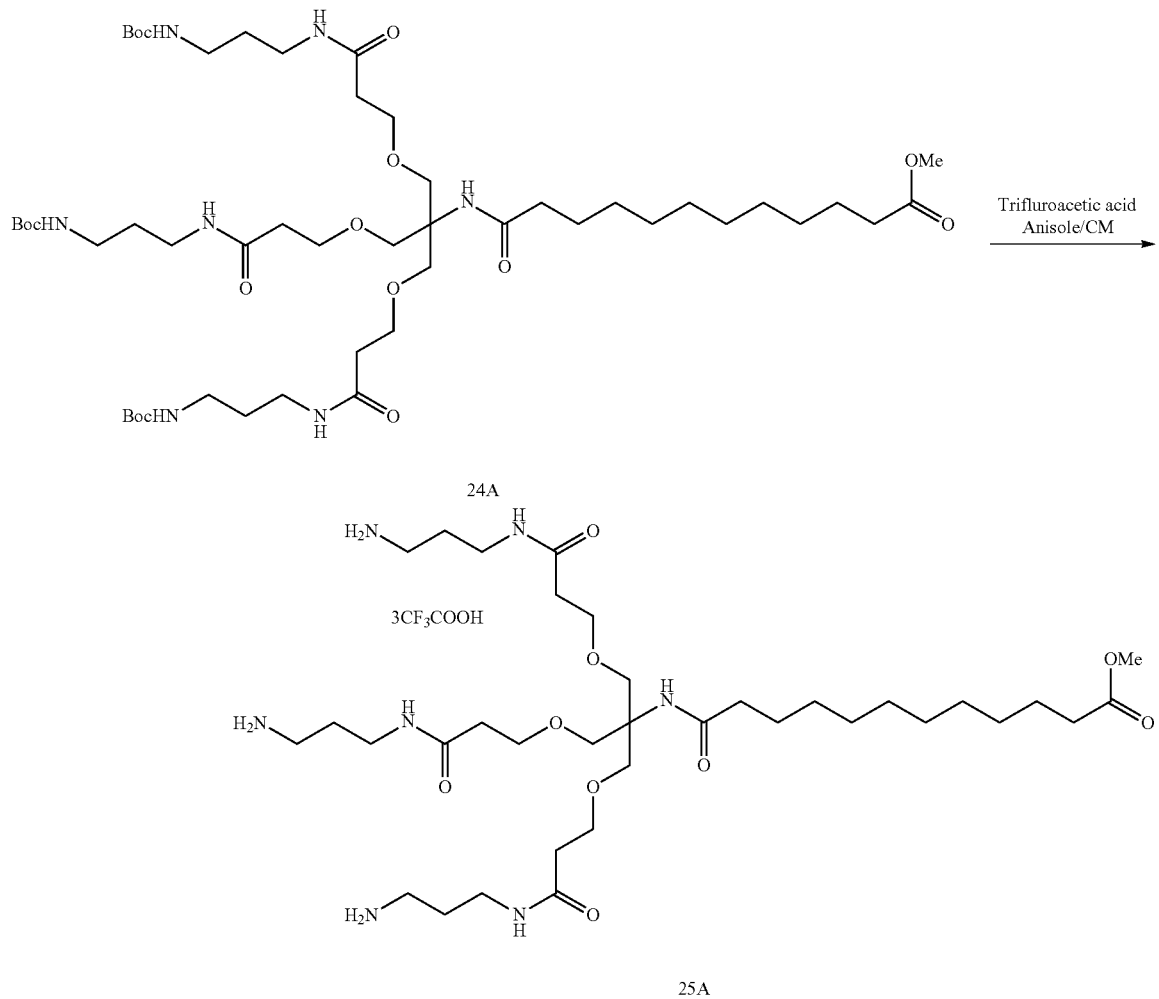

| | Reagents | MW | Qty Used | Moles | Mol Eq. |
|---|---|---|---|---|---|
| 1 | Tris($^{Boc}$Amine) Methyl Ester 24A | 1031.67 | 750 g | 0.727 | 1 |
| 2 | Anisole | — | 250 mL | — | — |
| 3 | Trifluoroacetic acid | — | 3.5 L | — | — |
| 4 | Anhyd. DCM | — | 2.5 L | — | Solvent |
| 5 | Anhyd. Toluene | | 4 L | | Solvent |
| 6 | Methanol | | 1 L | | Solvent |
| 7 | Anhyd. Ether | | 8 L | | Solvent |

Compound 24A (1990 g, gummy liquid) from the previous step was dissolved in 4 L DCM in the rotary evaporator flask. Weight of the mixture was determined and transferred the required amount of solution to another 20 L rotary evaporator flask for this reaction. DCM was removed under reduced pressure and the residue was dried under high vacuum overnight. After overnight drying the residue 24A (750 g, 727 mmol) was dissolved in anhydrous DCM (2 L) and transferred to a 12 L four necked flask equipped with an overhead stirred under argon. The rotary evaporator flask was washed with 500 mL DCM and transferred that solution also to the reaction flask. Anisole (250 mL) was added to the reaction mixture followed by trifluoroacetic acid (3.5 L) with stirring. During addition of trifluoroacetic acid strong effervescence occurred due to the liberation of butylene gas, a byproduct from the reaction. The reaction mixture was stirred at ambient temperature overnight. Completion of the reaction was monitored by MS analysis. The mixture was transferred to a 20 L rotary evaporator flask and volatiles were under reduced pressure. The residue was co-evaporated with anhydrous toluene (2×2 L) to get a pale brown gummy liquid. The flask was transferred to a hood and connected to an overhead stirrer. The residue was dissolved in anhydrous MeOH (1 L); anhydrous ether (8 L) was added to the solution under constant stirring. During the addition of ether the solution turned milky and a gummy mass was separated out in the bottom of the flask. The flask was kept in the cold room (~4° C.) overnight to settle the entire product on the wall and bottom of the flask. The top layer was decanted and the residue containing flask was transferred to the rotary evaporator; evaporated residual solvent under reduced pressure and dried the residue under high vacuum overnight to get the compound 25A as white fluffy solid, which upon removal of vacuum turned to a gummy colorless liquid (789 g, 9 g more than quantitative yield). $^1$H NMR (400 MHz, DMSO-$d_6$): δ 8.06 (t, J=5.6 Hz, 1H), 7.85 (s, 3H), 6.99 (s, 1H), 3.66-3.42 (m, 4H), 3.21-3.00 (m, 2H), 2.89-2.68 (m, 2H), 2.28 (dt, J=12.4, 6.9 Hz, 2H), 2.04 (t, J=7.3 Hz, 1H), 1.76-1.59 (m, 2H), 1.56-1.35 (m, 1H), 1.21 (s, 3H). MS calc for $C_{35}H_{69}N_7O_9$: 731.52. found 732.50 (M+H).

Example 14
Synthesis of Tris($^{Bz}$GalNAc)-Methyl Ester 26B
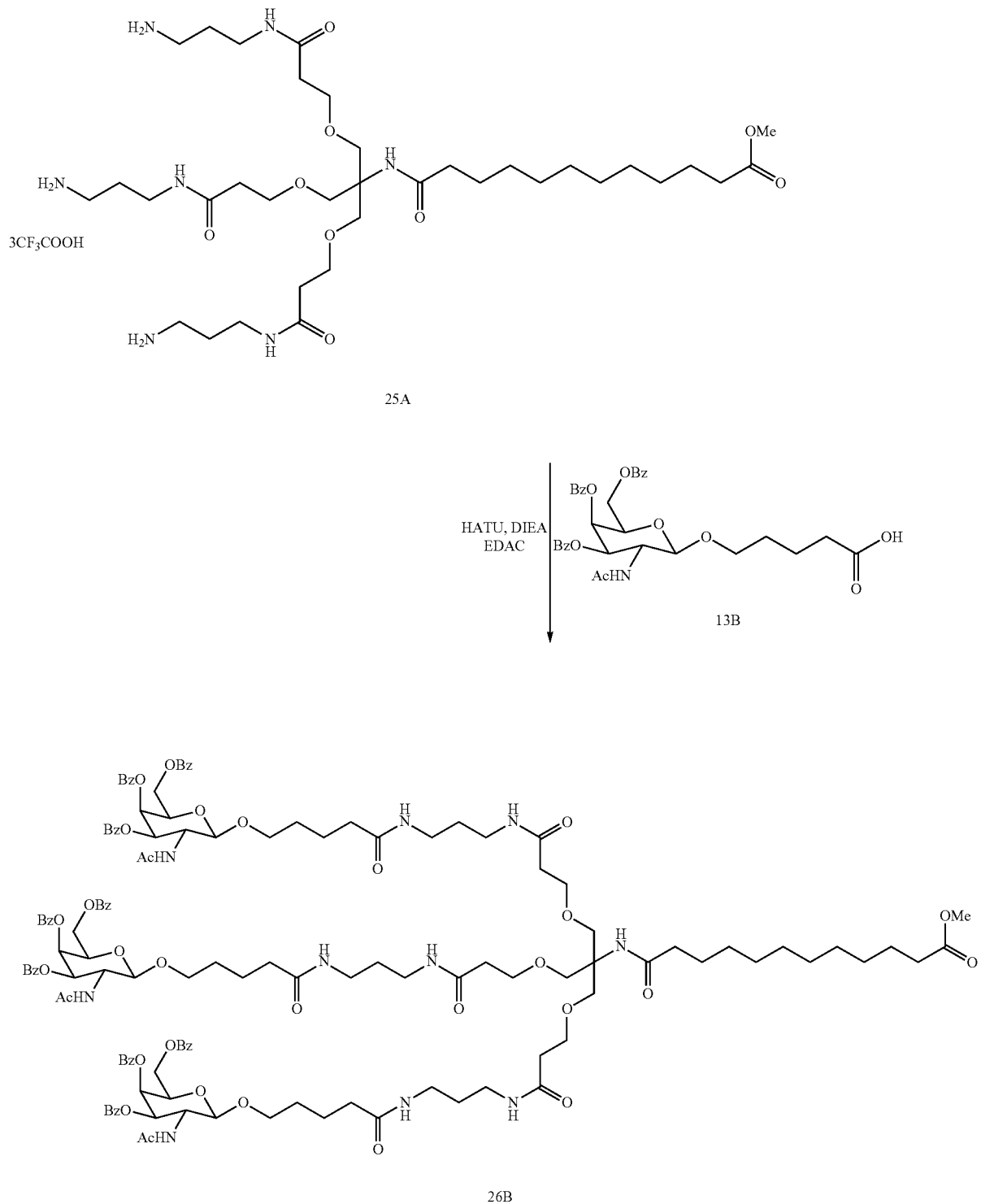

| | Reagents | MW | Qty Used | Moles | Mol Eq.t |
|---|---|---|---|---|---|
| 1 | Triamine trifluoroacetic acid salt 25A | 1031.67 | 776 g | 0.722 | 1.00 |
| 2 | $^{Bz}$GalNAc C$_5$ Acid_sodium salt 13B | 633.92 | 1570 g | 2.476 | 3.42 |
| 3 | EDAC•HCl | 198.24 | 576 g | 2.904 | 4.00 |
| 4 | HOBt | 135.1 | 490 g | 3.630 | 5.00 |
| 5 | DIEA | 129.1 | 1260 mL | 7.260 | 10.00 |
| 6 | Anhyd. DCM | — | 6 L | — | Solvent |
| 7 | Anhyd. DMF | — | 7 L | — | Solvent |
| 8 | 20% Phosphoric acid solution | | 1 L | | Solvent |
| 9 | Ethyl acetate | | ~90 L | | Solvent |
| 10 | Methanol | | ~15 L | | Solvent |

Triamine trifluoroacetic acid salt 25A (776 g, 0.7228 moles) was dissolved in 2 L of anhydrous DMF in a 20 L rotary evaporator flask. Compound 13B (1570 g, 2.476 moles) and HOBt (490 g, 3.630 moles) were charged to a 22 L four necked flask equipped with an overhead stirrer under argon. To the above mixture 4 L of DCM and 2 L of DMF were added and stirred until most of the solid went into solution (30 min, slight turbidity persists). The flask was cooled over an ice-water mixture to about 10° C. Slurry of EDAC.HCl (576 g, 2.904 moles) in 2 L DMF was added followed by DIEA (1260 mL) using an addition funnel over a period of 15-20 minutes while maintaining the temperature ~10° C. To the above mixture the solution of 25A in DMF was added slowly and rinsed the flask with 1 L of DMF and transferred this solution also to the reaction mixture. The reaction mixture was slowly warmed to ambient temperature and continued stirring overnight. The color of the solution changed from pale yellow to pale brown overnight. TLC checked and the reaction mixture was transferred to a 20 L rotary evaporator to remove most of the volatiles. The reaction mixture was divided into approximately two halves and added 12 L of ice-cold water with vigorous stirring to each of those portions. Solid was precipitated out during the addition of water and the solution was kept in the cold room overnight. Two layers separated with pale yellow solution on the top and light brown precipitate at the bottom. The top layer was decanted using a transfer pump and the residue was dissolved in EtOAc (9 L). This solution was washed successively with a mixture of 5% NaCl (5 L) and 20% H$_3$PO$_4$ (1 L), 5% NaCl (2×6 L), and sat. NaCl (3.5 L). The organic layer was separated, diluted with EtOAc to 20 L, and dried over anhyd. sodium sulfate. This solution was directly loaded on a filtration column of 7.5 kg of silica gel (EMD, grade 62, 60-200 mesh) wet preloaded with EtOAc in a 20 L funnel. The column was eluted with 40 L of EtOAc (1-st 12 L were pure solvent and reused), followed by 20 L of 20:1 EtOAc-methanol and 60 L of 3:1 EtOAc-methanol. EtOAc-methanol (3:1) fractions containing the product were collected, evaporated and the residue was dried at 2 mbar/35° C. overnight to afford 1.51 kg (82%) of 26B as off-white foam. $^1$H NMR (400 MHz, DMSO-d$_6$): δ 8.00 (d, J=9.3 Hz, 3H), 7.96-7.80 (m, 15H), 7.80-7.43 (m, 30H), 7.37 (t, J=7.8 Hz, 6H), 6.98 (s, 1H), 5.76 (d, J=3.2 Hz, 3H), 5.37 (dd, J=11.1, 3.2 Hz, 3H), 4.74 (d, J=8.5 Hz, 3H), 4.55-4.40 (m, 6H), 4.40-4.20 (m, 6H), 4.01 (q, J=7.1 Hz, 3H), 3.89-3.73 (m, 3H), 3.66-3.42 (m, 18H), 3.34 (s, 2H), 3.03 (s, 12H), 2.35-2.17 (m, 8H), 2.13-2.00 (m, 8H), 1.70 (s, 9H), 1.61-1.33 (m, 21H), 1.16 (dd, J=12.4, 5.2 Hz, 15H).

Example 15

Synthesis of Tris($^{Ac}$GalNAc)-Acid 27A

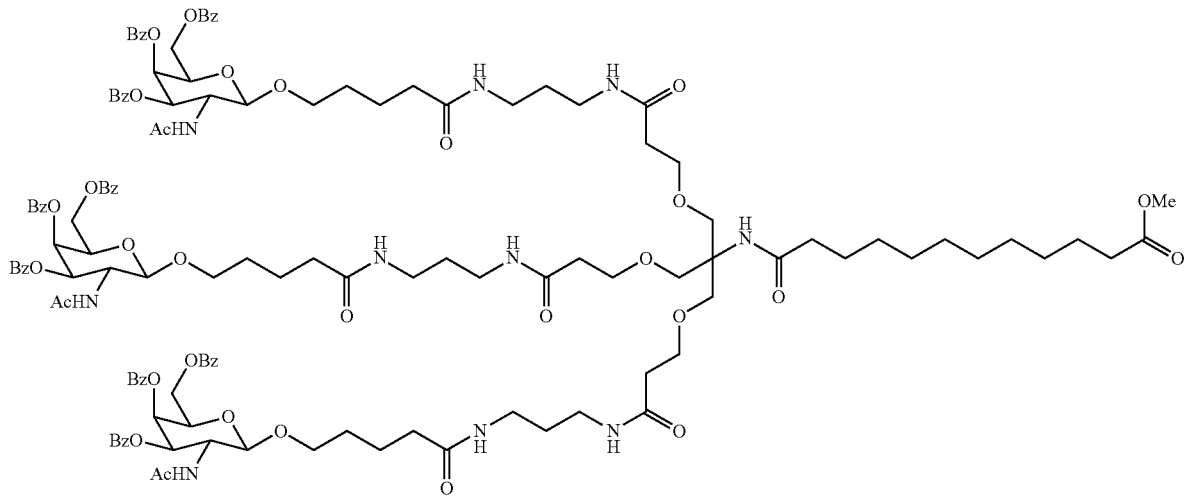

26B

1. NaOMe/MeOH

-continued
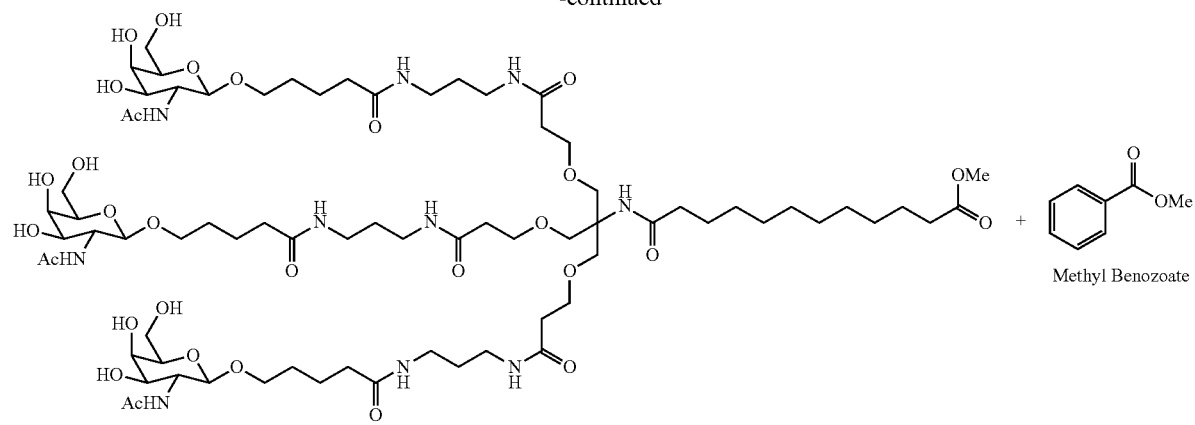
26B-1
↓ 2. NaOMe/MeOH
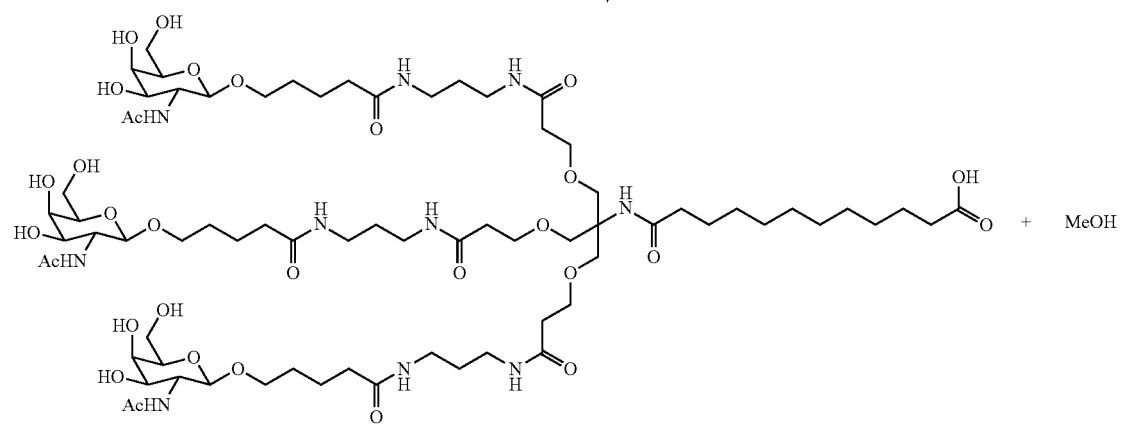  + MeOH
26B-2
↓ 3. Ac₂O/Pyridine
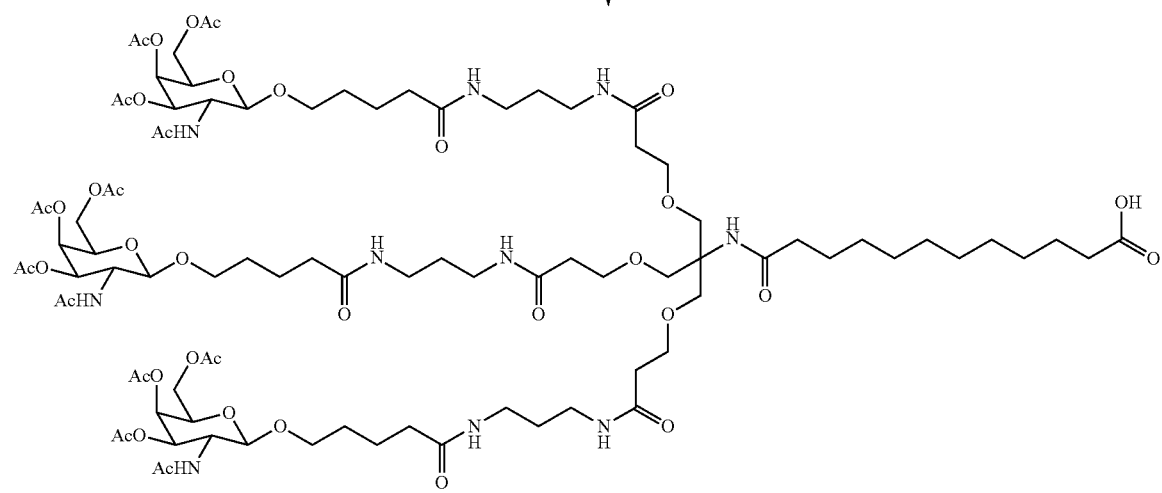
27A

| Reagents | MW | Qty Used | Moles | Mol Eq. |
|---|---|---|---|---|
| 1 Tris($^{Bz}$GalNAc)-Methyl ester 26B | 2578.84 | 1.51 Kg | 0.585 | 1 |
| 2 25% Sodium methoxide in methanol | — | 135 mL | 0.585 | 1 |
| 3 Triethylamine hydrochloride | 137.65 | 337.30 g | 2.45 | 4.18 |
| 4 Sodium hydroxide | 40.00 | 70.00 g | 1.75 | 3.00 |
| 5 Acetic anhydride | 102.09 | 2.80 L | — | — |
| 6 Anhydrous methanol | — | 6.5 L | — | Solvent |
| 7 Pyridine | — | 15.5 L | — | Solvent |
| 8 Anhyd. Pyridine | — | 12 L | — | Solvent |
| 9 Ethyl acetate | | 10 L | | Solvent |
| 10 Isopropanol | | 1.5 L | | Solvent |
| 11 Triethylamine | | 1 L | | — |

Step 1

To a solution of Tri-GalNAc(Bz)-Methyl ester 26B (1.51 kg, 0.585 mol) in anhyd. methanol (6.5 L) was added 25 wt % solution of NaOMe in methanol (135 mL, 0.585 mol) under Ar atm. The mixture was stirred at ambient temperature for 2 h, neutralized with triethylamine hydrochloride (96.3 g, 0.70 mol), evaporated under reduced pressure, and the residue was partitioned between 1% aq. NaCl (7.0 L) and EtOAc (3.0 L) in a separatory funnel to extract out methyl benzoate (side product) into the organic layer (de-benzoylated product 26B-1 is highly soluble in water). The EtOAc layer was separated and the aqueous layer was washed with additional 3.0 L of ethyl acetate. Pyridine (2.0 L) was added to the aqueous extract, and the mixture was evaporated on the rotary evaporator at 40 mbar/35° C. until all traces of ethyl acetate have been removed (~2 h).

Step 2

The rotary evaporator flask containing water extract from the previous step was equipped with an overhead stirrer, NaOH (70.0 g, 1.75 mol) was added and the mixture was stirred overnight at ambient temperature, neutralized with triethylamine hydrochloride (241 g, 1.75 mol), diluted with 6.0 L of pyridine, and the solvents were evaporated at 13 mbar/35° C. on a 20 L rotary evaporator till viscous oily residue. The residue was re-dissolved in pyridine (6.0 L), precipitated sodium chloride was filtered off, washed with pyridine (3×500 mL), and the combined filtrates were evaporated at 20 mbar/45° C. till viscous oily residue.

Step 3

The residue from Step 2 was re-dissolved in anhyd. pyridine (6.0 L) under Ar atm and the solution was slowly added to a vigorously stirred mixture of anhyd. pyridine (5.6 L) and acetic anhydride (2.8 L) for about 1.5 h. The mixture was stirred at ambient temperature overnight, cooled in an ice-water bath to ~4° C. and 1.5 L of ice cold water was added. Exothermic effect up to 40° C. was observed; the mixture was allowed to cool to ambient temperature (~0.5 h) and transferred to a rotary evaporator to remove the volatiles. The oily residue was dried under vacuum at 2 mbar/45° C. till constant weight (~1.82 Kg). The residue was dissolved in a stirred mixture of ethyl acetate (5.0 L) and isopropanol (1.0 L), and 25% aq. sodium chloride (6.0 L) was added. The pH of the aq. phase was adjusted to 7 by slow addition of triethylamine (1.025 L). Neutralization was accompanied with precipitation of solid sodium chloride and separation of an intermediate layer, which was taken back into the organic phase by the addition of 0.5 L of isopropanol. The liquids were decanted from solid NaCl to a separatory funnel using a transfer pump. Organic layer was separated, washed with 25% NaCl (6.0 L×2), sat. NaCl (3.0 L), dried over anhyd. sodium sulfate, the solvents were evaporated, the foamy residue was co-evaporated with anhydrous acetonitrile (6.0 L×2), and dried at 2 mbar/40° C. for 24 h to afford 1.11 kg (95%) of 27A. $^1$H NMR (400 MHz, DMSO-d$_6$): δ 8.00 (d, J=9.3 Hz, 3H), 7.96-7.80 (m, 15H), 7.80-7.43 (m, 30H), 7.37 (t, J=7.8 Hz, 6H), 6.98 (s, 1H), 5.76 (d, J=3.2 Hz, 3H), 5.37 (dd, J=11.1, 3.2 Hz, 3H), 4.74 (d, J=8.5 Hz, 3H), 4.55-4.40 (m, 6H), 4.40-4.20 (m, 6H), 4.01 (q, J=7.1 Hz, 3H), 3.89-3.73 (m, 3H), 3.66-3.42 (m, 18H), 3.34 (s, 2H), 3.03 (s, 12H), 2.35-2.17 (m, 8H), 2.13-2.00 (m, 8H), 1.70 (s, 9H), 1.61-1.33 (m, 21H), 1.16 (dd, J=12.4, 5.2 Hz, 15H).

Example 16

Synthesis of Hyp-Tris($^{Ac}$GalNAc) 29A

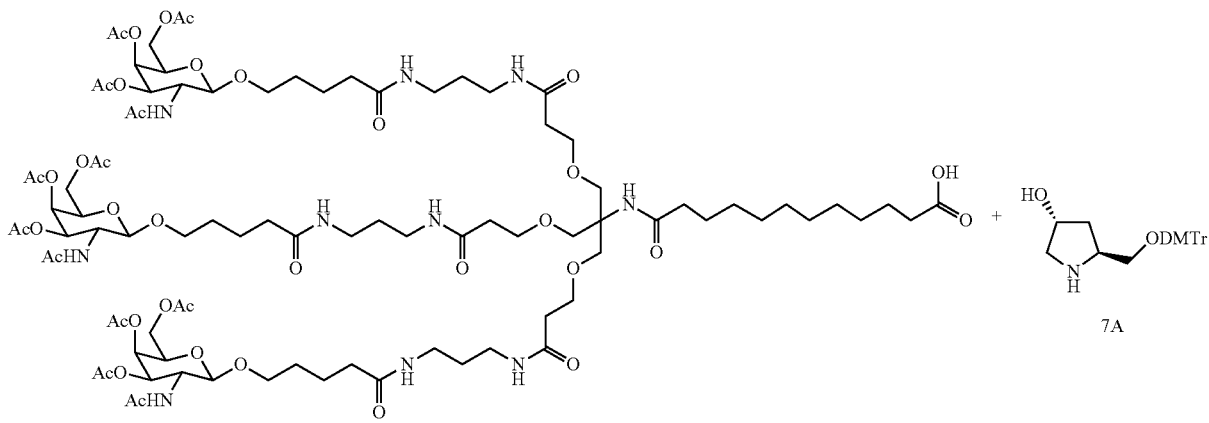

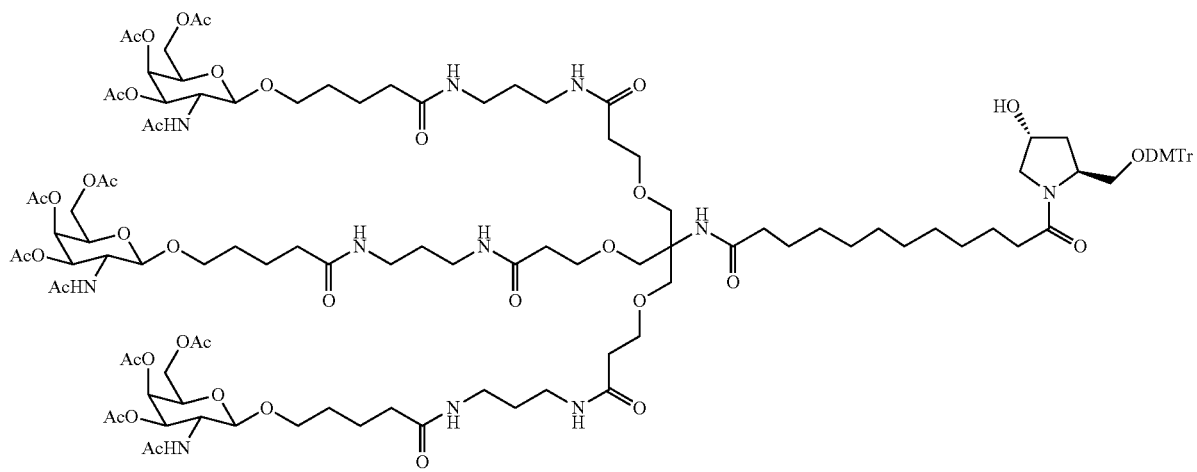

29A

| | Reagents | MW | Qty Used | Moles | Mol Eq. |
|---|---|---|---|---|---|
| 1 | Tris($^{Ac}$GalNAc)-acid 27A | 2006.19 | 1.107 Kg | 0.552 | 1 |
| 2 | Hydroxyprolinol derivative 7A | 419.51 | 256.00 g | 0.610 | 1.10 |
| 3 | HOBt monohydrate | 135.10 | 168.00 g | 1.10 | 2.00 |
| 4 | HBTU | 379.3 | 250.00 g | 0.66 | 1.20 |
| 5 | DIEA | 129.24 | 286.00 mL | 1.65 | 3.00 |
| 6 | Anhyd. DCM | — | 10 L | — | Solvent |
| 7 | Ethyl acetate | | 75 L | | Solvent |
| 8 | Isopropanol | | 10 L | | Solvent |
| 9 | Methanol | | 15 L | | Solvent |

To a stirred solution of triantennary GalNAc acid 27A (1.107 kg, 0.552 mol) in anhyd. DCM (10.0 L) in a four necked 22 L flask were added hydroxyprolinol derivative 7A (256 g, 0.61 mol), HOBt monohydrate (168 g, 1.1 mol) and HBTU (250 g, 0.66 mol) under argon atm. The mixture was stirred at ambient temperature for 15 min, DIEA (286 mL, 1.65 mol) was added, and the stirring was continued for additional 3 h. TLC was checked and the mixture was quenched with 4% aqueous NaHCO$_3$ (6.0 L), the organic layer was separated and concentrated under reduced pressure till a viscous gummy residue remained. The latter was partitioned between a mixture of ethyl acetate-isopropanol (5:1) (9.6 L) and 1% aq. NaCl (8.0 L), the organic layer was separated, washed with sat. NaCl solution (3.5 L), diluted to a total volume of 13 L with ethyl acetate-isopropanol (5:1) mixture, and dried over anhyd. Na$_2$SO$_4$. The dried solution was directly loaded on a filtration column of silica gel (7.2 kg, EMD 60-200 mesh) that was deactivated and wet-preloaded with 2% TEA in ethyl acetate. The column was eluted with ethyl acetate-isopropanol (5:1, 30 L) followed by ethyl acetate-methanol (2:1, 46 L). Small contaminated fraction (6 L) preceded main pure fractions were collected separately. Pure fractions were evaporated in vacuum, and foamy residue was re-dissolved and co-evaporated with anhydrous acetonitrile (6 L×2). The residue was dried overnight at 2 mbar/30° C. to afford 1.145 kg of 29A (87%). The contaminated fraction was evaporated and purified analogously on a small filtration column of silica gel (325 g) to afford additional 46 g of the material. Total yield of 29A: 1.19 kg, 90%. $^1$H NMR (400 MHz, DMSO-d$_6$): δ 7.82 (d, J=8.9 Hz, 2H), 7.73 (t, J=5.5 Hz, 1H), 7.37-7.24 (m, 1H), 7.24-7.11 (m, 2H), 6.97 (s, 1H), 6.93-6.80 (m, 1H), 5.20 (d, J=3.3 Hz, 1H), 5.01-4.85 (m, 1H), 4.48 (d, J=8.5 Hz, 1H), 4.42-4.23 (m, 1H), 4.13 (d, J=3.8 Hz, 1H), 4.06-3.96 (m, 3H), 3.86 (dd, J=19.9, 8.9 Hz, 1H), 3.77-3.64 (m, 3H), 3.62-3.46 (m, 5H), 3.46-3.28 (m, 2H), 3.15 (dd, J=8.7, 5.0 Hz, 1H), 3.11-2.92 (m, 6H), 2.34-2.15 (m, 3H), 2.09 (s, 3H), 2.08-2.00 (m, 5H), 1.98 (s, 3H), 1.91-1.85 (m, 3H), 1.76 (s, 3H), 1.48 (dd, J=17.3, 11.4, 6.3 Hz, 7H), 1.30-1.11 (m, 6H).

Example 17

Synthesis of Hyp-Tris($^{Ac}$GalNAc) Succinate 30

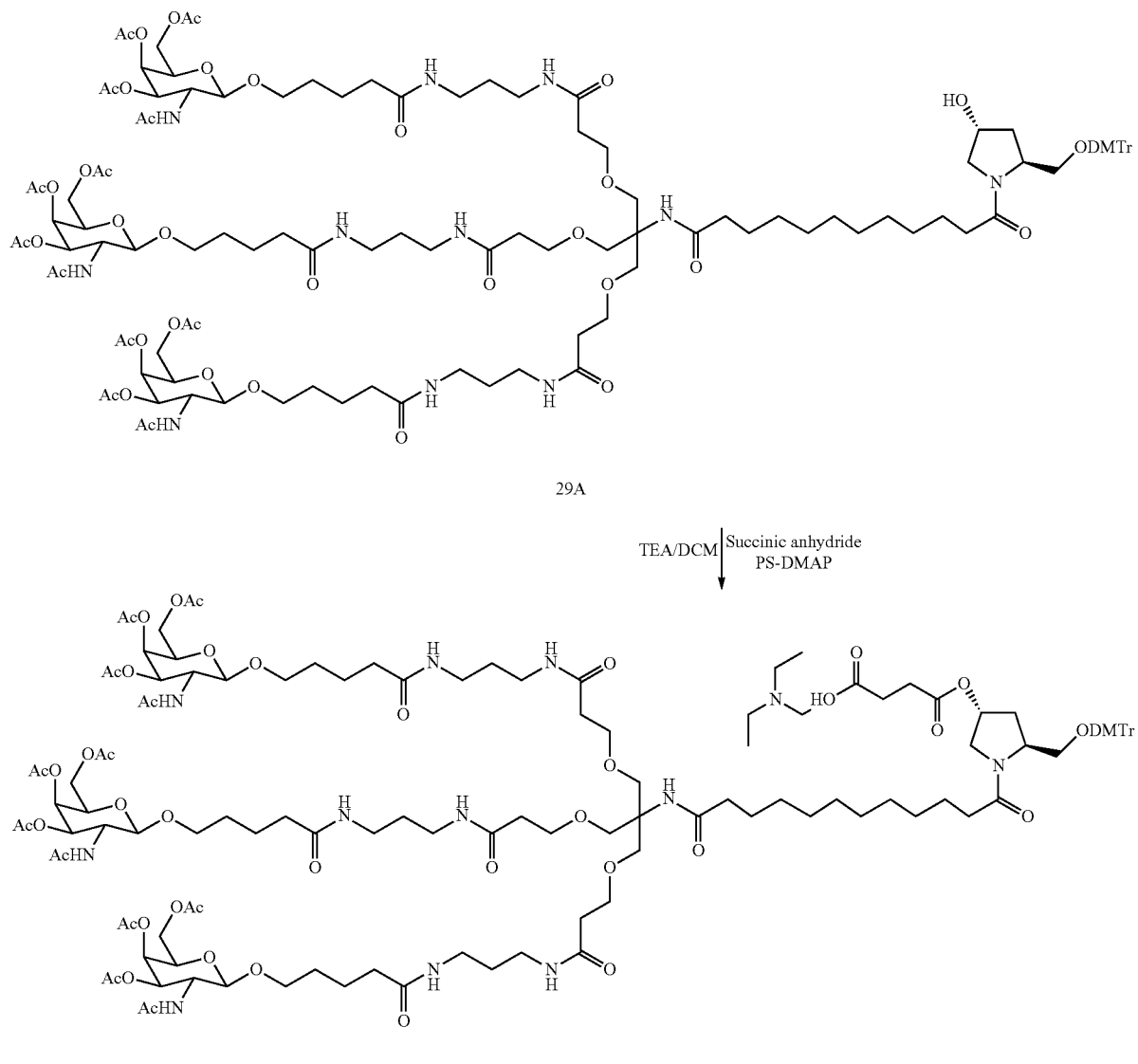

| | Reagents | MW | Qty Used | Moles | Mol Eq. |
|---|---|---|---|---|---|
| 1 | Hyp-AcGalNAc 29A | 2407.69 | 1.14 Kg | 0.474 | 1 |
| 2 | Succinic anhydride | 100.07 | 119.00 g | 1.189 | 2.50 |
| 3 | PS-DMAP(1.57 μmol/g loading) | — | 604 g | 0.948 | 2.00 |
| 4 | Triethylamine | 101.1 | 198 mL | 1.42 | 3.00 |
| 5 | Anhyd. DCM | — | 12 L | — | Solvent |
| 6 | DCM | — | 2 L | — | Solvent |

Succinic anhydride (94.8 g, 0.948 mol) and PS-DMAP (loading: 1.57 mmol/g, 604 g, 0.948 mol) were added successively to a solution of 29A (1.14 kg, 0.474 mol) and triethylamine (198 mL, 1.42 mol) in anhyd. DCM (6.0 L) in a 12 L four necked flask equipped with an overhead stirrer under argon atm. After stirring for 24 h, additional succinic anhydride (24 g, 0.24 mol) was added. The mixture was stirred for additional 24 h, filtered through wet-loaded in DCM Celite (0.5 kg), and the solids were washed thoroughly with DCM (8 L total). Combined filtrate (~14 L) was evaporated under reduced pressure to a volume of ~6 L. The mixture was transferred to a separatory funnel and triethylamine (200 mL) was added. The combined solution was washed with 5% aq. NaCl (6 L×2), the organic layer was separated, and dried over anhyd. $Na_2SO_4$. The solvent was evaporated on a 20 L rotary evaporator under reduced pressure till soft foamy residue which was re-dissolved in 6 L of anhyd. DCM containing 100 mL of triethylamine, the solvent was evaporated again, and the foamy residue thus obtained was dried at 1 mbar/20° C. for 2 days to afford 1.19 kg (96% based on triethylamine salt) of 30 as glassy foam. $^1$H NMR indicated presence of 4.3 mass % of residual solvents (DCM and traces of triethylamine). $^1$H NMR (400

MHz, DMSO-$d_6$): δ 7.93-7.72 (m, 1H), 7.28 (dd, J=13.3, 6.1 Hz, 1H), 7.24-7.12 (m, 1H), 6.99 (s, 1H), 6.94-6.80 (m, 1H), 5.33 (s, 1H), 5.20 (d, J=3.3 Hz, 1H), 4.96 (dd, J=11.2, 3.3 Hz, 1H), 4.48 (d, J=8.4 Hz, 1H), 4.18 (d, J=3.4 Hz, 1H), 4.10-3.95 (m, 1H), 3.86 (dd, J=19.8, 8.9 Hz, 1H), 3.79-3.62 (m, 1H), 3.61-3.45 (m, 1H), 3.45-3.32 (m, 1H), 3.26-3.15 (m, 1H), 3.13-2.94 (m, 1H), 2.41-2.13 (m, 1H), 2.09 (s, 1H), 2.03 (t, J=6.9 Hz, 1H), 1.98 (s, 1H), 1.88 (s, 1H), 1.76 (s, 1H), 1.57-1.35 (m, 2H), 1.31-1.06 (m, 2H), 0.93 (t, J=7.1 Hz, 1H).
Example 18
Alternative Method of Making Compound 18A—Replacing EDC/HOBt Coupling with Acid Chloride
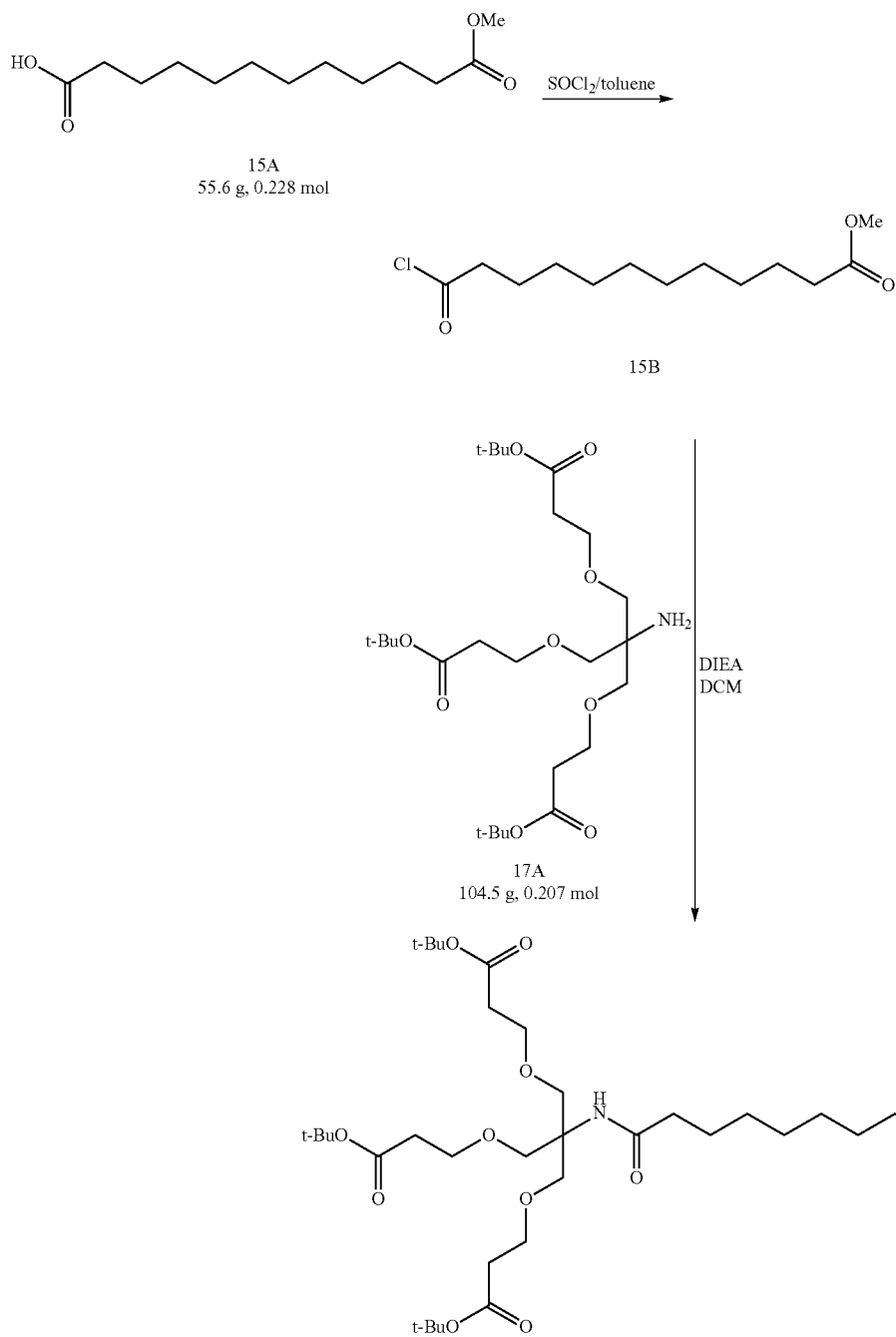

Thionyl chloride (low iron, 99%, 19.7 mL, 0.27 mol) was added to a suspension of dodecanedioic acid-monomethyl ester 15A (55.6 g, 0.228 mol) in anhyd. toluene (200 mL) and the mixture was stirred at 60° C. until gas evolution was completed (bubbler, 3 h). The mixture was cooled down to rt; solvent and volatiles were evaporated under reduced pressure, and the evaporation flask was refilled with argon. The residue (acid chloride 15B) was diluted with anhyd. DCM (200 mL) and transferred slowly via cannula over 40 min in a cooled (0° C.) and stirred solution of 17A (104.5 g, 0.207 mol) and DIEA (47 mL, 0.27 mol) in anhyd. DCM (500 mL). The stirring was continued at 0° C. for additional 30 min and the mixture was quenched by addition of sat. NaHCO$_3$ (400 mL). The organic phase was separated and concentrated under reduced pressure. The residue was dissolved in 1:1 mixture of ethyl acetate and hexane (600 mL) and washed consecutively with 600 mL of each: 2% aq. NaHCO$_3$, water, 5% aq. HCl, water (×2) (Note 2), sat. NaCl and dried over anhyd. Na$_2$SO$_4$. The solvents were removed under reduced pressure and the residue was dried by stirring at 0.4 torr overnight to afford 143.5 g (95%) of 18A.

Example 19

Synthesis of Triamine Tosic Acid Salt 25B 1) p-Toluenesulfonic Acid (PTSA or Tosic Acid) Deprotection of Tris($^{Boc}$Amine) Methyl ester 24A to the Corresponding Tosic Acid Salt 25B

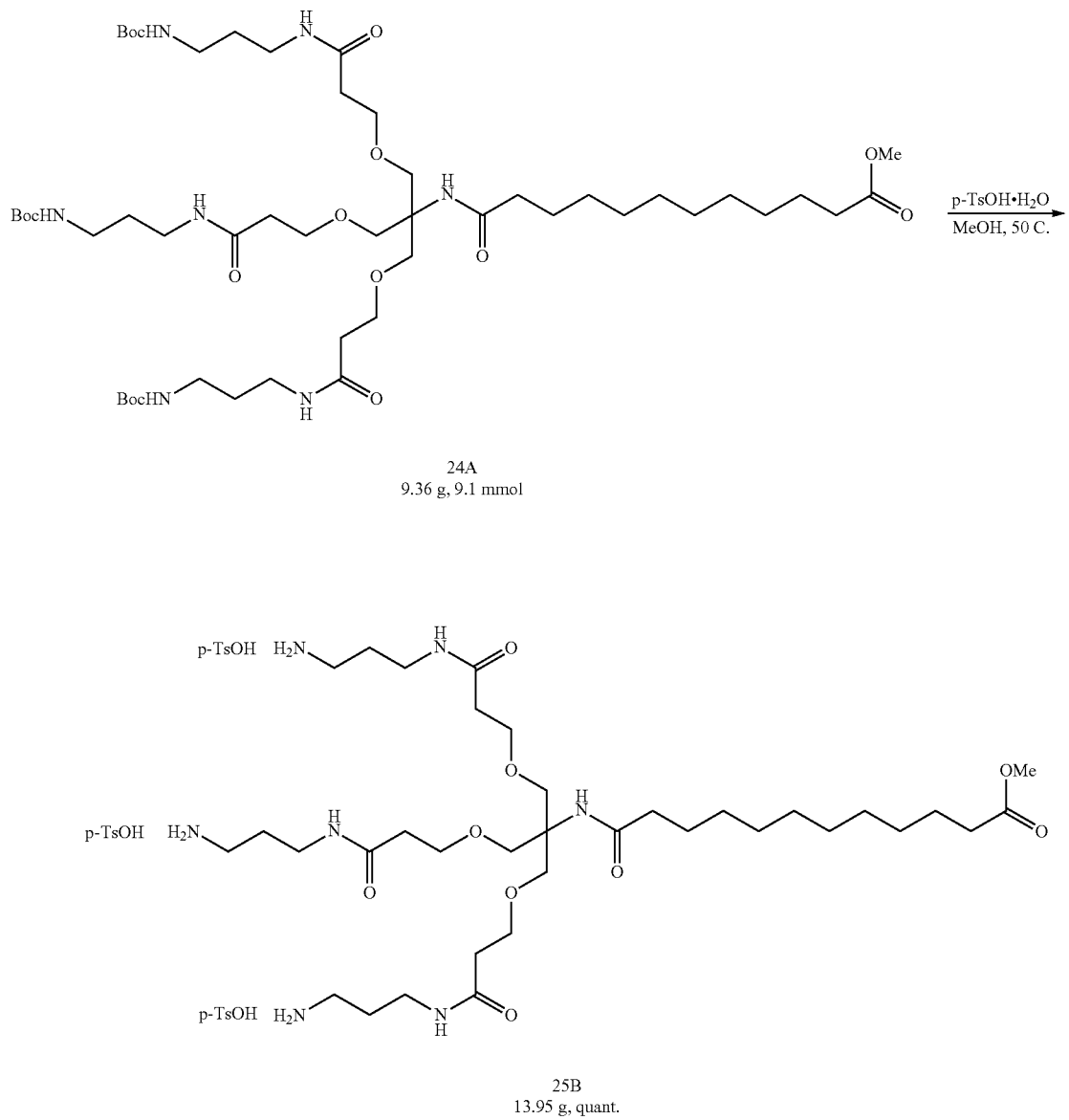

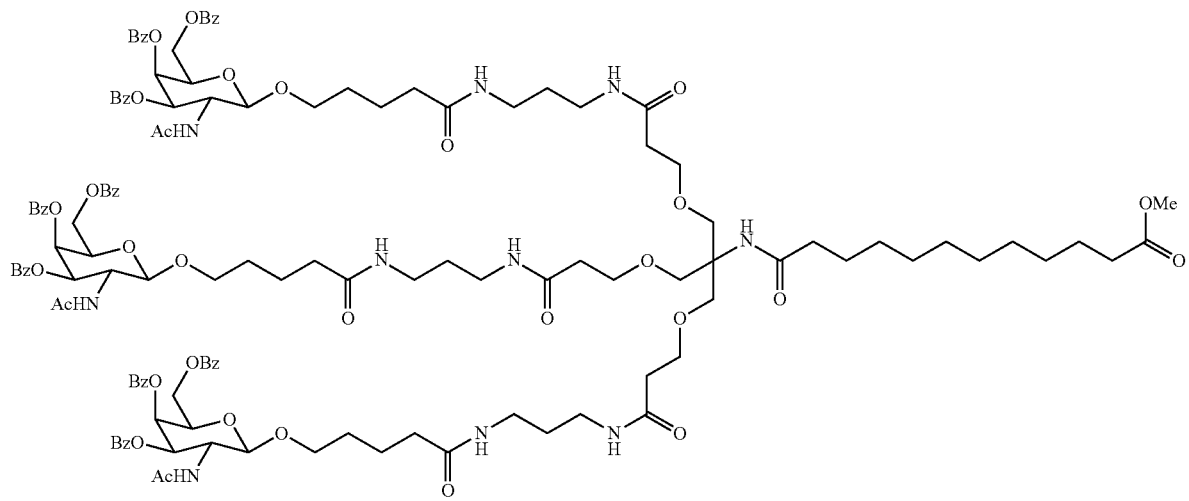

26A
20.14 g, 86% HPLC purity: 87%

A solution of Boc protected amine 24A (9.36 g, 9.1 mmol) and p-toluenesulfonic acid monohydrate (tosic acid, 6.23 g, 32.8 mmol) in dry methanol (90 mL) was heated in a moisture-protected flask at 50° C. overnight. The completion of the reaction was monitored by MS analysis. The mixture was cooled to rt, excess tosic acid was neutralized by addition of DIEA (0.96 mL, 5.5 mmol), and the mixture was diluted with toluene (180 mL). The solvents were evaporated and the foamy solid residue obtained was dried on rotary evaporator at 8 mbar/30° C. for 2 h to afford 13.95 g of 25B containing ~5.5 mmol (1.66 g) of p-TSA-DIEA salt and traces of residual toluene.
2) Triantennary Scaffold 26A from Triamine Tosic Acid Salt 25B To a cooled (10° C.) and stirred solution of $^{Bz}$GalNAc C$_5$ acid-sodium salt 13A (21.5 g, 32.8 mmol) and HOBt-monohydrate (5.51 g, 36 mmol) in anhyd. DMF (100 mL) was added EDC hydrochloride (7.1 g, 36 mmol) followed by DIEA (10.0 mL, 73 mmol), and the mixture was stirred at 10° C. till complete dissolution of EDC hydrochloride (~15 min). Concurrently, the solid from previous step containing 25B (13.95 g, 9.1 mmol) was dissolved in anhyd. DMF (70 mL) and the solution was transferred via cannula to the above mixture. The mixture was allowed to warm up to rt overnight, cooled to 0° C. and diluted with water (600 mL). After settling of the organic components down at 0° C. overnight, the water layer was decanted from viscous organic residue, the latter was taken in EtOAc (200 mL), washed successively with a mixture of 5% NaCl (200 mL), 20% phosphoric acid (20 mL), 5% brine (×2) and saturated brine; diluted the organic layer with EtOAc to a total volume of 300 mL and dried over anhyd. Na$_2$SO$_4$. This solution was directly loaded on a short filtration column of 100 g silica gel wet-preloaded in EtOAc. The column was eluted with EtOAc (300 mL×2) followed by 3;1 EtOAc-methanol (300 mL×3), fractions containing the desired product were pooled, evaporated and dried at 0.4 torr overnight to afford 20.14 g (86%) of 26A. HPLC profile (87%) was comparable to the reference batch (88%).

Example 20

Synthesis of Hyp-Tris($^{Ac}$GalNAc) Succinate 30—Succinylation in the Absence of DMAP or Immobilized DMAP (PS-DMAP)

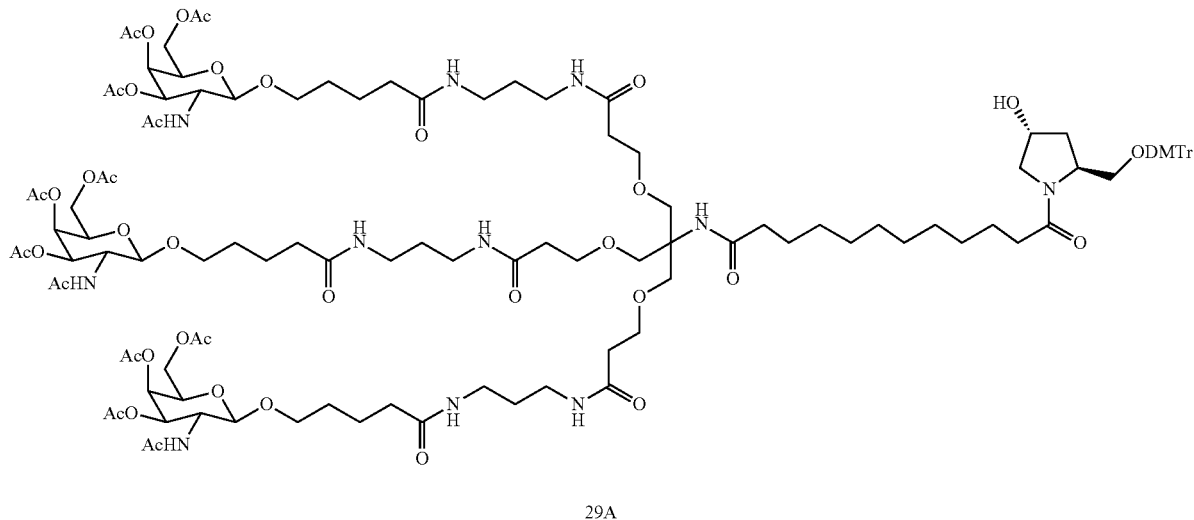

29A

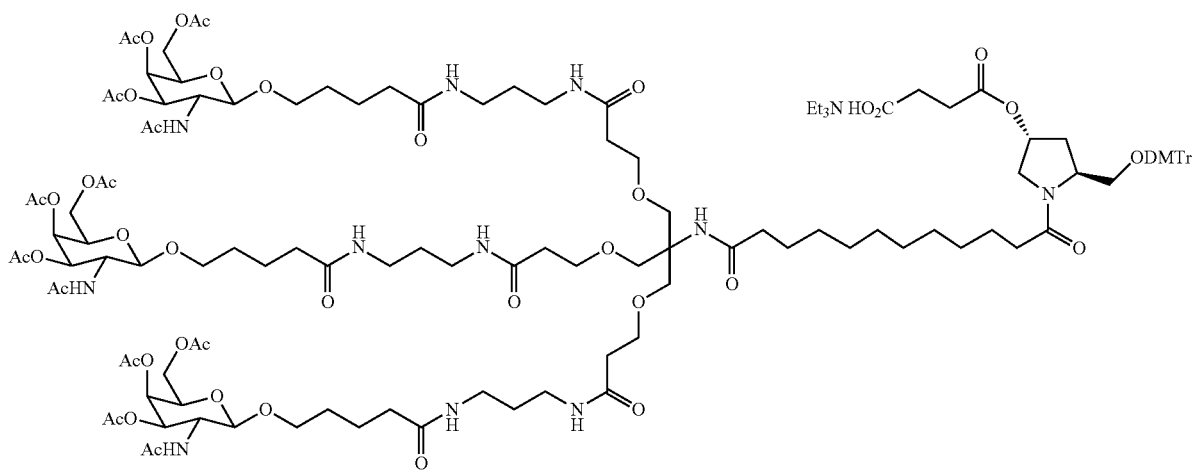

30

Succinic anhydride (1.18 g, 11.8 mmol) was added to a solution of 29A (11.4 g, 4.7 mmol) and triethylamine (1.95 mL, 14 mmol) in anhyd. DCM (60 mL) under Ar atm. The mixture was stirred at rt for 2 days, after which time TLC indicated complete conversion. The mixture was washed twice with 5% aq. NaCl (×2), the organic layer was dried over anhyd. Na$_2$SO$_4$ and the solvent was evaporated under reduced pressure. The residue was dried at 0.4 mbar/20° C. to afford 11.8 g (96% based on triethylamine salt) of 30. Diethylamine may also be used in place of triethyl amine, resulting in a less colored product.

What is claimed is:

1. A process for preparing a compound of formula (A):

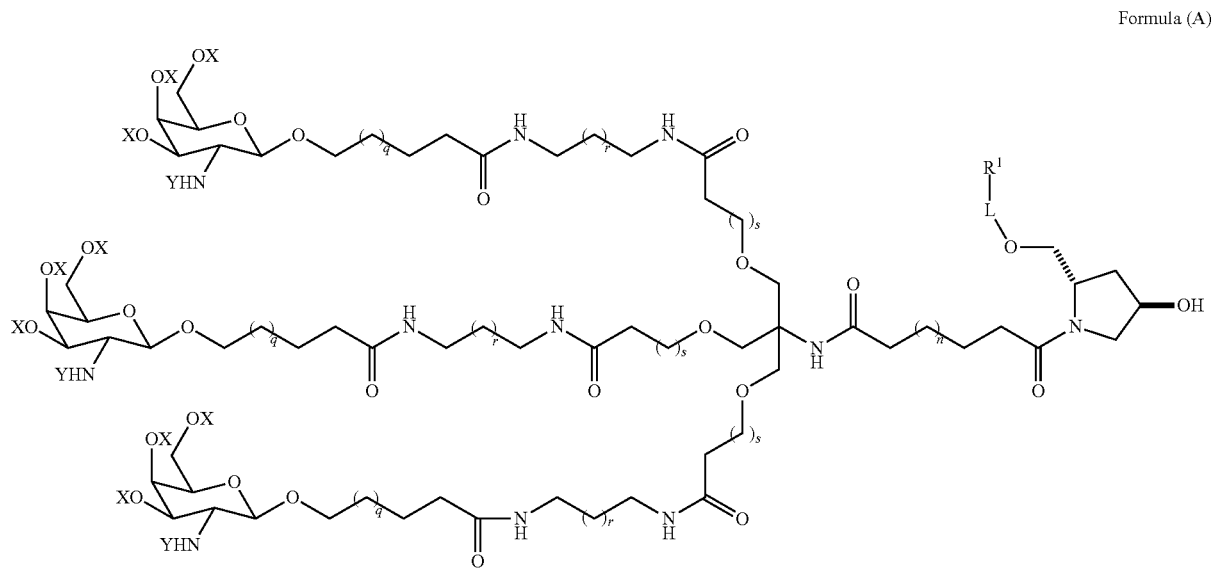

Formula (A)

wherein
each occurrence of X is hydrogen or a hydroxy protecting group;
each occurrence of Y is an amine protecting group;
n is 0-20;
each occurrence of q, r and s is independently 1-7;
L is a linking group; and
$R^1$ is an iRNA agent;
the process comprising
(a) converting a compound of formula (VI) to a compound of formula (VII):

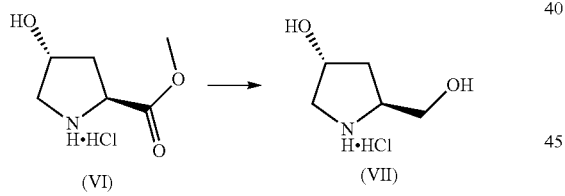

by a process comprising:
(i) reacting the compound of formula (VI) with a base;
(ii) reducing the product of step (i); and
(iii) reacting the product of step (ii) with an acid; and
(b) converting the compound of formula (VII) to a compound of formula (A);
wherein the compound of formula (A) is free or substantially free of one or more of
(i) metal impurities,
(ii) each of the following two urea side products

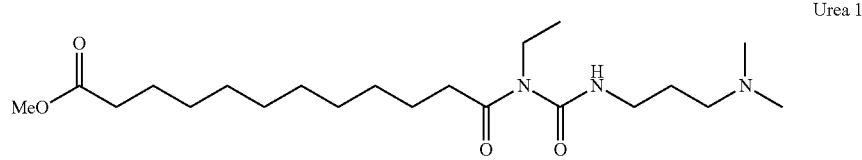

Urea 1

-continued

Urea 2

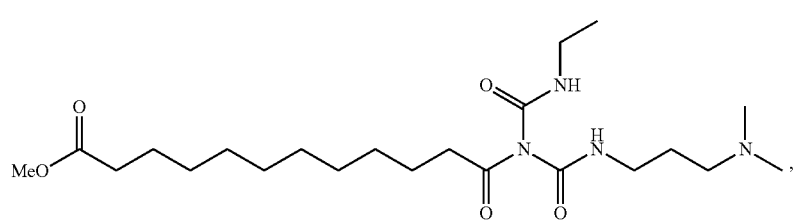

and
(iii) each of the following saccharide compounds

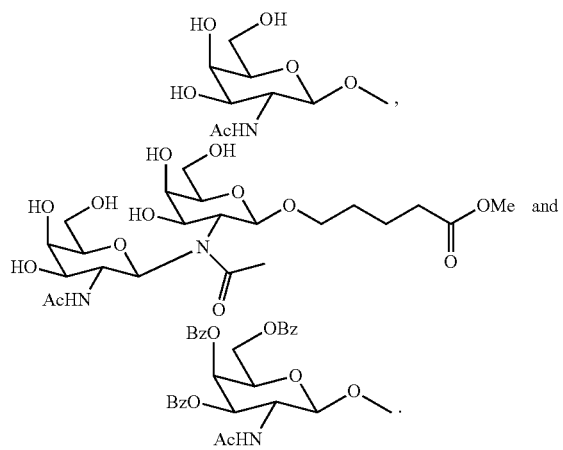

2. The process of claim 1, wherein the base is a metal alkoxide.

3. The process of claim 1, wherein the base is sodium methoxide, step (ii) involves reacting the product of step (i) with sodium borohydride, and the acid is hydrochloric acid.

4. A process for preparing a compound of formula (A):

wherein
each occurrence of X is hydrogen or a hydroxy protecting group;
each occurrence of Y is an amine protecting group;
n is 0-20;
each occurrence of q, r and s is independently 1-7;
L is a linking group; and
$R^1$ is an iRNA agent;
the process comprising
(a) reacting a compound of the formula (IX):

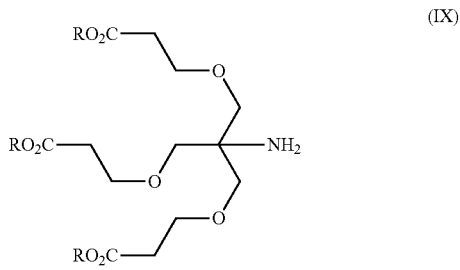

(IX)

Formula (A)

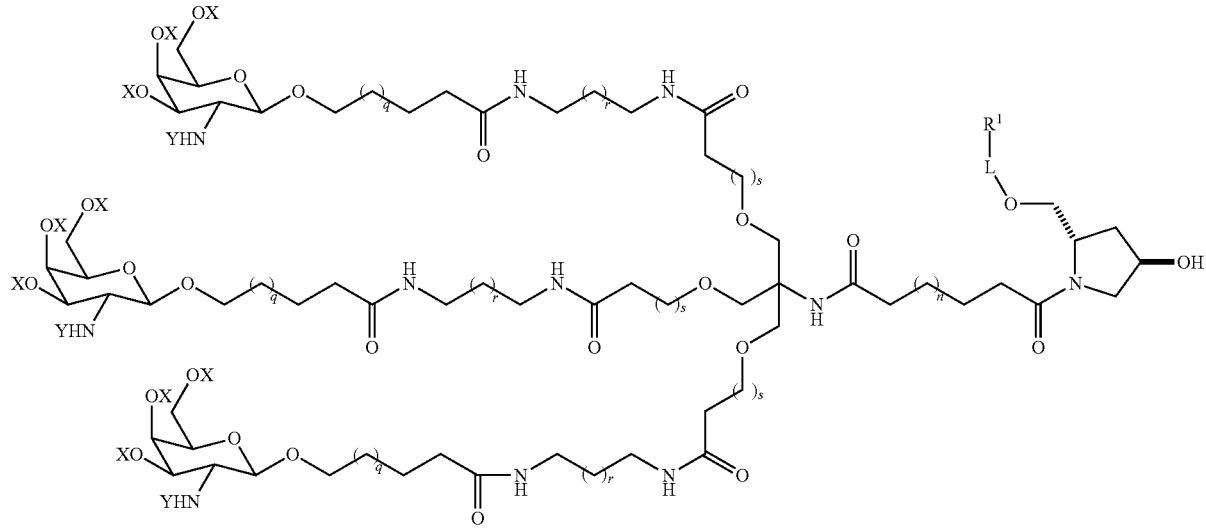

with a compound of the formula (X):

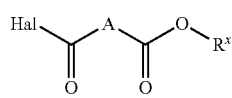

wherein Hal is halogen to yield a compound of formula (VIII)

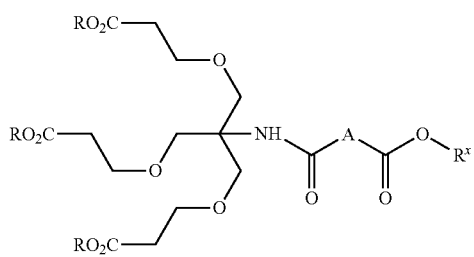

wherein
  A is a $C_6$-$C_{14}$ alkylene linker;
  each R is, independently, an acid protecting group; and
  $R^x$ is an acid protecting group; and
(b) converting the compound of formula (VIII) to a compound of formula (A);
wherein the compound of formula (A) is free or substantially free of one or more of
  (i) metal impurities,
  (ii) each of the following two urea side products and (iii) each of the following saccharide compounds

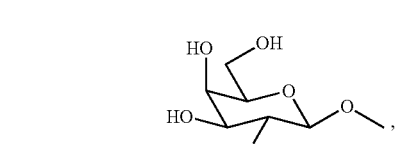

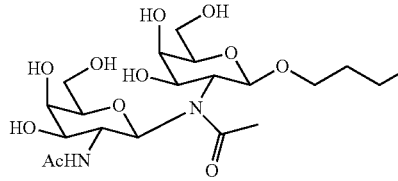

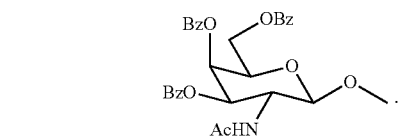

5. The process of claim 4, wherein R is t-butyl, Hal is Cl and A is a $C_{10}$ alkylene linker.

6. The process of claim 4, wherein the reaction is conducted in the presence of N,N-diisopropylethylamine.

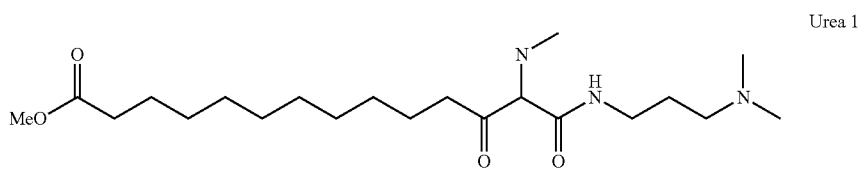

Urea 1

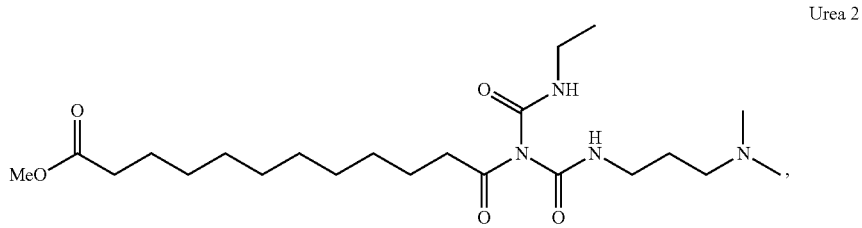

Urea 2

7. A process for preparing a compound of formula (A):

Formula (A)

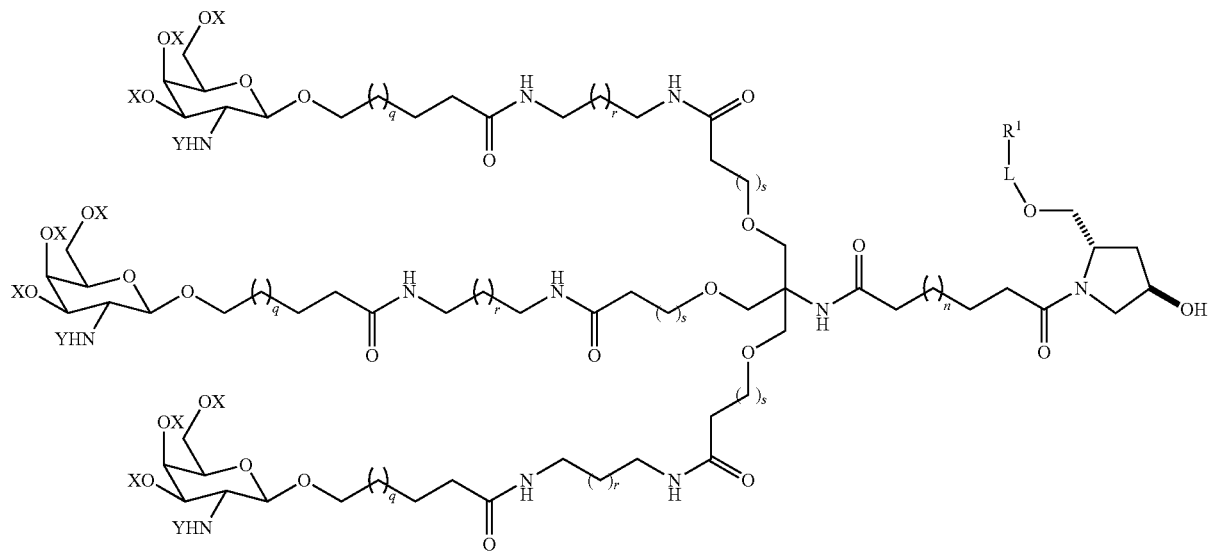

wherein
  each occurrence of X is hydrogen or a hydroxy protecting group;
  each occurrence of Y is an amine protecting group;
  n is 0-20;
  each occurrence of q, r and s is independently 1-7;
  L is a linking group; and
  R¹ is an iRNA agent;
the process comprising:
  a) reacting a compound of the formula (XII):

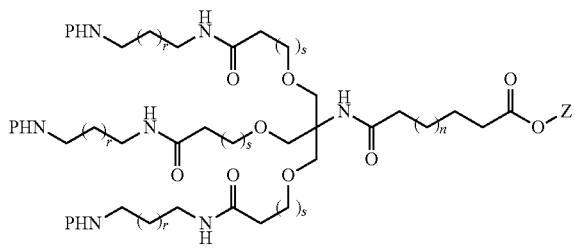

(XII)

wherein P is an amino protecting group with a sulfonic acid to give a compound of formula (II):

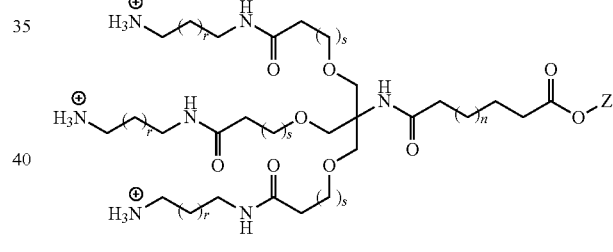

(II)

wherein
  Z is an acid protecting group,
  n is 0-20, and
  each occurrence of q, r and s is independently 1-7; and
  b) converting the compound of formula (II) to a compound of formula (A);
  wherein the compound of formula (A) is free or substantially free of one or more of
    (i) metal impurities,
    (ii) each of the following two urea side products Urea 1

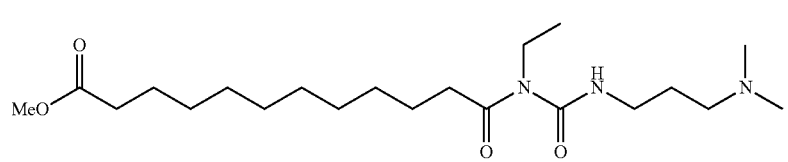

-continued

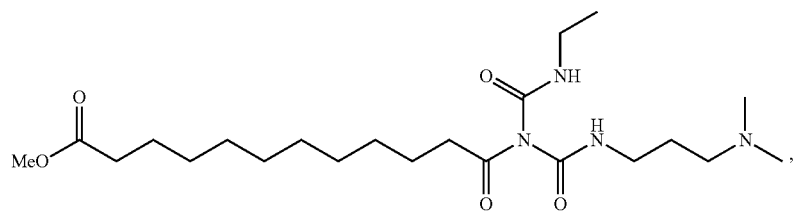

Urea 2 and
(iii) each of the following saccharide compounds

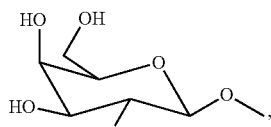

15

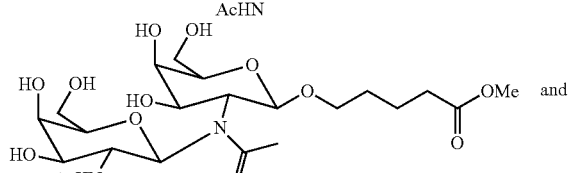
and

20

25

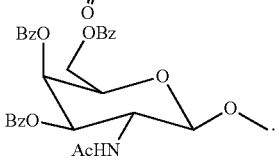

30

8. The process of claim 7, wherein the sulfonic acid is p-toluene sulfonic acid or methanesulfonic acid.

9. A process for preparing a compound of formula (A):

Formula (A)

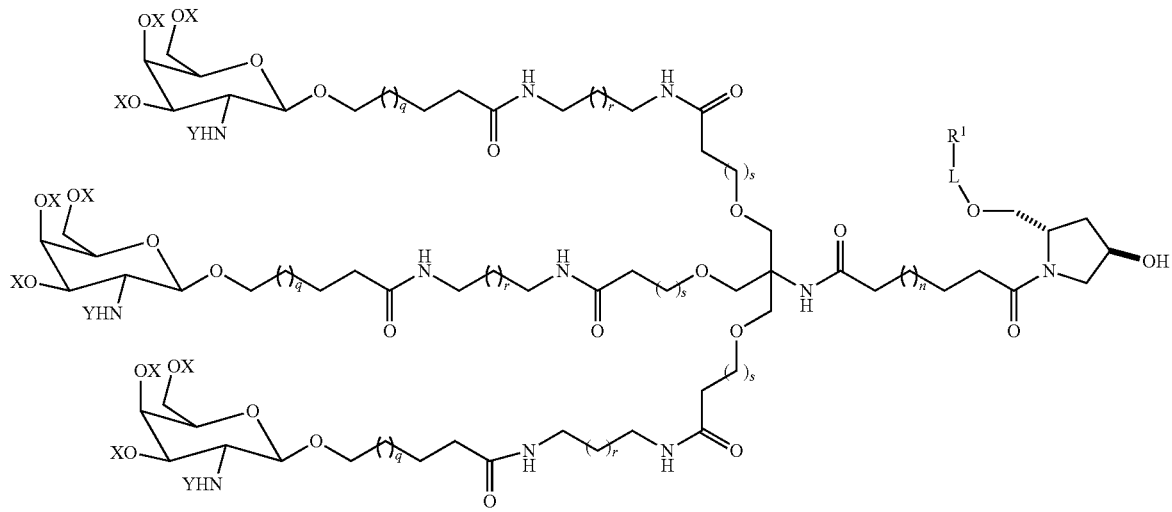

wherein
each occurrence of X is hydrogen or a hydroxy protecting group;
each occurrence of Y is an amine protecting group;
n is 0-20;
each occurrence of q, r and s is independently 1-7;
L is a linking group; and
$R^1$ is an iRNA agent;

the process comprising:
a) reacting a compound of formula (XIV)

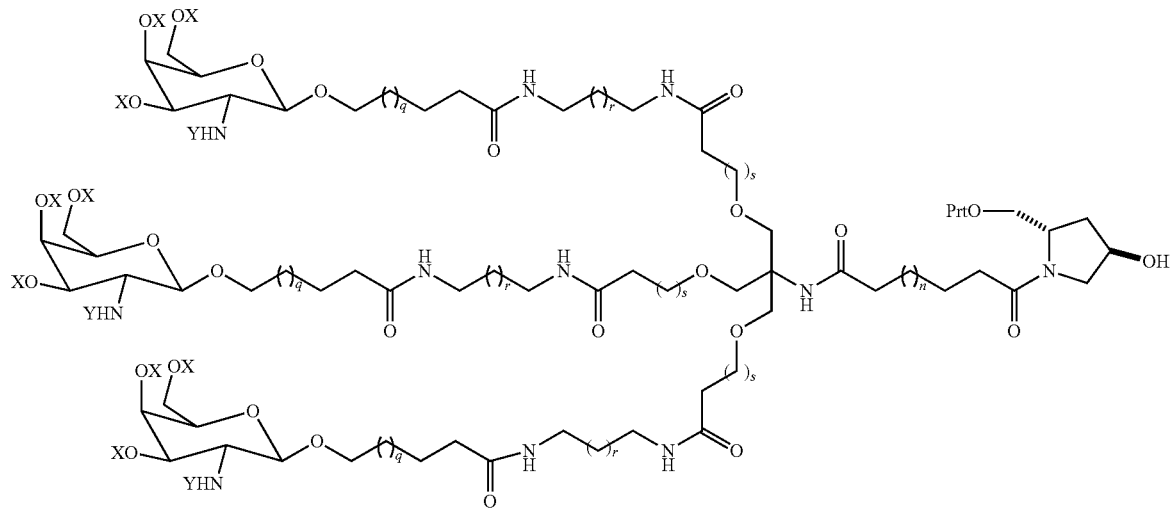

(XIV)

with dihydrofuran-2,5-dione in the presence of a tertiary amine to give a compound of formula (XIII):

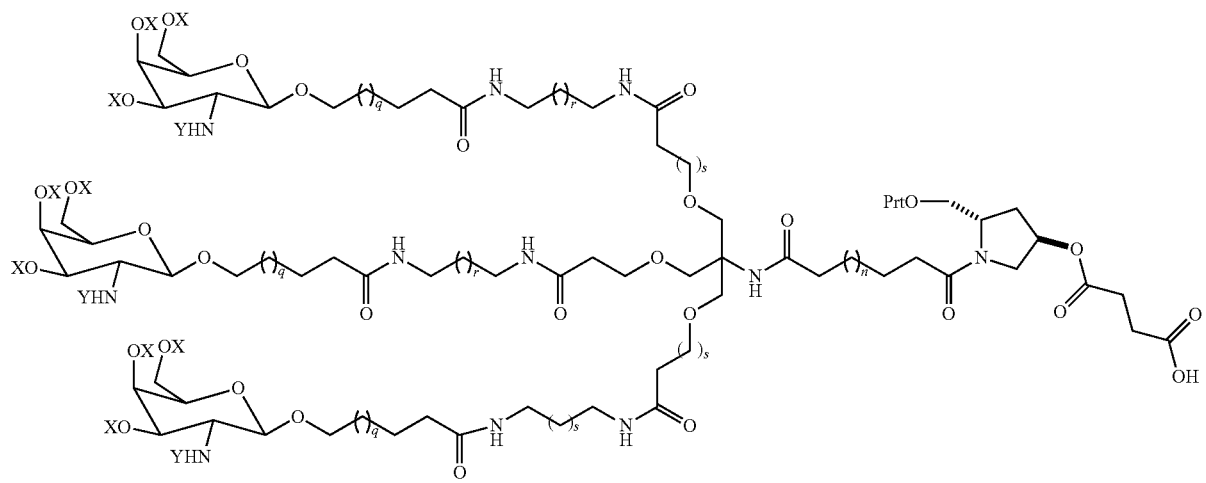

(XIII)

wherein
X is a hydroxyl protecting group;
Y is an amine protecting group;
Prt is a hydroxyl protecting group;
n is 0-15; and
q, r and s are each, independently, 1-7; and b) converting the compound of formula (XIII) to a compound of formula (A);
wherein the compound of formula (A) is free or substantially free of one or more of
 (i) metal impurities,
 (ii) each of the following two urea side products

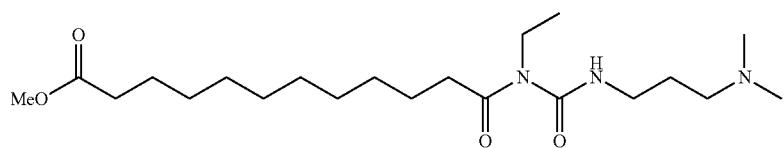

Urea 1

-continued
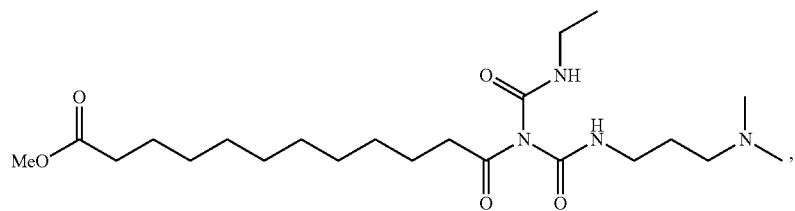
and
(iii) each of the following saccharide compounds
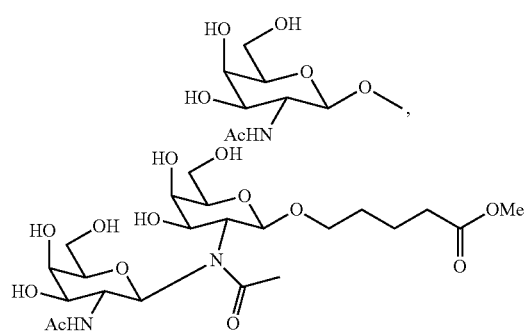
and
-continued
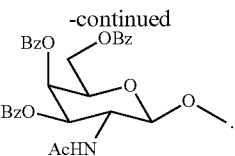
10. The process of claim 9, wherein the tertiary amine is triethylamine or pyridine.
* * * * *